(12) United States Patent
Gao et al.

(10) Patent No.: US 9,216,997 B2
(45) Date of Patent: Dec. 22, 2015

(54) TRI-HETEROCYCLIC DERIVATIVES, PREPARATION PROCESS AND USES THEREOF

(71) Applicant: SHANGHAI DE NOVO PHARMATECH CO LTD., Shanghai (CN)

(72) Inventors: Daxin Gao, Thousand Oaks, CA (US); Heping Yang, Shanghai (CN); Yajun Yu, Shanghai (CN)

(73) Assignee: Shanghai De Novo Pharmatech Co Ltd., Shanghai (CN)

( * ) Notice: Subject to any disclaimer, the term of this patent is extended or adjusted under 35 U.S.C. 154(b) by 0 days.

(21) Appl. No.: 14/356,982

(22) PCT Filed: Dec. 13, 2012

(86) PCT No.: PCT/CN2012/086492
§ 371 (c)(1),
(2) Date: May 8, 2014

(87) PCT Pub. No.: WO2013/091502
PCT Pub. Date: Jun. 27, 2013

(65) Prior Publication Data
US 2014/0329800 A1    Nov. 6, 2014

(30) Foreign Application Priority Data

Dec. 20, 2011 (CN) .......................... 2011 1 0430906
Sep. 12, 2012 (CN) .......................... 2012 1 0337103

(51) Int. Cl.
C07D 513/04    (2006.01)
C07D 513/14    (2006.01)
A61K 31/429    (2006.01)

(52) U.S. Cl.
CPC ............ *C07D 513/04* (2013.01); *A61K 31/429* (2013.01); *C07D 513/14* (2013.01)

(58) Field of Classification Search
CPC ... C07D 513/04; C07D 513/14; A61K 31/439
USPC ............................................ 546/83; 544/115
See application file for complete search history.

(56) References Cited

FOREIGN PATENT DOCUMENTS

| WO | WO 2007/109120 A2 | 9/2007 |
| WO | WO 2009/038757 A2 | 3/2009 |
| WO | WO 2010/054058 A1 | 5/2010 |
| WO | WO 2011/056764 A1 | 5/2011 |

OTHER PUBLICATIONS

International Preliminary Report on Patentability prepared by the State Intellectual Property Office of China for PCT/CN12/86492 on Mar. 20, 2014, 30 pages.
International Search Report prepared by the Chinese International Searching Authority for PCT/CN12/86492 on Mar. 21, 2013, 5 pages.
Chao et al. *J. Med. Chem.* 2009, 52, 7808-7816 "Identification of N-(5-tert-Butyl-isoxazol-3-y1)-N'-{4-[7-(2-morpholin-4-y1-ethoxy)imidazo-[2,1-b][1,3]benzothiazol-2-yl]phenyl }urea Dihydrochloride (AC220), a Uniquely Potent, Selective, and Efficacious FMS-Like Tyrosine Kinase-3 (FLT3) Inhibitor".

*Primary Examiner* — Rita Desai
(74) *Attorney, Agent, or Firm* — Swanson & Bratschun, L.L.C.

(57) ABSTRACT

The present invention relates to a tri-heterocyclic derivatives, preparation process and uses thereof, specifically relates to a tri-heterocyclic derivatives of the formula (I) or a pharmaceutically acceptable salt thereof, preparation process, and further relates to a pharmaceutically acceptable composition comprising compounds of formula (I), or a pharmaceutically acceptable salt thereof, and their pharmaceutical use as inhibitors of kinase.

9 Claims, 1 Drawing Sheet

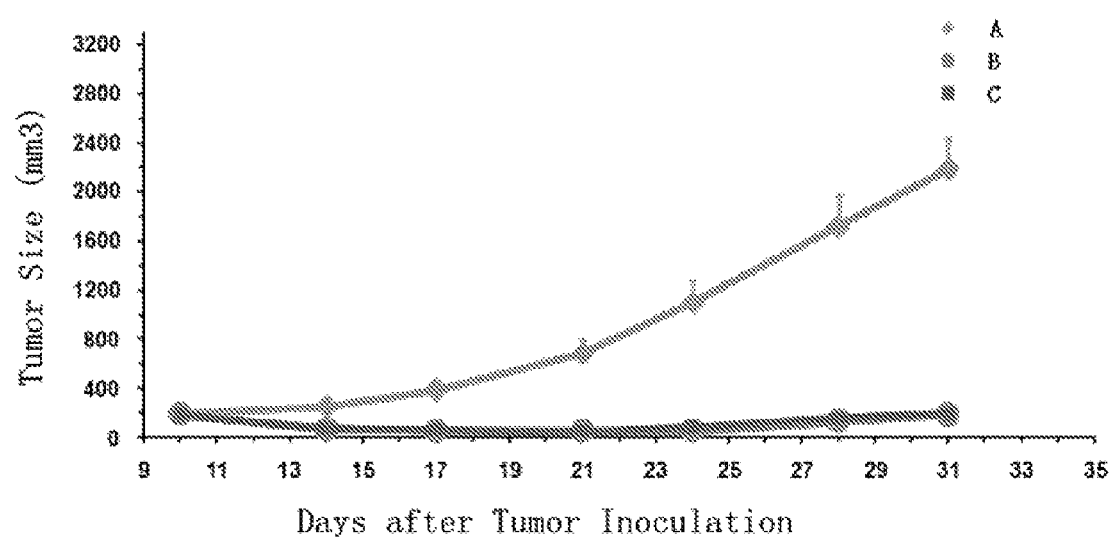

TRI-HETEROCYCLIC DERIVATIVES, PREPARATION PROCESS AND USES THEREOF

RELATED APPLICATIONS

This application is a 35 U.S.C. §371 national phase application of PCT/CN2012/086492 (WO 2013/091502), filed on Dec. 13, 2012, entitled "TRI-HETEROCYCLIC DERIVATIVES, PREPARATION PROCESS AND USES THEREOF", which application claims the benefit of Chinese Application No. 201110430906.3, filed Dec. 20, 2011, and Chinese Application No. 201210337103.8, filed Sep. 12, 2012, all of which are incorporated herein by reference in their entirety.

FIELD OF THE INVENTION

The present invention belongs to pharmaceutical chemistry field, and relates to a compound as protein kinase inhibitor, preaparation process, composition containing the same and uses thereof; specifically relates to a new tri-heterocyclic derivatives, preaparation process, composition containing the same and uses thereof, particularly to their pharmaceutical use as inhibitors of kinase.

BACKGROUND OF THE INVENTION

Protein kinases are a large family of proteins that play a pivotal role in the regulation of a wide variety of cellular processes, maintaining control over cellular function. Protein tyrosine kinases may be classified as growth factor receptor (e.g. VEGFR, EGFR, PDGFR, FGFR and erbB2) or non-receptor (e.g. c-src and bcr-abl) kinases. Receptor tyrosine kinases (RTKs) play a key role in the regulation of cell proliferation, differentiation, metabolism, migration, and survival. Upon ligand binding, they undergo tyrosine phosphorylation at specific residues in the cytoplasmic tail. This leads to the binding of protein substrates and/or the establishment docking sites for adaptor proteins involved in RTK-mediated signal transduction. When unregulated, receptor tyrosine kinases can contribute to the rise of disease states associated with such aberrant kinase activity. Flt3 (FMS-like receptor tyrosine kinase-3), a member of class III tyrosine kinase receptor family, is predominantly expressed in hematopoietic progenitor cells and plays an important role in the pathogenesis of acute myeloid leukemia (AML). Flt3 is expressed in blast cells of most patients with AML including wild-type and two forms of Flt3 mutations. These two mutations identified in the AML patients are internal tandem duplication (ITD) mutations in the juxtamembrane domain and point mutations (TKD) in the activation loop of the TKD. (See, Ryan J. Mattison et al Reviews in *Reviews on Recent Clinical Trials*, 2007, 2, 135-141). The relapse rates in the Flt3/ITD mutation AML patients are significantly increased and the overall survival rates decreased compared with the AML patients without the Flt3 mutation. So development of a drug of inhibiting Flt3/ITD mutant kinase could provide an effective way to treat AML. Currently more than a dozen known Flt3 inhibitors are being developed and some have shown promising clinical effects against AML (See Levis et al. Int J Hematol, 2005, 82:100-107).

A large portion of DCs are derived from hematopoietic progenitors that express FLT3 receptor (CD135), and stimulation of the receptor via FLT3 ligand either in vivo or in vitro is known to drive expansion and differentiation of these progenitors toward a DC phenotype. Since dendritic cells are the central antigen-presenting cells for initiation of T cell responses to mediate immune response including the autoreactive immune response. Inhibition of FLT3 signaling may thus produce an inhibition of DC-induced stimulation of T cells, thereby inhibiting autoimmune responses. One study shows the Flt3 inhibitor CEP-701, a drug already known to block actions of the growth-promoting FLT3 gene, to be effective in mice model engineered to mimic multiple sclerosis (MS model). Multiple sclerosis is a disease that causes T-cells to destroy the myelin protein sheath around nerves in the central nervous system. This study shows Flt3 inhibitor CEP-701 to be effective in reducing myelin loss in the MS mice model. (See Whartenby et al. PNAS (2005) 102: 16741-16746). The study also shows that hemopoietic cytokines such as Flt3 ligand (a dendritic cell-mobilizing factor) and M-CSF are elevated significantly in the serum of patients with Langerhans cell histiocytosis and systemic lupus erythematosus. Higher level of cytokines correlated with patients having more extensive diseases. The highest serum level of Flt3 and M-CSF were linked with the patients with high risk of extensive skin and/or multisystem involvement, which further implicates Flt3 signaling in the disregulation of dendritic cell progenitors in those autoimmune diseases (See Rolland et al. J. Immunol., 2005, 174:3067-3071).

There is considerable interest in the development of kinase inhibitors for use in cancer therapy. Among them, urea derivatives have been reported to be selective Flt3 inhibitors in Bioorg. Med. Chem. Lett. 10:2051-2054 (2000), WO 99/32106 published 1 Jul. 1999, PCT publication WO 99/32111 published 1 Jul. 1999 and PCT publication WO2007/109120 published in 27 Sep. 2007.

SUMMARY OF THE INVENTION

The present inventors have now discovered a new kind of tri-heterocyclic derivatives, preaparation process, composition containing the same and uses thereof, particularly to their pharmaceutical use as inhibitors of kinase. The compounds exhibit a surprising increase in the level of inhibition of MV4-11 cell proliferation (MV4-11 cell is a human leukemia cell lines that express a FLT3-ITD mutation), and/or a surprising increase in the solubility of the compound (in aqueous media and/or phosphate buffer solution)-enhanced solubility may be of use in formulation the compounds, for example, for administration by an IV route, or for oral formulations (e.g. liquid and small tablet forms) for pediatric use. The oral bioavailability of the compounds of the present invention may be enhanced. The compounds may also be less susceptible to the action of MDR1 in cells.

Accordingly, the first aspect of the present invention provides a compound of formula (I) or a pharmaceutically acceptable salt thereof:

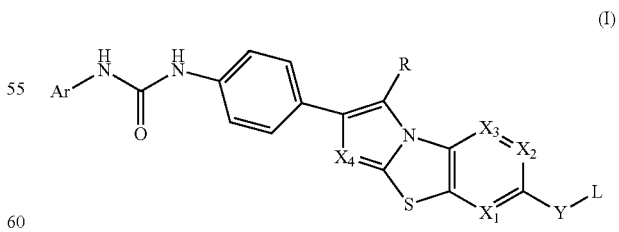

Wherein:

Ar is selected from the group consisting of optionally substituted or unsubstituted aryl, and optionally substituted or unsubstituted heteroaryl, when substituted, the substituents could be one or more groups independently selected from halogen, alkyl, haloalkyl, or hydroxyl alkyl;

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxylalkyl, alkoxyl, —NHalkylhydroxyl, —NHalkoxyalkyl, —NHalkylamnio, —NHcycloalkyl, —NHcycloalkylalkyl, —N Hheterocycloalkyl, —NH heterocycloalkylalkyl, —NHaryl, —NHarylalkyl, —NHheteroaryl, or —NHheteroarylalkyl;

Y is O, S, $NR_2R_2'$ or a direct bond (that means L directly connected with the left heteroaryl);

$X_1$, $X_2$, $X_3$ and $X_4$ are independently N or $CR_1$, $R_1$ is H, or —Y-L;

R, $R_2$ and $R_2'$ are each independently selected from the group consisting of hydrogen, alkyl, cycloalkyl, aryl, heteroaryl, haloalkoxyl, hydroxyl, amino, aminocarbonyl, sulfonamido, cyano, alkynyl, alkoxyl, aryloxyl, carboxylic acid, carboxylic ester or halogen, or $R_2$, $R_2'$ together with the nitrogen atom to which they are attached, form a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

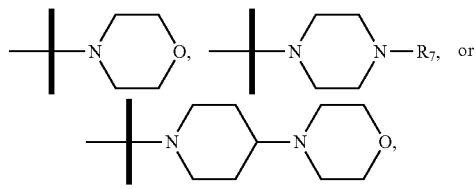

and $R_7$ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, iso-hexyl.

One preferably subset of compound of the present invention provides formula (I) or a pharmaceutically acceptable salt thereof, wherein:

Ar is

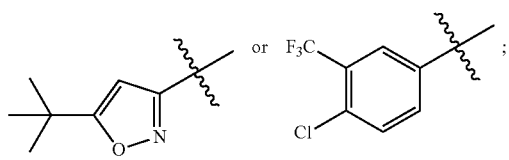

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl, when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NH heteroarylalkyl;

Y is O, S, $NR_2R_2'$ or a direct bond;

$X_1$, $X_2$, $X_3$ and $X_4$ are independently N or $CR_1$, $R_1$ is H, or —Y-L;

R, $R_2$ and $R_2'$ are each independently selected from the group consisting of hydrogen, alkyl, cycloalkyl, aryl, heteroaryl, haloalkoxyl, hydroxyl, amino, amido, aminocarbonyl, sulfonamido, cyano, alkynyl, alkoxyl, aryloxyl, carboxylic acid, carboxylic ester or halogen, or $R_2$, $R_2'$ together with the nitrogen atom to which they are attached, form a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

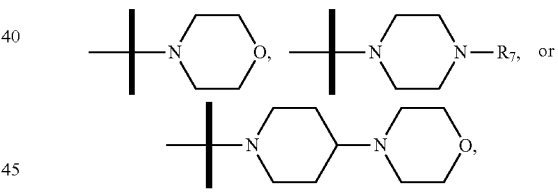

and $R_7$ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, iso-hexyl.

Another preferably subset of compound of the present invention provides formula (I) or a pharmaceutically acceptable salt thereof, wherein:

Ar is

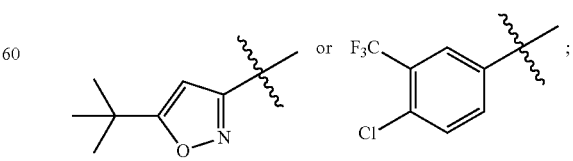

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl, when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NH heteroarylalkyl;

Y is O, S or $NR_2R_2'$;

$X_1, X_2, X_3$ and $X_4$ are independently N or $CR_1$, $R_1$ is H, or —Y-L;

R, $R_2$, and $R_2'$ are each independently selected from the group consisting of hydrogen or alkyl, or $R_2$, $R_2'$ together with the nitrogen atom to which they are attached, formed a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

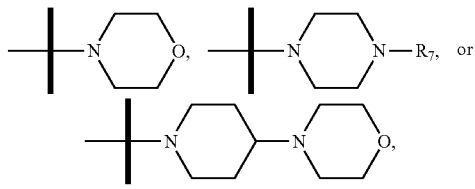

and $R_7$ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, isohexyl.

Another preferably subset of compound of the present invention provides formula (I) or a pharmaceutically acceptable salt thereof, wherein:

Ar is

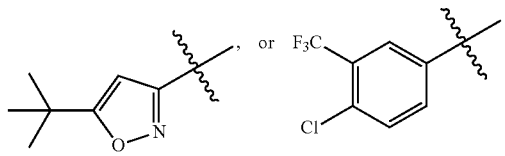

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NHheteroarylalkyl;

Y is O;

$X_1, X_2, X_3$ and $X_4$ are independently N or CH;

R is hydrogen.

Another preferably subset of compound of the present invention provides formula (I) or a pharmaceutically acceptable salt thereof, wherein:

Ar is

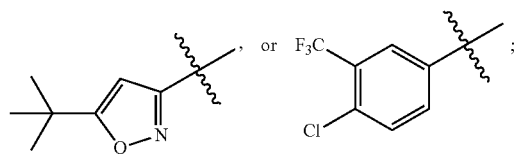

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NH heteroarylalkyl;

Y is $NR_2R_2'$;

$X_1, X_2, X_3$ and $X_4$ are independently N or CH;

R is hydrogen;

$R_2$, $R_2'$ is hydrogen or alkyl, or $R_2$, $R_2'$ together with the nitrogen atom to which they are attached, formed a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

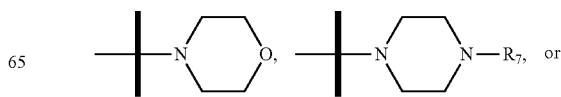

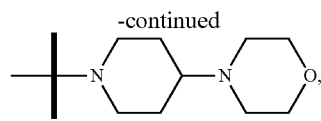

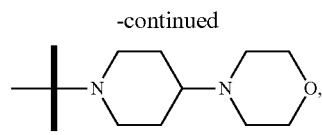

and R₇ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, iso-hexyl.

Another preferably subset of compound of the present invention provides formula (I) or a pharmaceutically acceptable salt thereof, wherein:

Ar is

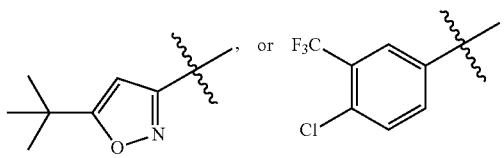

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NH heteroarylalkyl;

Y is a direct bond or O, S or $NR_2R_2'$;

$X_1$, $X_2$, $X_3$ and $X_4$ are independently $CR_1$;

$R_1$ is H, or —Y-L;

R is hydrogen;

$R_2$, $R_2'$ is hydrogen or alkyl, or $R_2$, $R_2'$ together with the nitrogen atom to which they are attached, formed a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

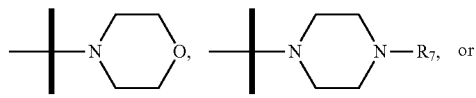

and R₇ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, iso-hexyl.

Another preferably subset of compound of the present invention provides formula (I) or a pharmaceutically acceptable salt thereof, wherein:

Ar is

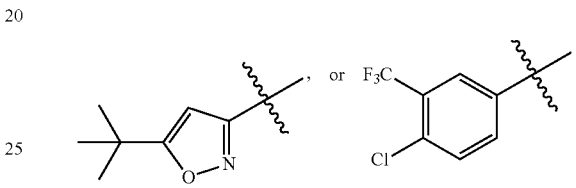

L is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —N Hheterocycloalkyl, —NHheterocycloalkylalkyl, —NHaryl, —NHarylalkyl, —NHheteroaryl, or —NHheteroarylalkyl;

Y is a direct bond;

$X_1$, $X_2$, $X_3$ and $X_4$ are independently N or $CR_1$, $R_1$ is H, or —Y-L;

R is independently selected from the group consisting of hydrogen, alkyl, cycloalkyl, aryl, heteroaryl, haloalkoxyl, hydroxyl, amino, aminocarbonyl, sulfonamido, cyano, alkynyl, alkoxyl, aryloxyl, carboxylic acid, carboxylic ester or halogen.

The present invention provides a compound of formula (I) or a pharmaceutically acceptable salt thereof, wherein the compounds are selected from, but not limited to the following compounds:

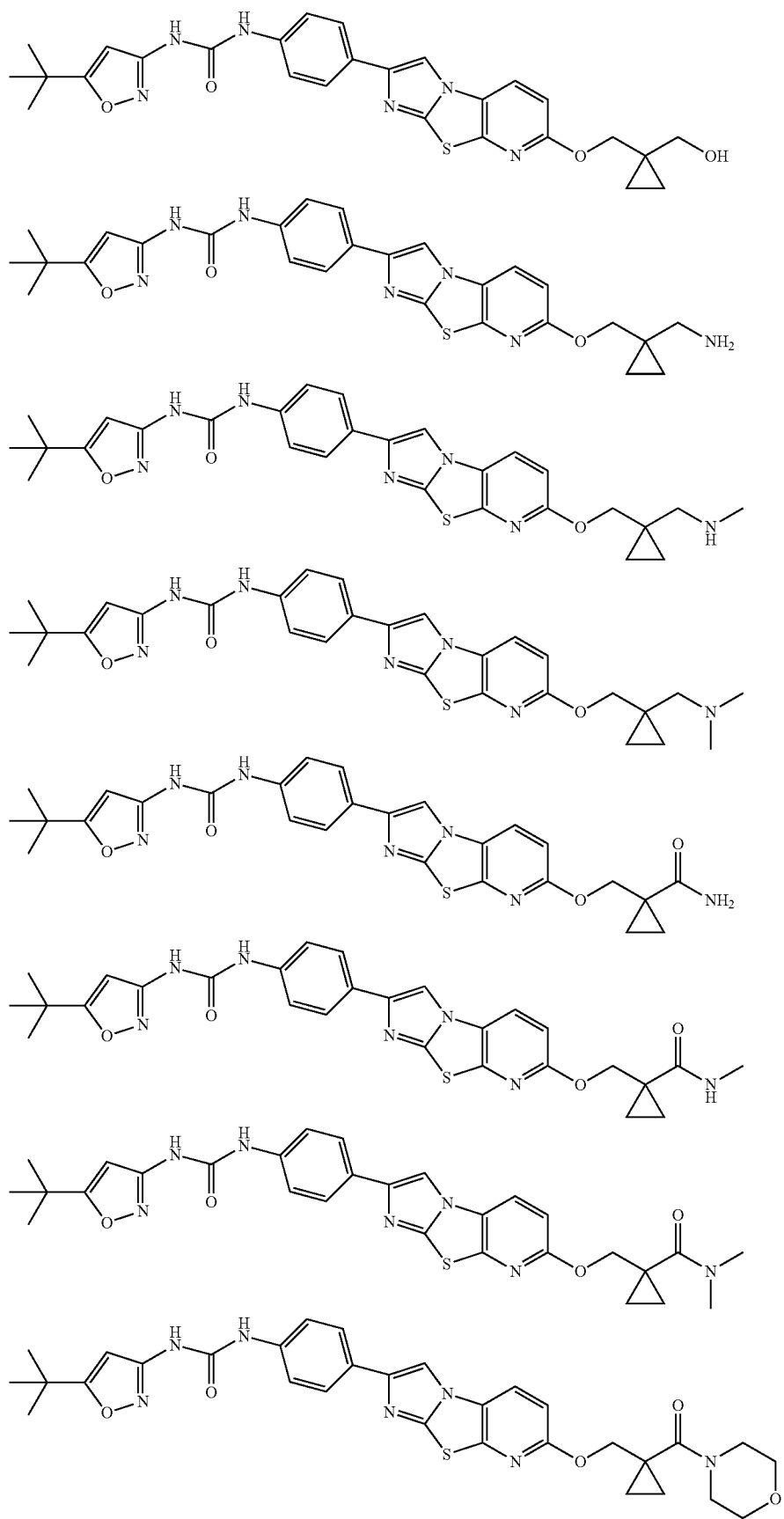

-continued
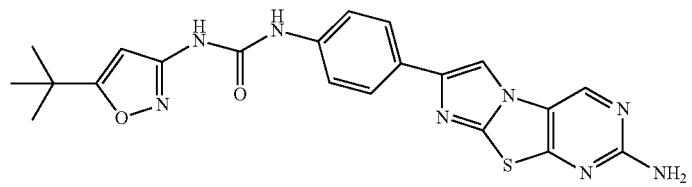
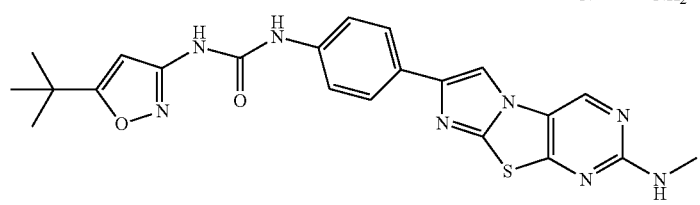
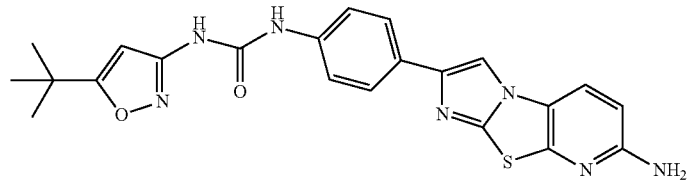
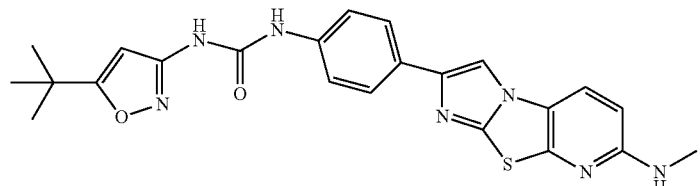
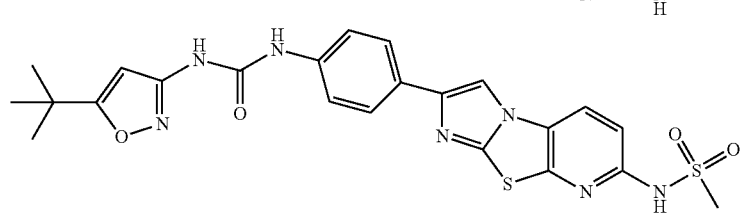
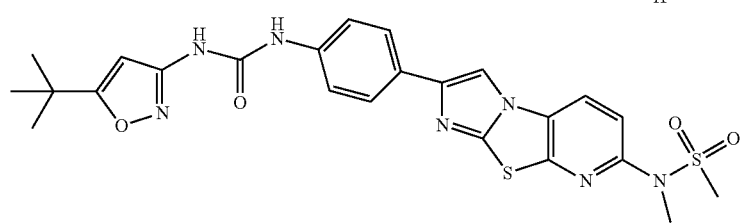
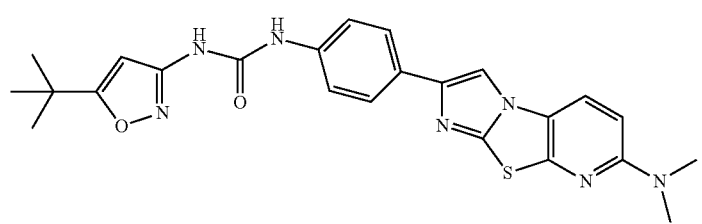
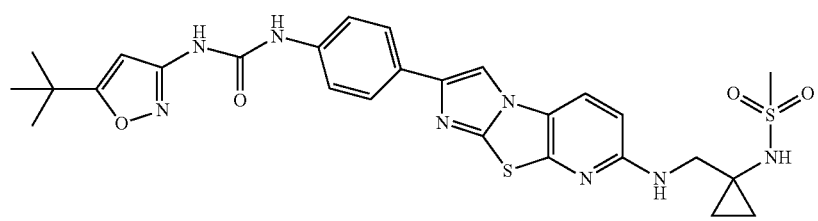

-continued
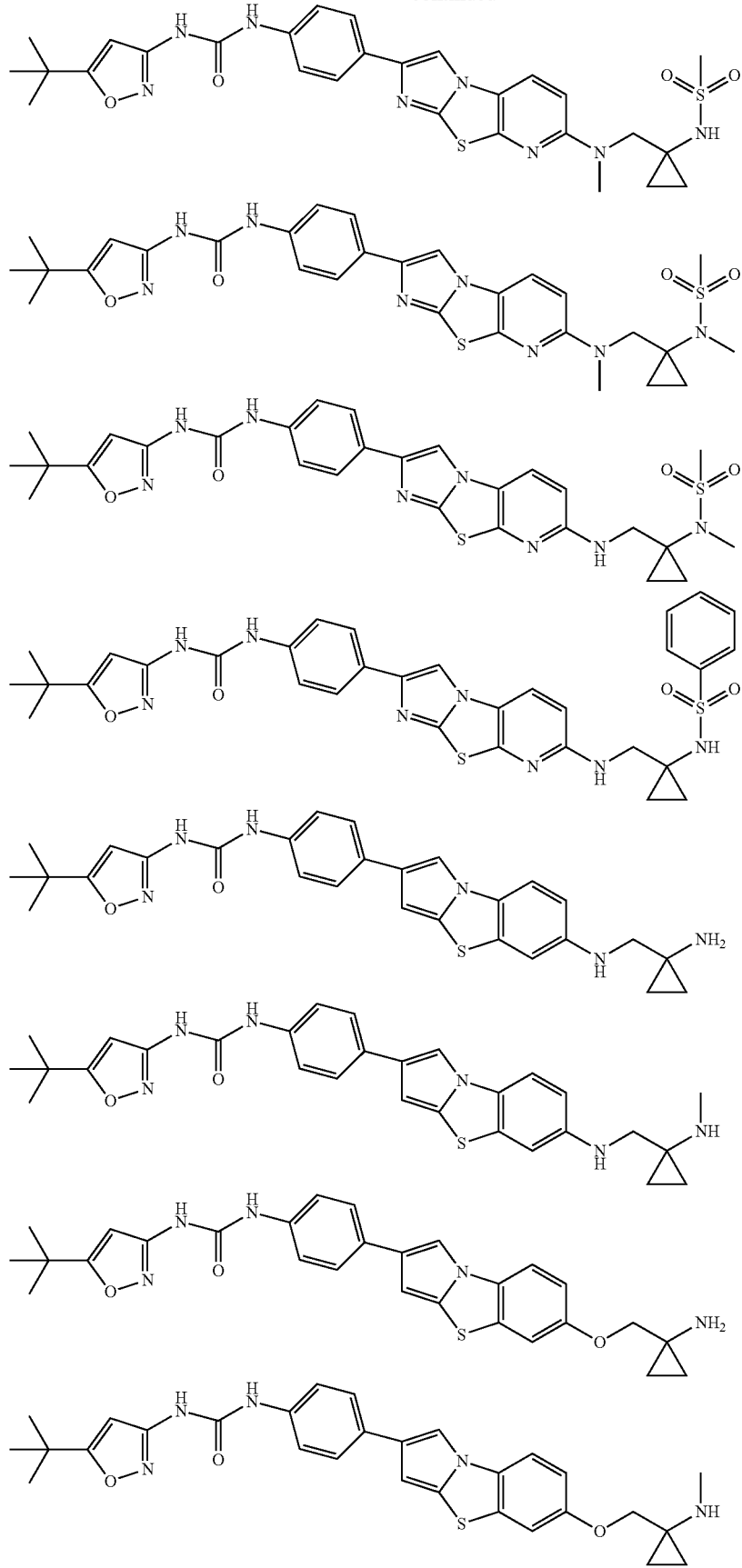

-continued
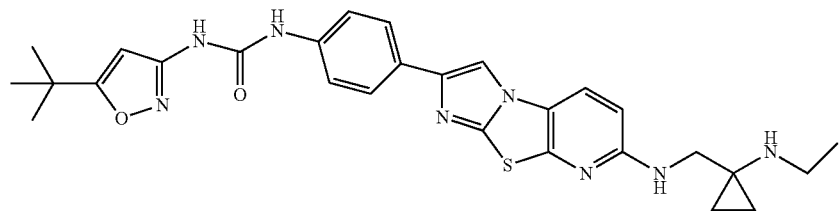
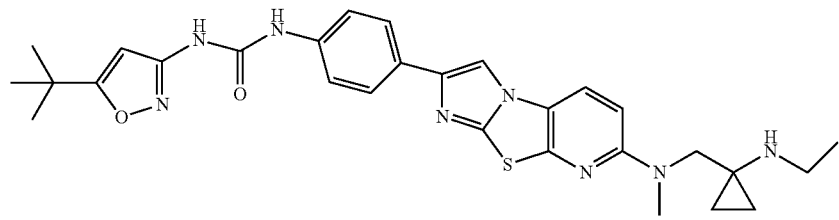
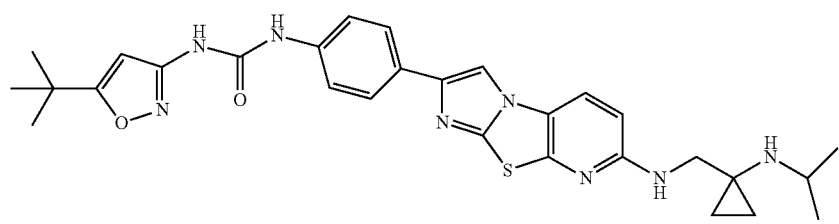
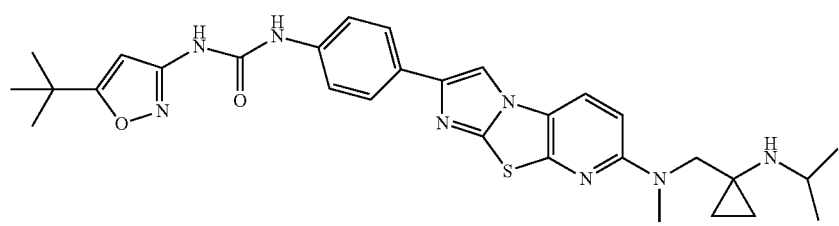
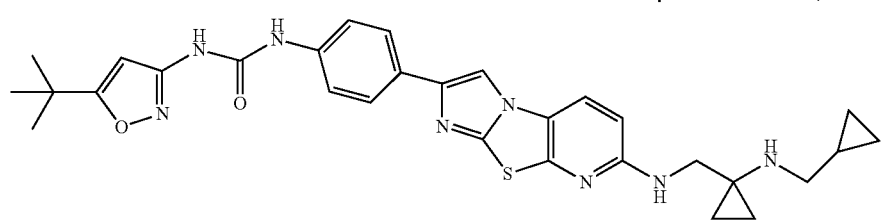
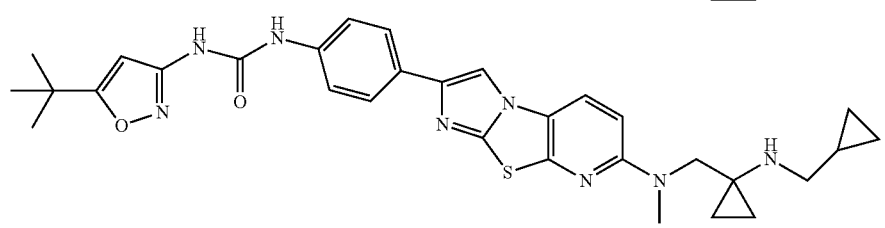
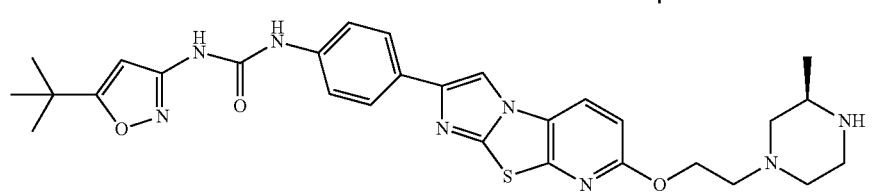
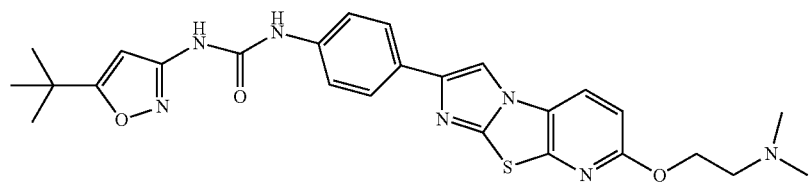

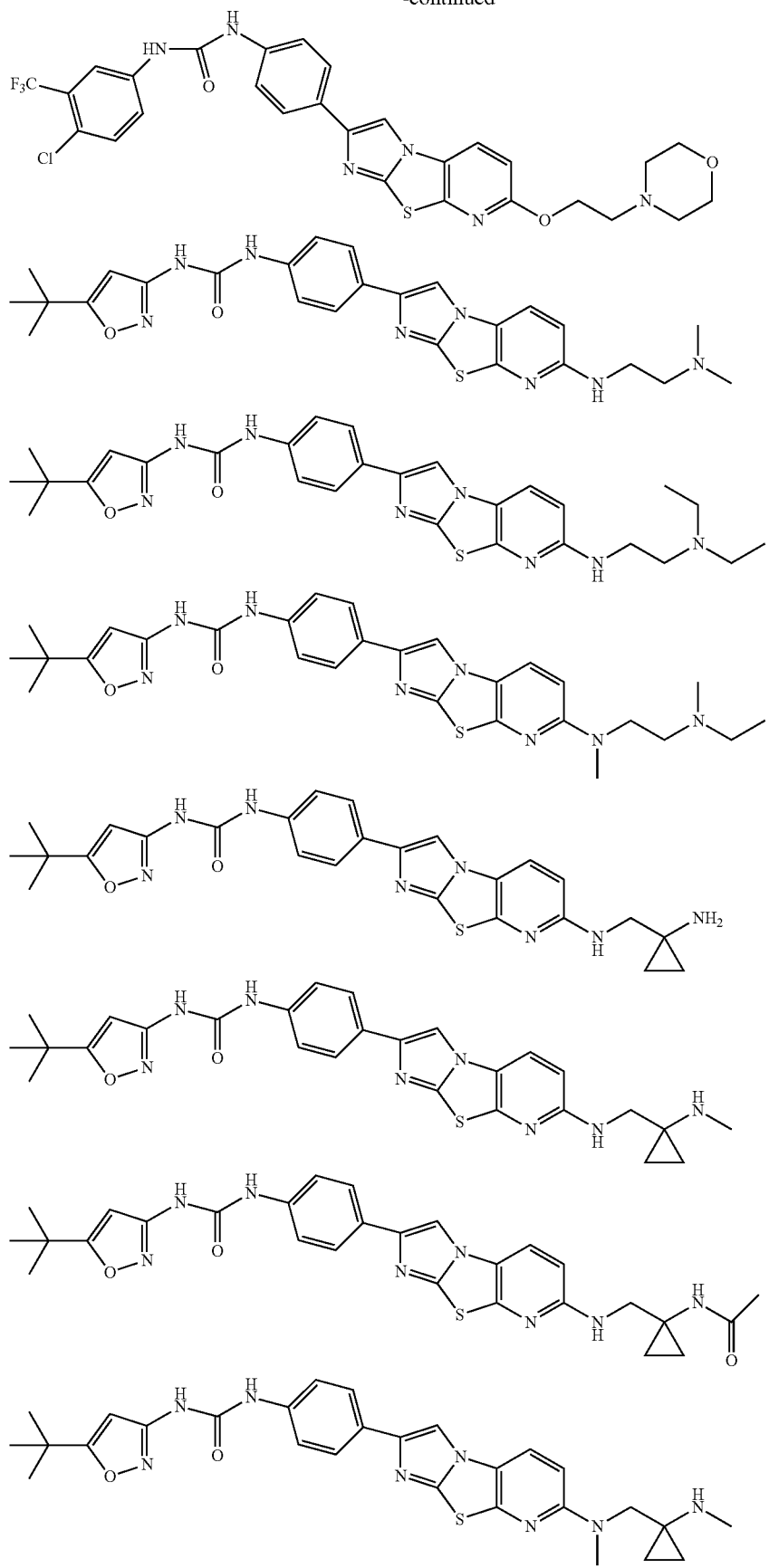

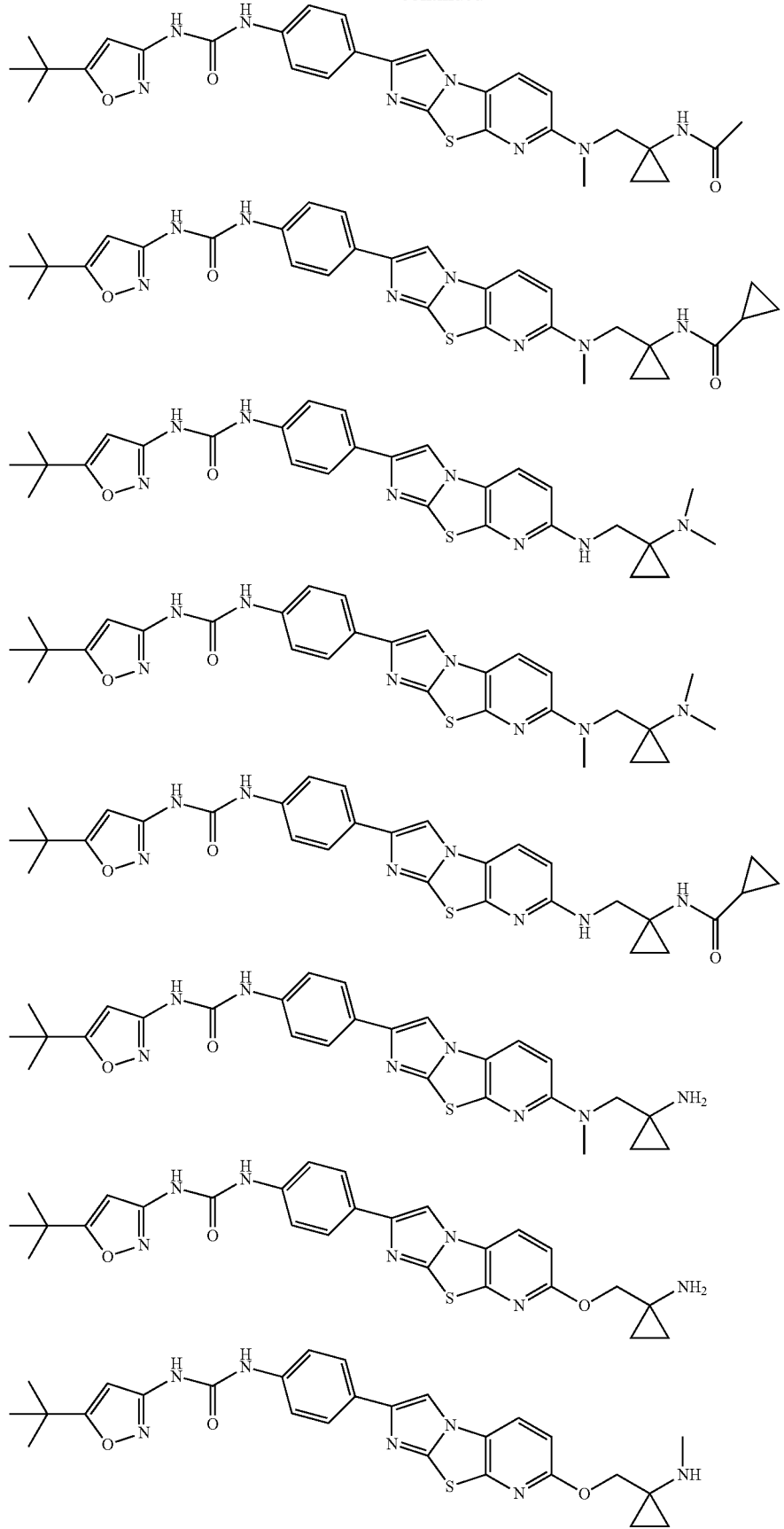

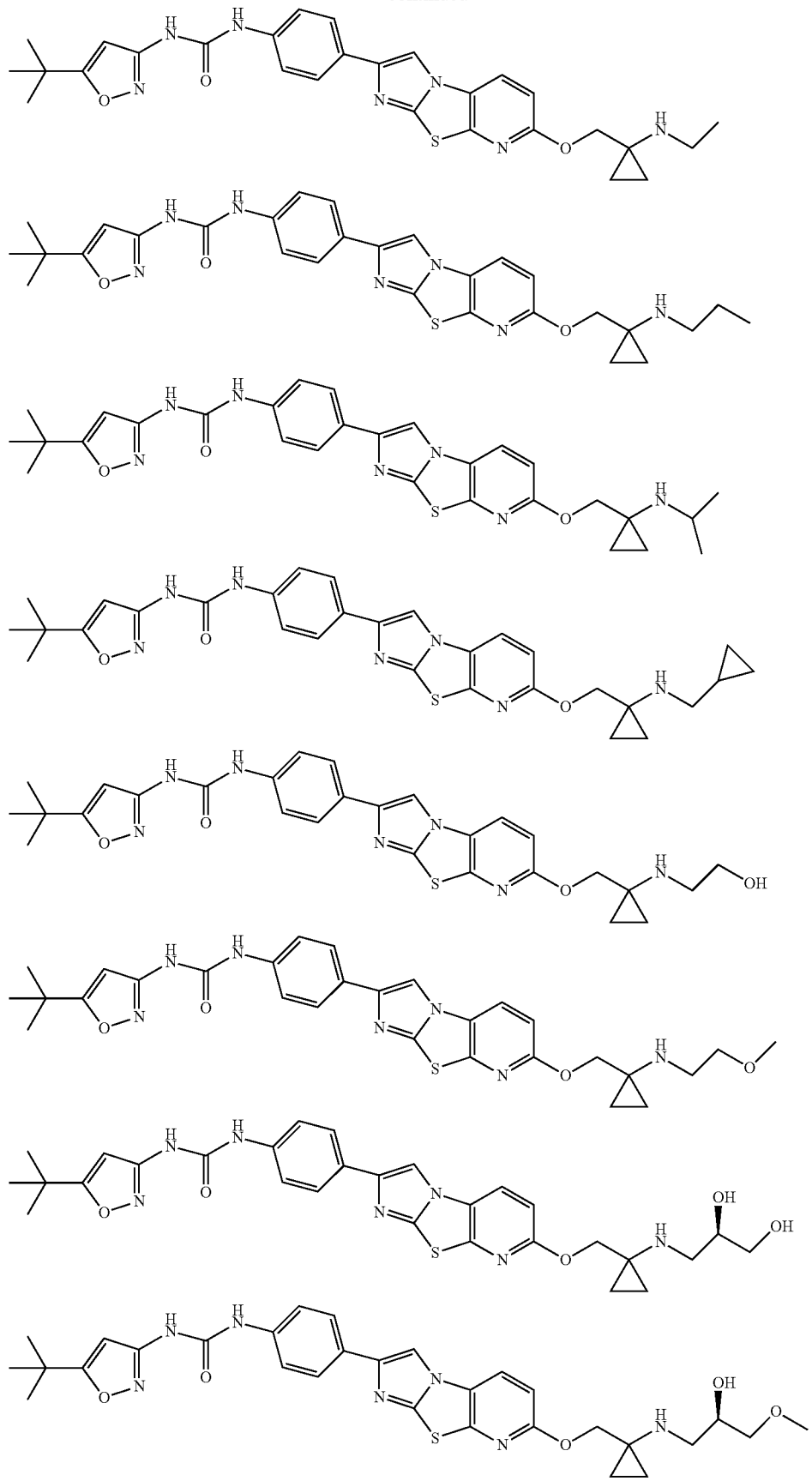

-continued
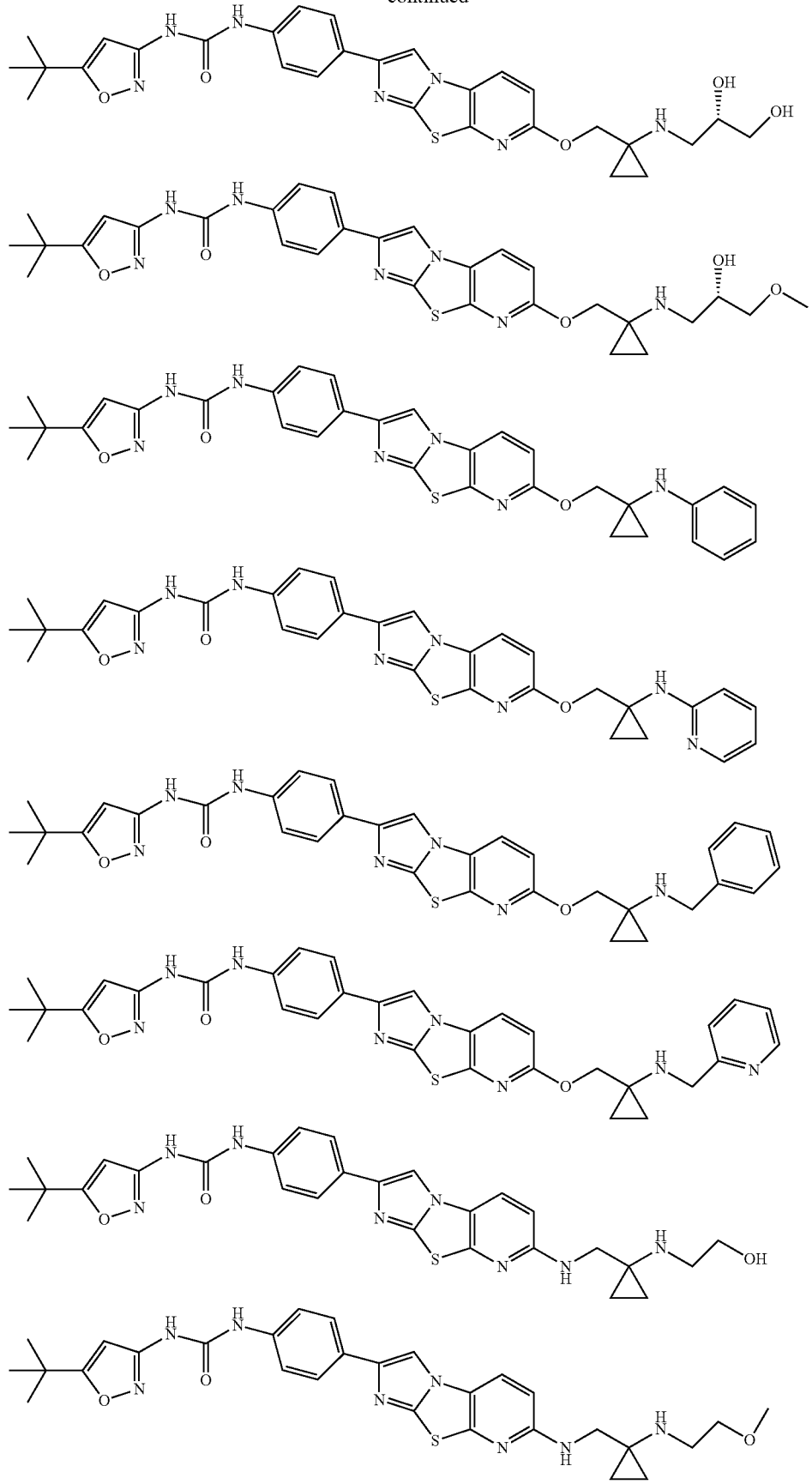

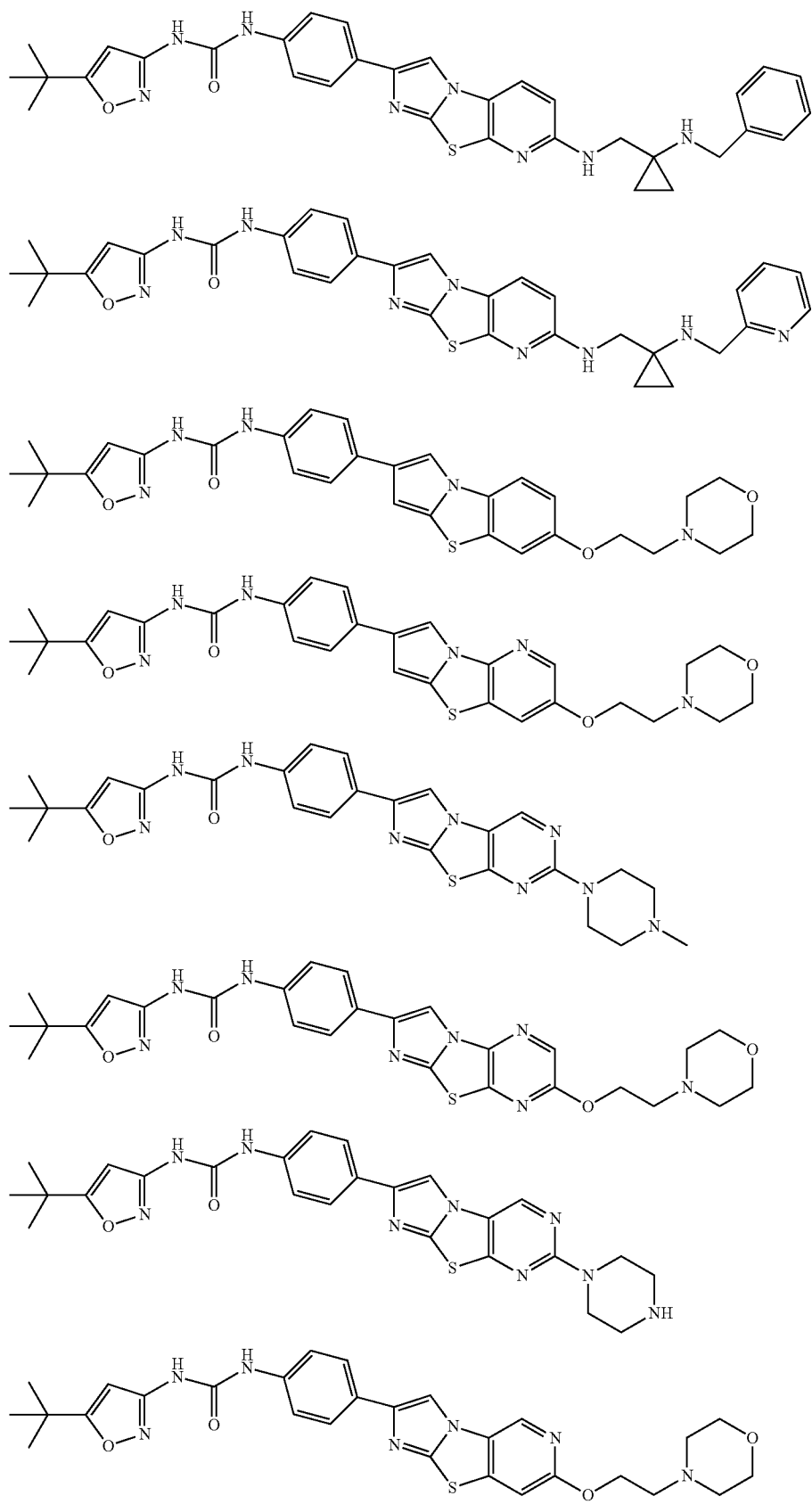

-continued
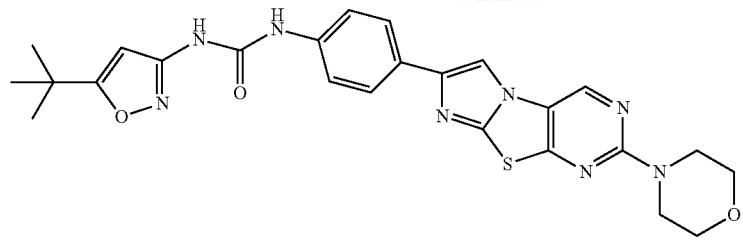
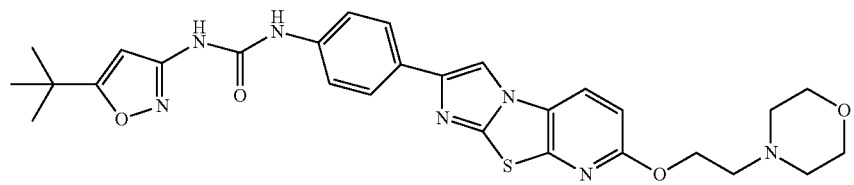
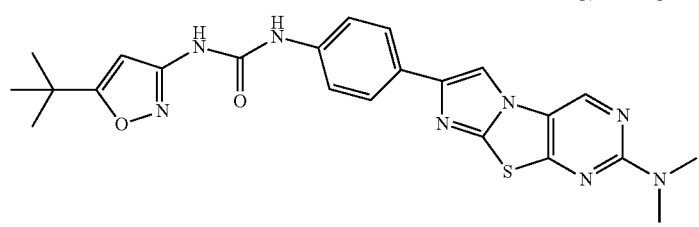
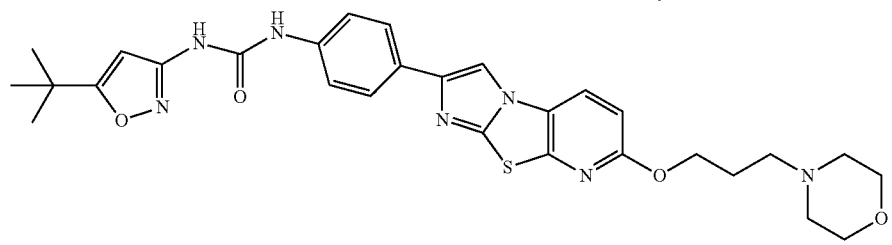
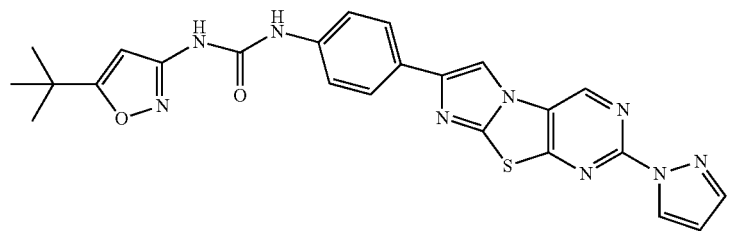
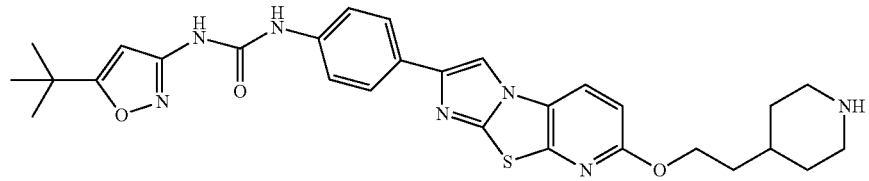
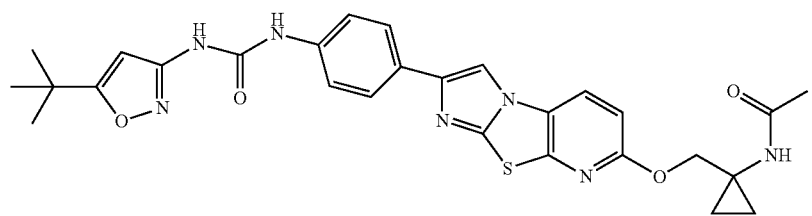
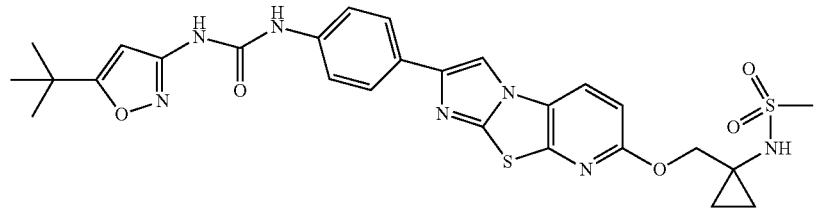

-continued
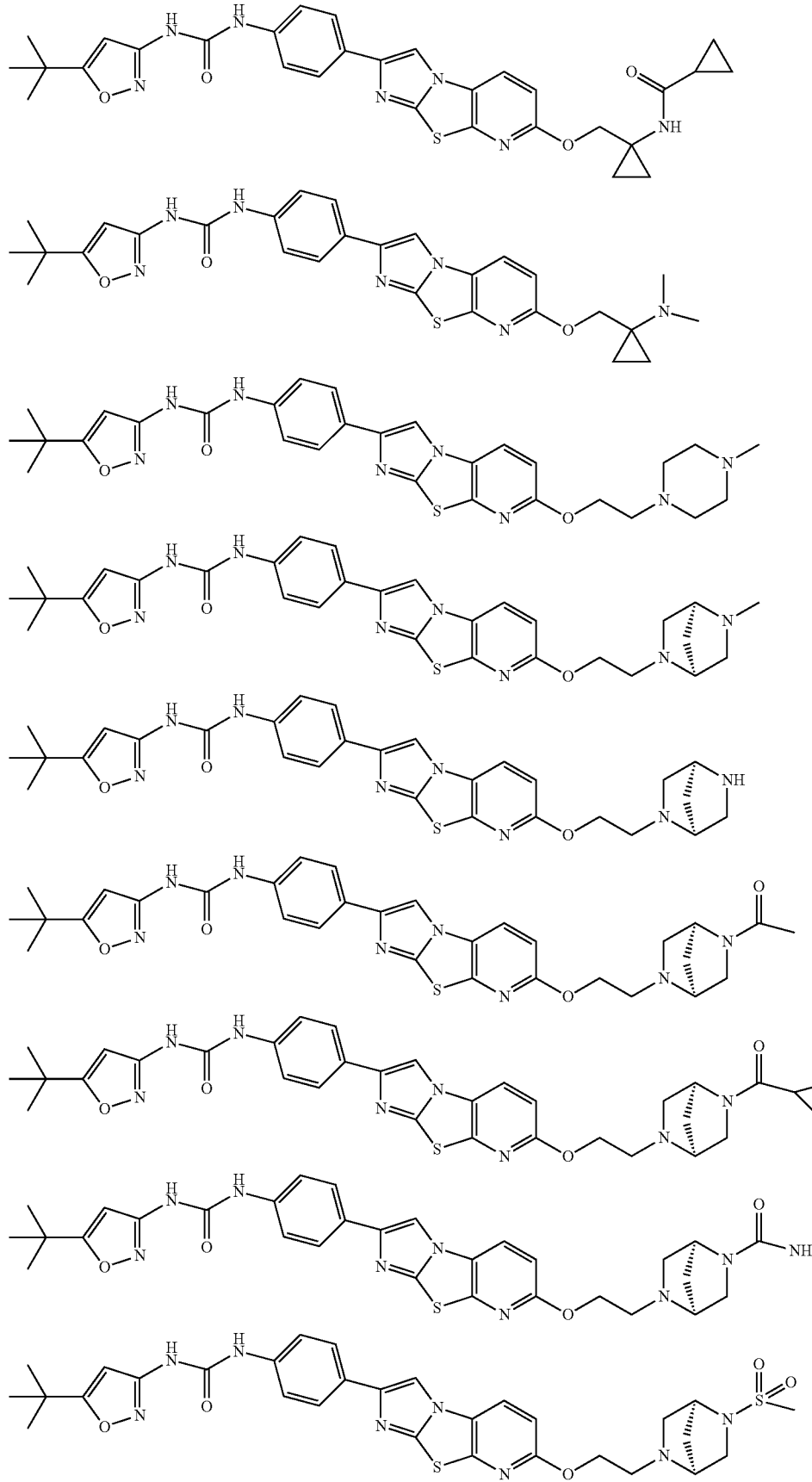

-continued
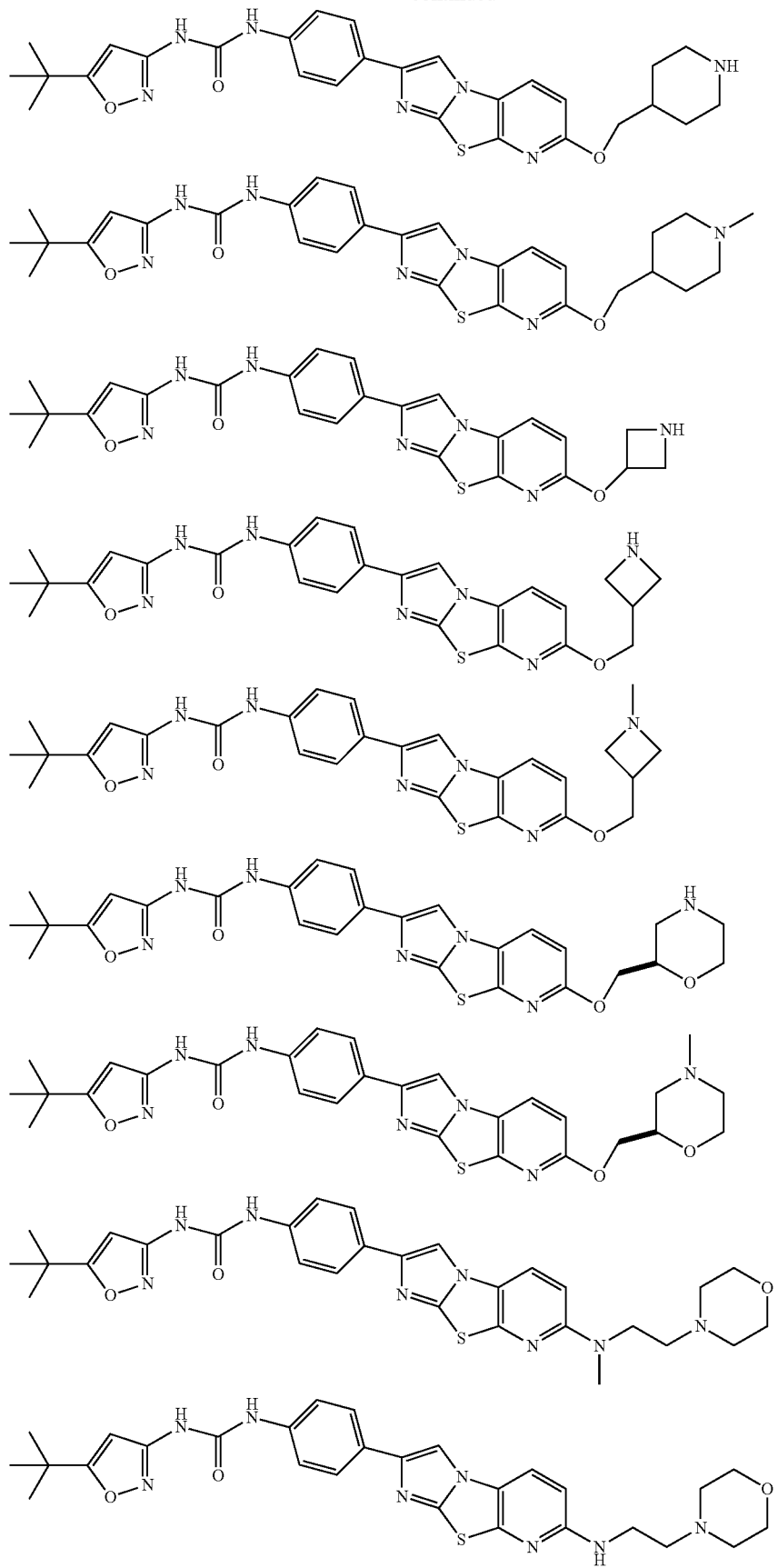

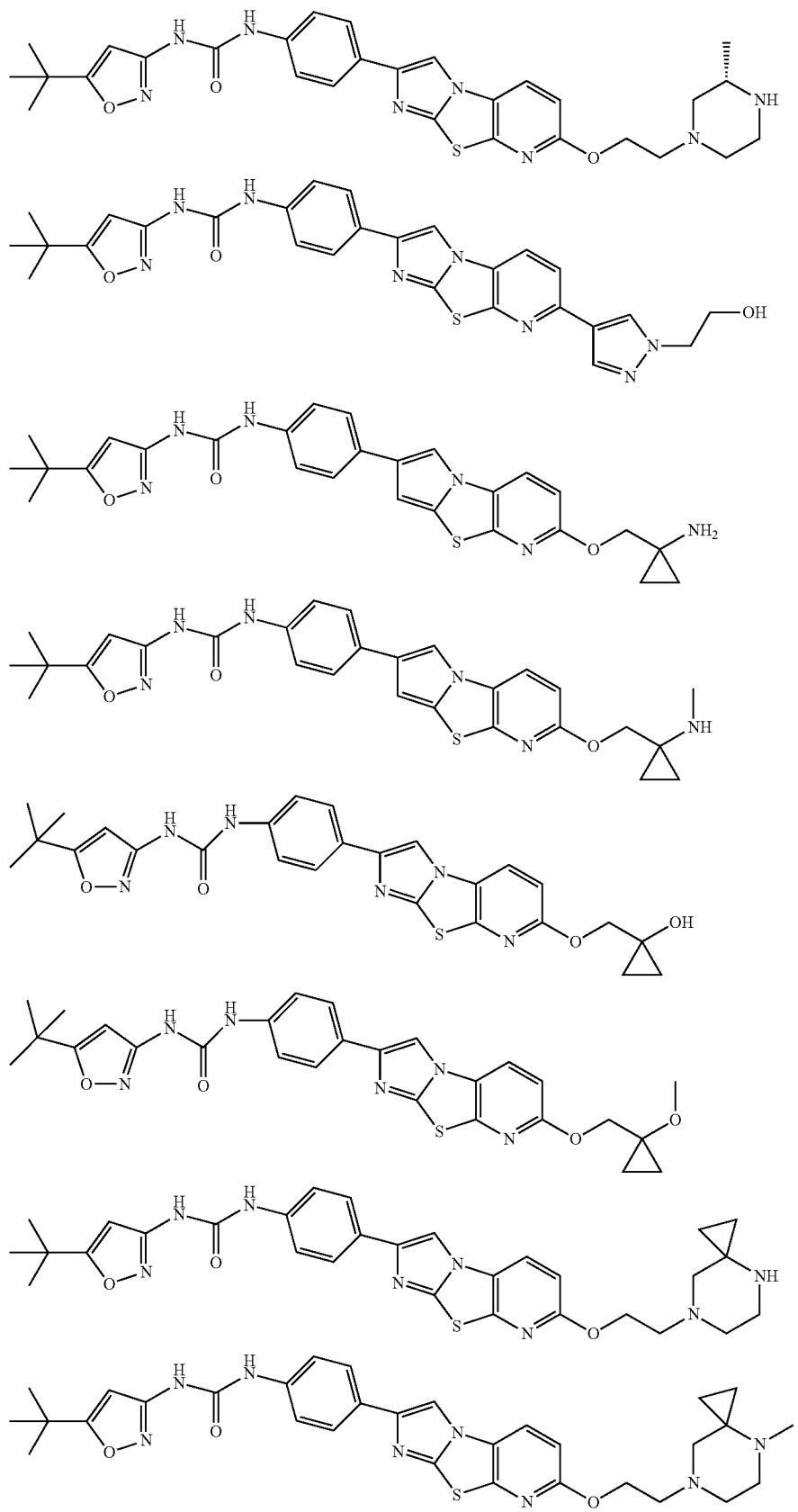

-continued
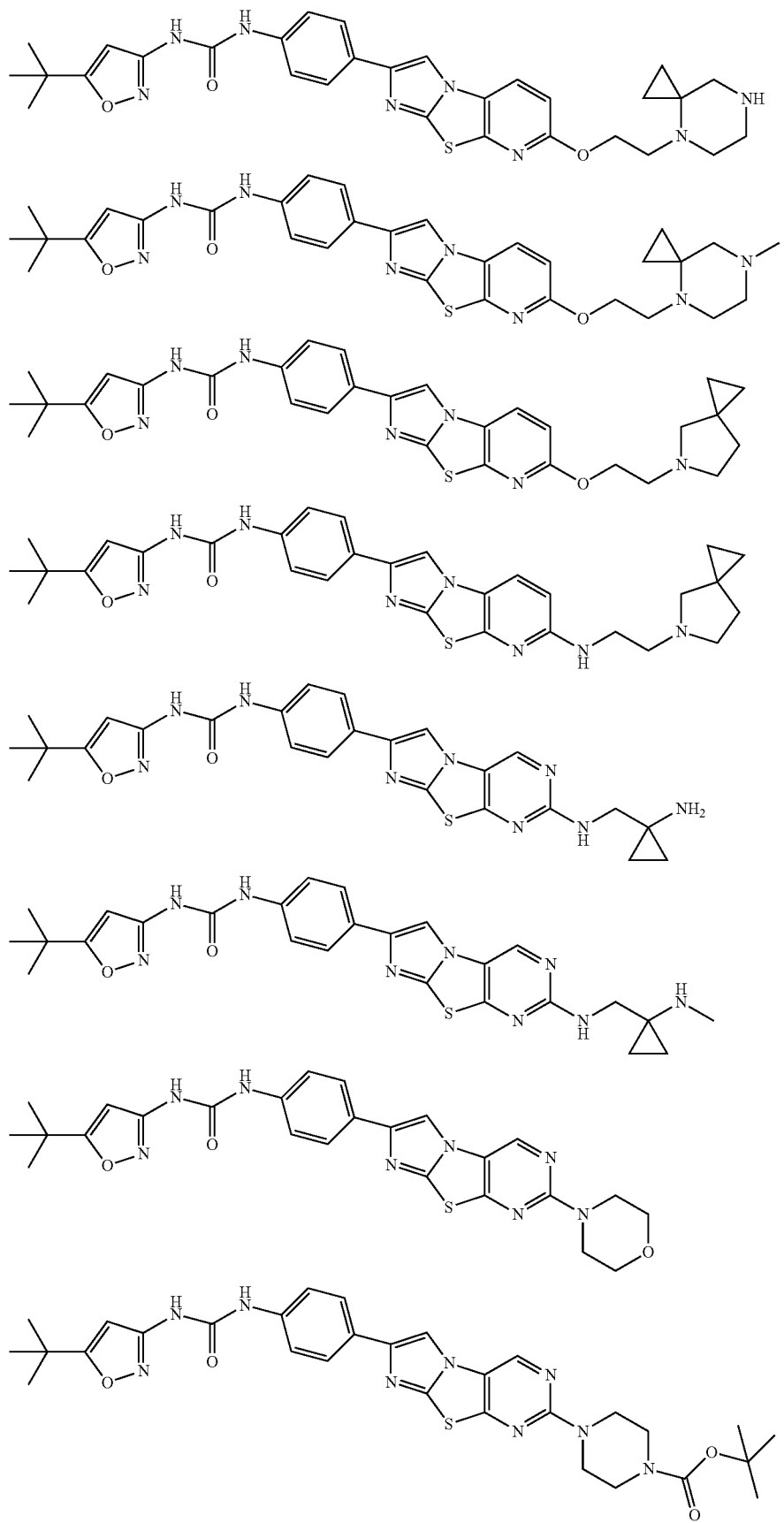

-continued
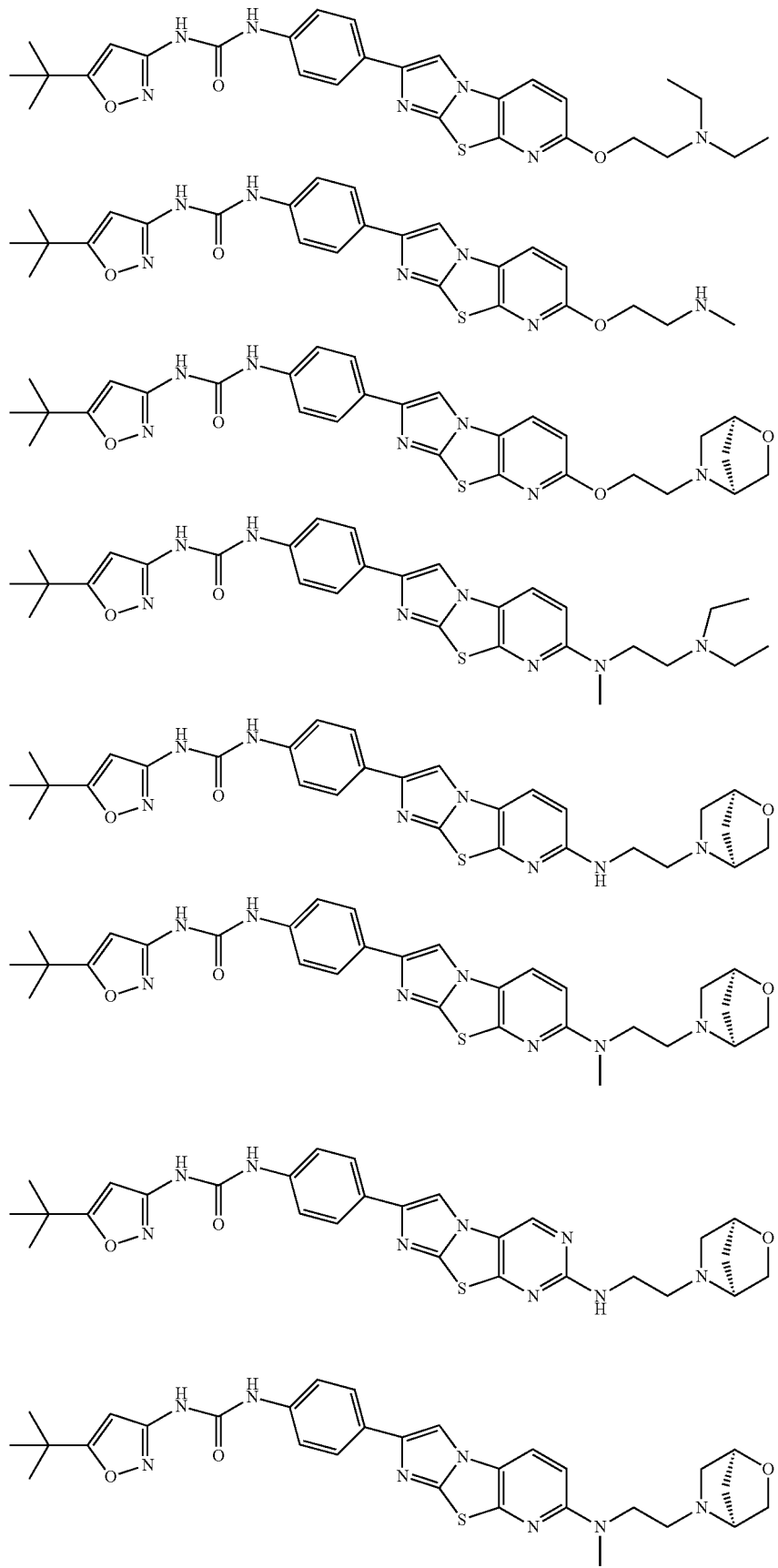

-continued
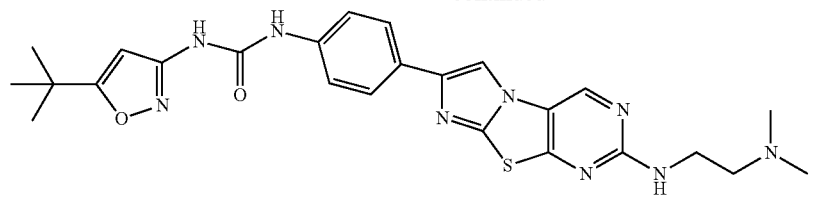
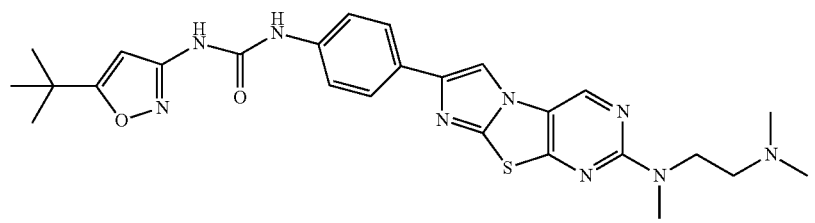
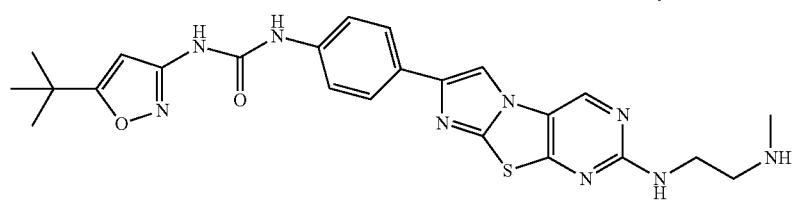
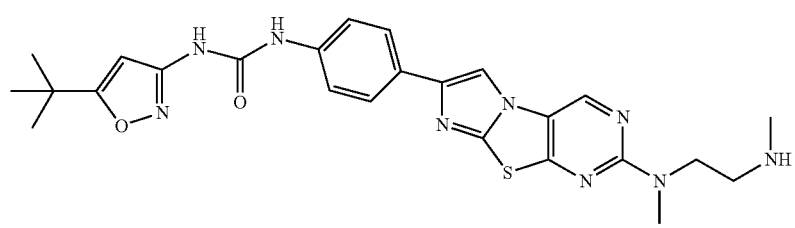
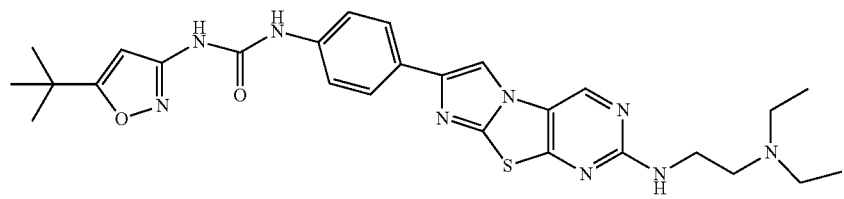
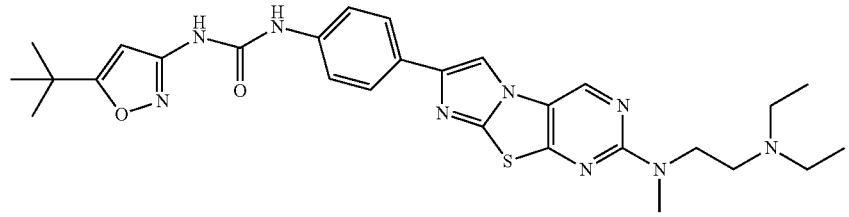
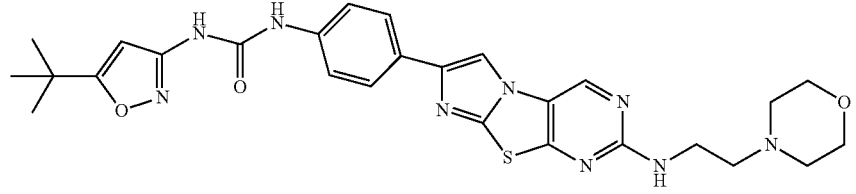
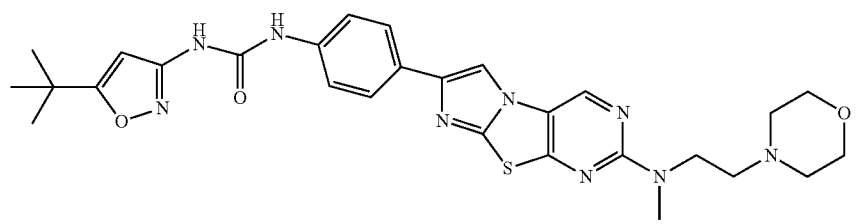

-continued
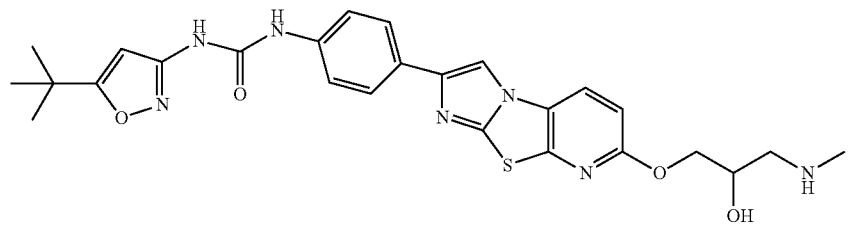
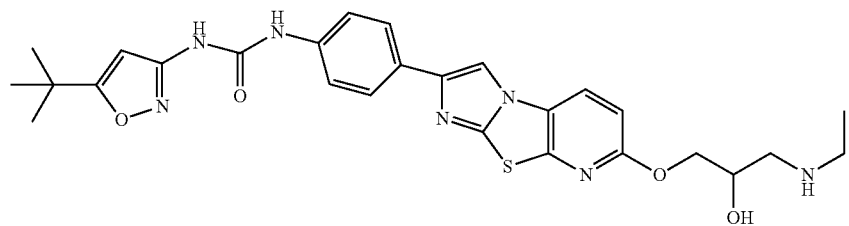
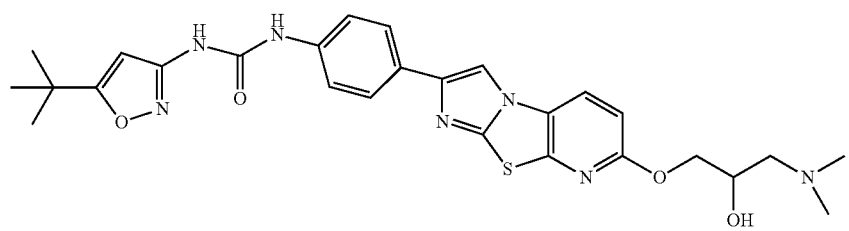
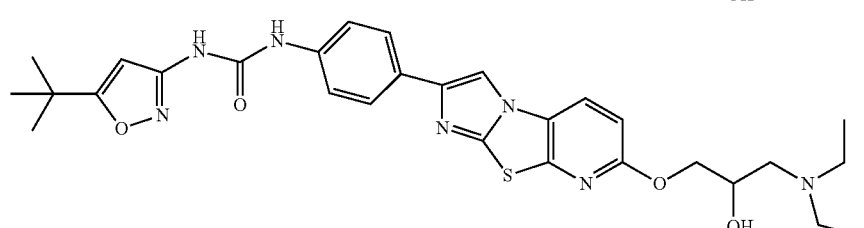
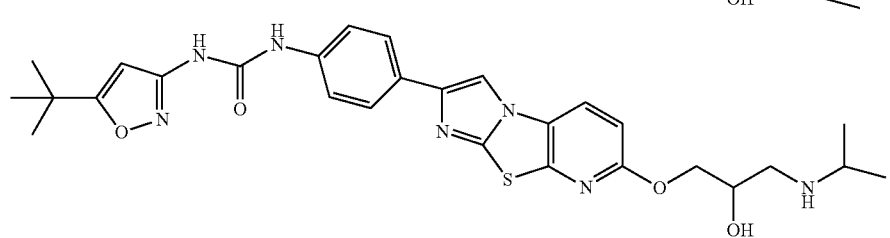
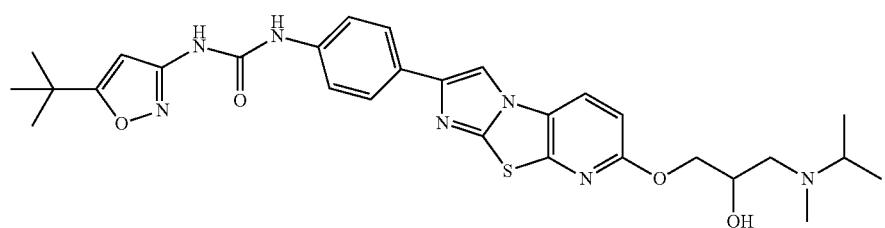
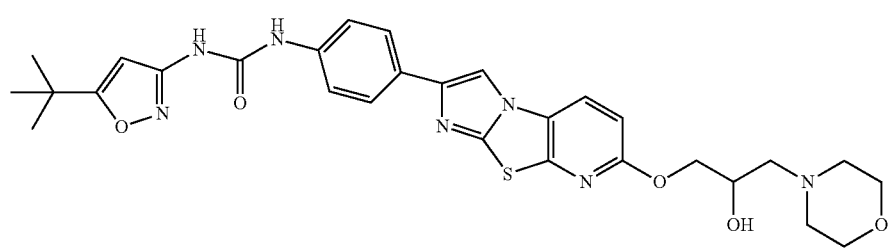

-continued
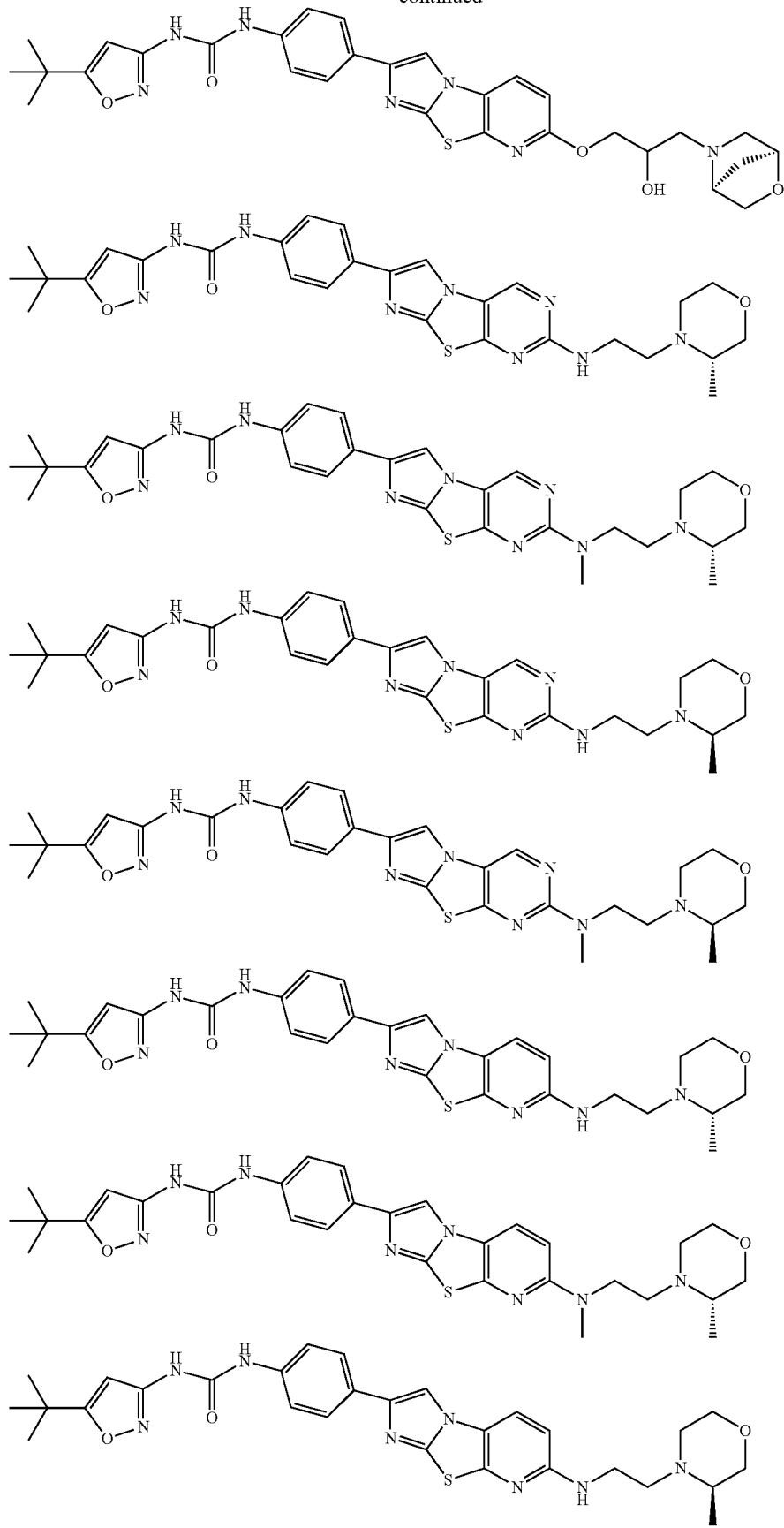

-continued
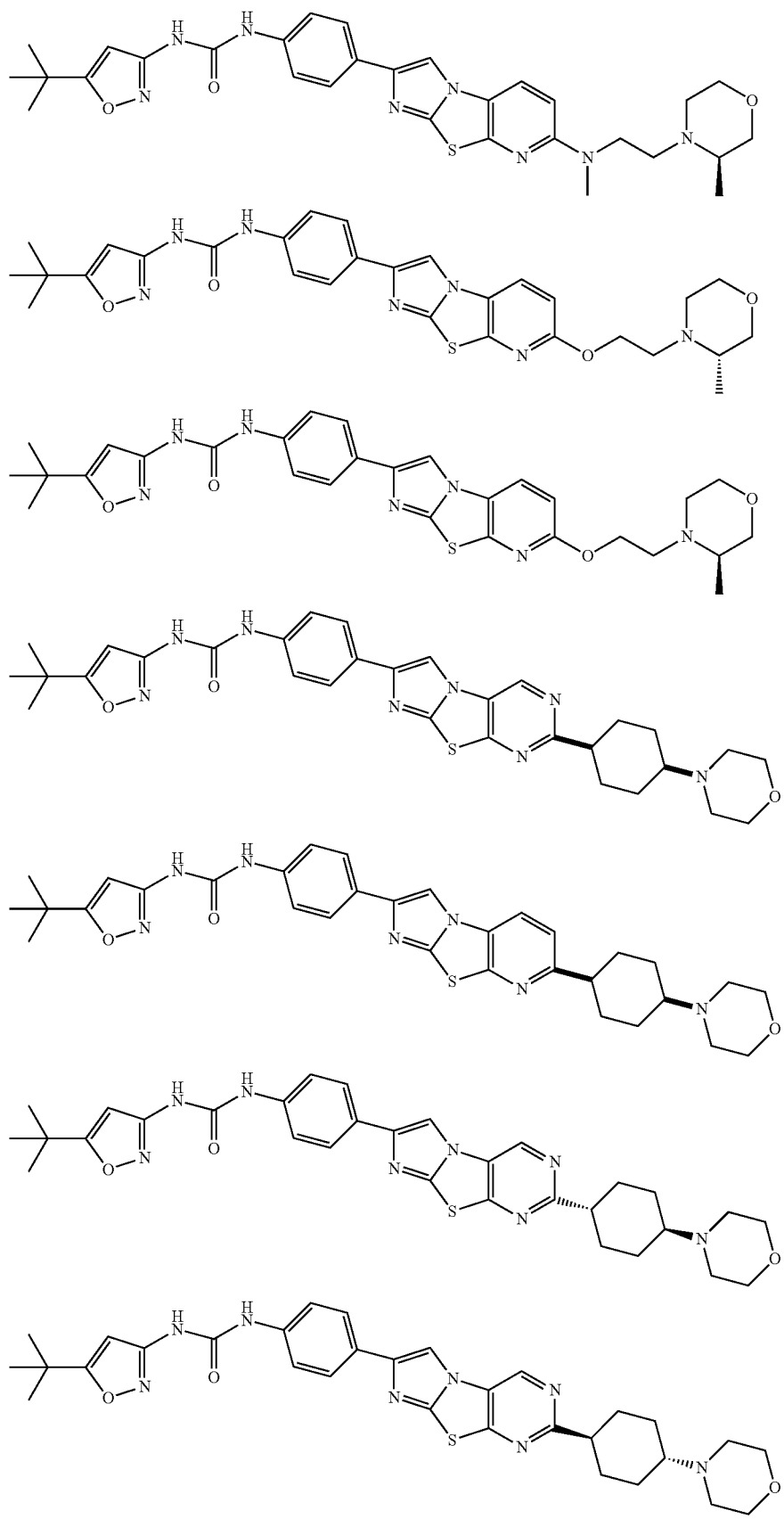

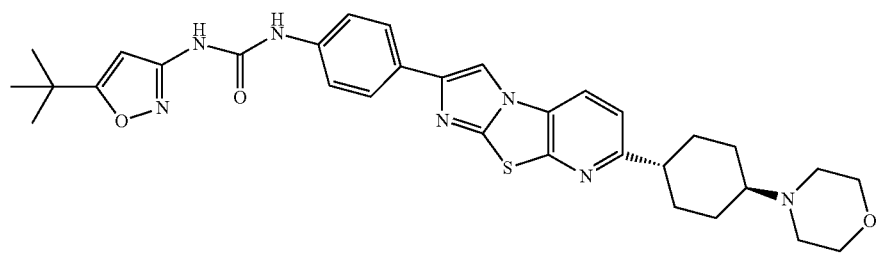
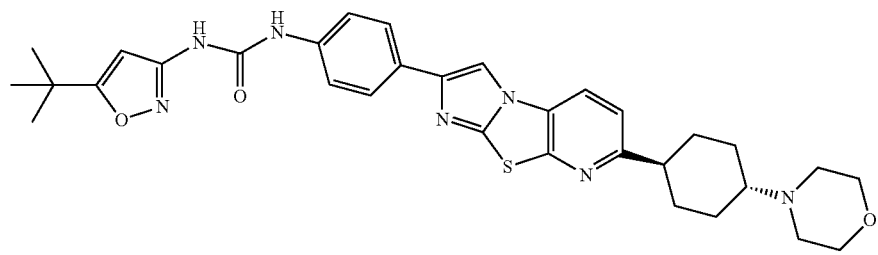
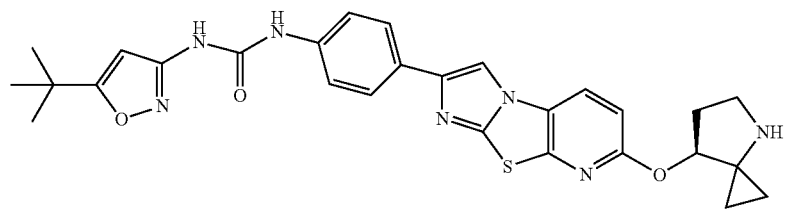
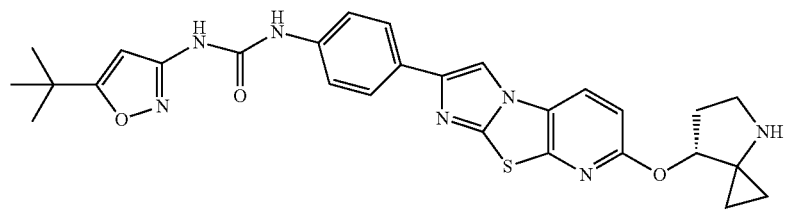
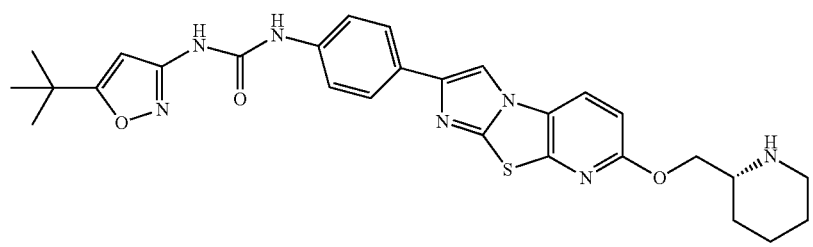
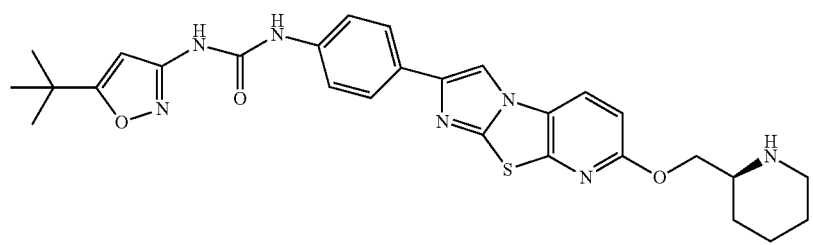
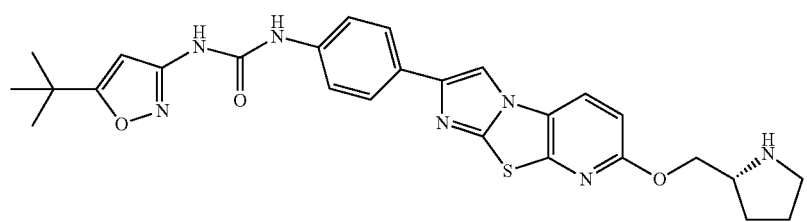

-continued

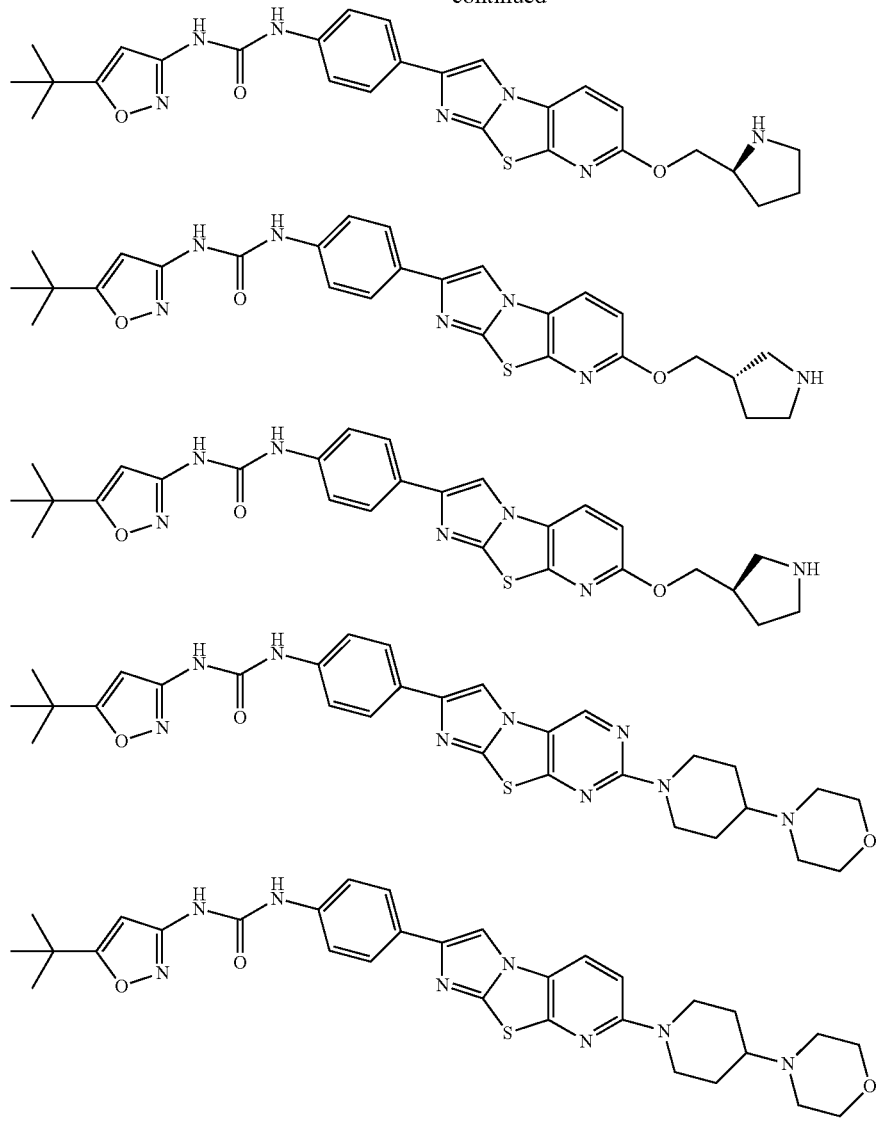

The second aspect of the present invention provides a pharmaceutical composition comprising a compound of formula (I) as defined in the above mentioned, or a pharmaceutically acceptable salt thereof, as well as a pharmaceutically acceptable carrier, adjuvant, excipient, or diluent in a therapeutically effective dose.

The third aspect of the present invention provides a compound of formula (I) or a pharmaceutically acceptable salt thereof as defined in the above mentioned for the use in preparation of a medicament as Flt3 kinase inhibitor.

The fourth aspect of the present invention provides a compound of formula (I) or a pharmaceutically acceptable salt thereof as defined in the above mentioned for the use in preparation of a medicament by modulating FLT3-mediated diseases, especially said medicament comprising administering a therapeutically effective amount of a compound of formula (I) as defined in the above mentioned, or a pharmaceutically acceptable salt thereof, as well as an isomer, a solvate, a hydrate, or a prodrug.

The fifth aspect of the present invention provides a compound of formula (I) or a pharmaceutically acceptable salt thereof as defined in the above mentioned for the use in preparation of a medicament for treating a cellular proliferative disorders diseases by inhibiting Flt3 kinase activities, wherein said diseases such as acute myeloid leukemia, chronic myeloid leukemia, myeloma, ovarian cancer, breast cancer, prostate cancer, pancreatic cancer, colorectal cancer, stomach cancer, non small cell lung cancer, thyroid cancer, brain cancer or lymphoma, said medicament comprising administering a therapeutically effective amount of a compound of formula (I) as defined in the above mentioned, or a pharmaceutically acceptable salt thereof.

the sixth aspect of the present invention provides a compound of formula (I) or a pharmaceutically acceptable salt thereof as defined in the above mentioned for the use in preparation of a medicament for treating inflammatory and autoimmune diseases by inhibiting Flt3 kinase activities, wherein said diseases such as asthma, lupus, systemic lupus, rheumatoid arthritis, multiple sclerosis, inflammatory bowel disease, or Crohn's disease, said medicament comprising administering a therapeutically effective amount of a compound of formula (I) as defined in the first aspect, or a pharmaceutically acceptable salt thereof.

DETAILED DESCRIPTION OF THE INVENTION

Unless otherwise stated, the following terms used in the specification and claims have the meanings discussed below.

Said "alkyl" refers to a saturated aliphatic hydrocarbon group including $C_1$-$C_{20}$ straight chain and branched chain groups. Preferably an alkyl group is a moderate size alkyl having $C_1$-$C_{10}$ straight chain and branched chain groups, e.g., methyl, ethyl, propyl, 2-propyl, n-butyl, iso-butyl, tert-butyl, pentyl, neopentyl, hexyl, isohexyl, heptyl, octyl, and the like. More preferably, it is a lower alkyl having $C_1$-$C_6$ straight chain and branched chain groups, e.g., methyl, ethyl, propyl, 2-propyl, n-butyl, iso-butyl, or tert-butyl, pentyl, neopentyl, hexyl, isohexyl, and the like.

Said "optionally substituted alkyl" refers to an alkyl group which may be substituted at any available point of attachment and by one to 4 substituents selected from the group consisting of halo, hydroxyl, lower alkoxy, aryl(optionally substituted with one or more groups which each independently is halo, hydroxy, lower alkyl or lower alkoxy groups), aryloxy (optionally substituted with one or more groups which each independently is halo, hydroxy, lower alkyl or lower alkoxy groups), heteroaryl(optionally substituted with one or more groups which each independently is halo, hydroxy, lower alkyl or lower alkoxy groups), heterocycloalkyl(optionally substituted with one or more groups which each independently is halo, hydroxy, lower alkyl or lower alkoxy groups), haloalkoxyl, amino, aminocarbonyl, cyano, alkynyl, carboxylic acid, or carboxylic ester.

Said "cycloalkyl" refers to a 3 to 8 membered all-carbon monocyclic ring, an all-carbon 5-membered/6-membered or 6-membered/6-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated pi-electron system. Examples of cycloalkyl groups are cyclopropyl, cyclobutyl, cyclopentyl, cyclopentenyl, chcyclohexyl, cyclohexadienyl, adamantyl, cycloheptyl, cycloheptatrienyl, and the like. The cycloalkyl group may be substituted or unsubstituted. When substituted, the substituent group(s) is preferably one or more independently selected from the group consisting of lower alkyl, trihaloalkyl, halo, hydroxy, hydroxylalkyl, aminoalkyl, amino, aryl (optionally substituted with one or more groups which each independently is halo, hydroxy, lower alkyl or lower alkoxy groups), aminocarbonyl, sulfonamido, ureido, aryloxy (optionally substituted with one or more groups which each independently is halo, hydroxy, lower alkyl or lower alkoxy groups), 6-membered heteroaryl (having 1 to 3 nitrogen atoms on the ring, the carbons on the ring being optionally substituted with one or more groups which each independently is halo, hydroxy, lower alkyl or lower alkoxy groups), 5-membered heteroaryl (having 1 to 3 heteroatoms selected from the group consisting of nitrogen, oxygen and sulfur, the carbon and nitrogen atoms of the group being optionally substituted with one or more groups which each independently is halo, hydroxy, lower alkyl or lower alkoxy groups), 5- or 6-membered heterocyclic alkyl (having 1 to 3 heteroatoms selected from the group consisting of nitrogen, oxygen and sulfur, the carbon and nitrogen (if present) atoms of the group being optionally substituted with one or more groups which each independently is halo, hydroxy, lower alkyl or lower alkoxy groups), mercapto, (lower alkyl)thio, arylthio (optionally substituted with one or more groups which each independently is halo, hydroxy, lower alkyl or lower alkoxy groups), cyano, acyl, thioacyl, O-carbamyl, N-carbamyl, O-thiocarbamyl, N-thiocarbamyl, nitro.

Said "alkenyl" refers to an alkyl group as defined above having at least 2 carbon atoms and at least one carbon-carbon double bond. Representative examples include, but are not limited to ethenyl, 1-propenyl, 2-propenyl, 1-, 2-, 3-butenyl, and the like. The optionally substituted alkenyl means the alkenyl which may be substituted with one or more groups which each independently is halo, cyano, lower alkyl or lower alkoxy groups.

Said "alkynyl" refers to an alkyl group as defined above having at least 2 carbon atoms and at least one carbon-carbon triple bond. Representative examples include, but are not limited to ethynyl, 1-propynyl, 2-propynyl, 1-, 2-, 3-butynyl, and the like. The optionally substituted alkenyl means the alkynyl which may be substituted with one or more groups which each independently is halo, cyano, lower alkyl or lower alkoxy groups.

Said "aryl (Ar)" refers to groups having at least one aromatic ring, i.e., having a conjugated pi-electron system, including all-carbon cyclic aryl, and biaryl group. Examples of aryl include phenyl, nathathyl, and the like. Said aryl group may be optionally substituted with one or more groups each independently selected from the group consisting of halo, trihalomethyl, hydroxy, hydroxylalkyl, mercapto, alkylthio, nitro, cyano, alkoxyl and alkyl.

Said "heteroaryl (Het)" refers to an aryl having 1 to 3 heteroatoms selected from the group consisting of N, O, and S as ring atoms, the remaining ring atoms being C. Said ring is 5- or 6-membered ring. The examples of heteroaryl groups include furyl, thienyl, pyridinyl, pyrrolyl, N-alkyl pyrrolyl, pyrazolyl, oxazolyl, isoxazolyl, thiazolyl, isothiazole, pyrimidinyl, pyrazinyl, imidazolyl, triazolyl, tetrazolyl, oxatriazolyl, pyridazinyl, triazinyl, oxadiazolyl, thiadiazolyl, furazanyl, and the like. Said heteroaryl group may be optionally substituted with (via a carbon of hetero atom) one or more groups each independently selected from the group consisting of halo, haloalkyl, hydroxy, hydroxylalkyl, mercapto, alkylthio, nitro, cyano, alkoxyl and alkyl.

Said "heterocycloalkyl" refers to a mono-heterocloalkyl, bi-heterocloalkyl, bridged-heteroycloalkyl or spiro-heterocycloalkyl of 4 to 12 ring atoms, wherein one, or two ring heteroatoms are selected from the group consisting of N, O, and S(O)n (n is integer from 0 to 2), the remaining ring atoms are C, in addition, the ring may also have one or more double bonds, but not have a completely conjugated pi-electron system.

Said mono heterocycloalkyl includes, but is not limited to azetidyl, pyrrolidyl, piperidyl, piperazinyl, morpholinyl, thiomorpholinyl, homopiperazinyl, and the like.

The examples of said bi-heterocycloalkyl include but not limited to

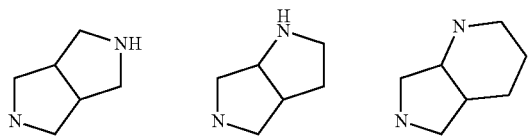

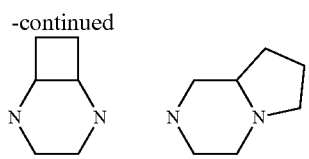

The example of said bridged-heterocycloalkyl included but not limited to

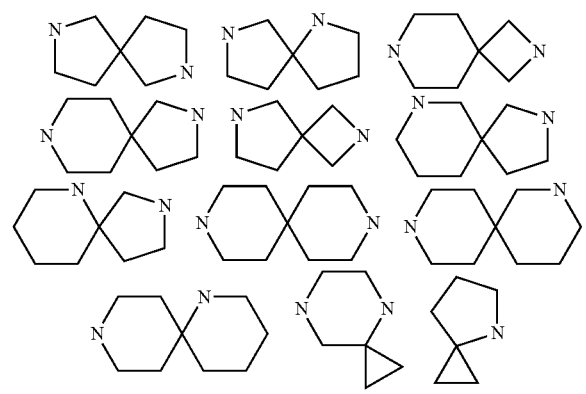

The examples of said spiro-heterocycloalkyl include but not limited to

Said "heterocycloalkyl" may be substituted or unsubstituted. When substituted, the substituent group is preferably one or more, more preferably one, two, or three, further more preferably one or two groups, each independently selected from the group consisting of lower alkyl, lower hydroxylalkyl, trihaloalkyl, halo, hydroxy, haloalkyl, mercapto, nitro, lower alkoxyl, cyano, amino, aminoalkyl, alkoxyalkyl, cycloalkyl, heterocycloalkyl, methylsulfonyl, and acyl. Said "cycloalkylalkyl" refers to a radical of the formula —RaRb, where Ra is an alkyl radical as defined above and Rb is a cycloalkyl radical as defined above. The alkyl radical and the cycloalkyl radical may be optionally substituted as defined above.

Said "arylalkyl" refers to a radical of the formula —RaRc where Ra is an alkyl radical as defined above and Rc is aryl radicals as defined above, e.g., benzyl, diphenylmethyl and the like. The alkyl radical and the aryl radical(s) may be optionally substituted as described above.

Said "Heterocycloalkylalkyl" refers to a radical of the formula —RaRd where Ra is an alkyl radical as defined above and Rd is a heterocycloalkyl radical as defined above, and if the heterocycloalkyl is a nitrogen-containing heterocycloalkyl, the heterocycloalkyl may be attached to the alkyl radical at the nitrogen atom or at carbon atom. The alkyl part of the heterocycloalkyl radical may be optionally substituted as defined above for an alkyl group. The heterocycloalkyl part of the heterocycloalkyl radical may be optionally substituted as defined above for a heterocycloalkyl group.

Said "Heteroarylalkyl" refers to a radical of the formula —RaRe where Ra is an alkyl radical as defined above and Re is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

Said "hydroxy" refers to an —OH group.

Said "alkoxyl" refers to both an —O-(alkyl) and an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

Said "amino" refers to a —NH$_2$, —NHCH$_3$, —NHCH$_2$CH$_3$, —NH-n-propyl, —NH-isopropyl, —N(CH$_3$)$_2$, —NHcyclopropyl, —NHPh, —NHpyridyl, pyrrolidinyl, piperazinyl, morpholino, piperidino, —NHalkylhydroxyl, —NHalkoxyalkyl, —NHalkylamnio, —NHcycloalkyl, —NHcycloalkylalkyl, —NHheterocycloalkyl, —NHheterocycloalkylalkyl, —NHaryl, —NHarylalkyl, —NHheteroaryl, or —NHheteroarylalkyl, etc.

Said "—NHalkylhydroxyl" refers to a —NH(alkyl)hydroxyl, wherein alkyl is as defined above. Representative examples include, but are not limited to, e.g. —NHCH$_2$CH$_2$OH, —NHCH$_2$CH(OH)CH$_2$OH, etc.

Said "—NHalkoxylalkyl" refers to a —NH(alkyl)-O-(alkyl), wherein alkyl is as defined above.

Said "—NHalkylamnio" refers to —NH(alkyl)amino, wherein alkyl and amino is as defined above. Representative examples include, but are not limited to, e.g. —NHCH$_2$CHCNH$_2$, —NHCH$_2$CH$_2$NHCH$_3$, —NHCH$_2$CH$_2$N(CH$_3$)$_2$, —NHCH$_2$CH(OH)H$_2$NH$_2$,

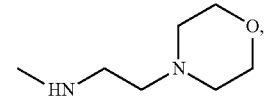

etc.

Said "—NHcycloalkyl" refers to NH-cycloalkyl, wherein cycloalkyd is as defined above.

Said "—NHcycloalkylalkyl" refers to a —NH-alkyl-cycloalkyl, wherein alkyl and cycloalkyl are as defined above. Representative examples include, but are not limited to, e.g. NH—CH$_2$-cyclopropyl-NH$_2$, NH—CH$_2$—cyclopropyl-NHCH$_3$,

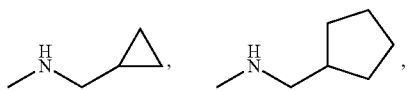

etc.

Said "—NHheterocycloalkyl" refers to NH-heterocycloalkyl, wherein heterocycloalkyl is as defined above.

Said "—NHheterocycloalkylalkyl" refers to NH-heterocycloalkyl-alkyl, wherein heterocycloalkyl and alkyl is as defined above.

Said "—NHaryl" refers to NH-aryl, wherein aryl is as defined above.

Said "—NHarylalkyl" refers to a —NH-alkyl-aryl, wherein aryl and alkyl are as defined above. Representative examples include, but are not limited to, e.g.

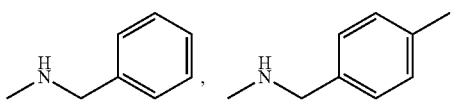

and the like.

Said "—NH heteroarylalkyl" refers to a —NH-alkyl-heteroaryl, wherein heteroaryl and alkyl are as defined above. Representative examples include, but are not limited to, e.g.

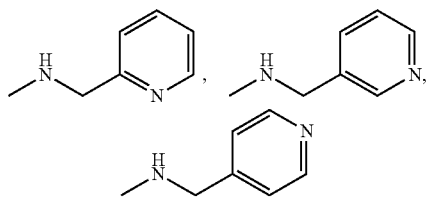

and the like.

Said "haloalkoxy" refers to an —O-(haloalkyl). Representative examples include, but are not limited to, trifluoromethoxy, trichloromethoxy, tribromomethoxy, and the like.

Said "aryloxyl" refers to both an —O-aryl and an —O-heteroaryl group, wherein the aryl and heteroaryl are as defined above. Representative examples include, but are not limited to, phenoxy, pyridinyloxy, furanyloxy, thienyloxy, pyrimidinyloxy, pyrazinyloxy, and the like, and derivatives thereof.

Said "mercapto" refers to a —SH group.

Said "alkylthio" refers to a —S-(alkyl) and a —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

Said "arylthio" refers to a —S-aryl and a —S-heteroaryl group, wherein the aryl and heteroaryl are as defined above. Representative examples include, but are not limited to, e.g., phenylthio, pyridinylthio, furanylthio, thienylthio, pyrimidinylthio, and the like, and derivatives thereof.

Said "acyl" refers to a —C(O)—$R_3$" group, where $R_3$ is selected from the group consisting of hydrogen, lower alkyl, trihalomethyl, unsubstituted cycloalkyl, aryl (optionally substituted with one or more, preferably one, two, or three substituents selected from the group consisting of lower alkyl, trihalomethyl, lower alkoxy and halo groups), heteroaryl (bonded through a ring carbon) (optionally substituted with one or more, preferably one, two, or three substitutents selected from the group consisting of lower alkyl, trihaloalkyl, lower alkoxy and halo groups), and heteroalicyclic (bonded through a ring carbon) (optionally substituted with one or more, preferably one, two, or three substituents selected from the group consisting of lower alkyl, trihaloalkyl, lower alkoxy and halo groups). Representative acyl groups include, but are not limited to, acetyl, trifluoroacetyl, benzoyl, and the like.

Said "thioacyl" refers to a —C(S)—$R_3$ group, wherein $R_3$ is as defined above.

Said "acetyl" refers to a —C(=O)$CH_3$ group.

Said "halo" refers to fluoro, chloro, bromo, or iodo, preferably fluoro or chloro.

Said "haloalkyl," refers to a $(CH_3)_2CH_2FC$—, or a $CH_3(CH_2F)_2C$—, or a $(CH_2F)_3C$— group.

Said "cyano" refers to a —C≡N group.

Said "trihaloalkyl, or trihalomethyl" refers to a $CF_3$ or the like, wherein the halo is define as above.

Said "carboxylic acid" refers to a —COOH group.

Said "carboxylic ester" refers to a —$COOR_3$ group, wherein $R_3$ is alkyl or cycloalkyl.

Said "hydroxyalkyl" refers to a -alkyl-OH group, wherein alkyl and hydroxyl as defined above. The Representative hydroxyl alkyl group include but are not limited to, —$CH_2OH$, —$CH_2CH_2OH$, $CH_3CH(OH)CH_2$—, $(CH_3)_2(CH_2OH)C$—, $CH_3(CH_2OH)_2C$—, or $(CH_2OH)_3C$—, and the like.

Said "aminoalkyl" refers to a -alkyl-amino group, wherein alkyl and amino are as defined above. The Representative aminoalkyl group include but are not limited to —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$,

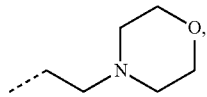

and the like.

Said "amido" refers to a —C(=O)$NR_4R_5$ which $R_4$ and $R_5$ refer to amino substituents, $R_4$ may be the same as (or may not be the same as) $R_5$, which the substituents could be hydrogen or alkyl (defined as above). Representative amido groups include, —C(=O)$NH_2$, —C(=O)$NHCH_3$, —C(=O)$N(CH_3)_2$, —C(=O)$NCH_3CH_2CH_3$, as well as the groups in which $R_4$ and $R_5$, together with the nitrogen atom to which they are attached, formed a heterocyclic ring, like morpholino, piperazinyl, piperidino, and the like.

Said "aminocarbonyl" refers to —NHC(=O)$CH_3$, —$NCH_3C$(=O)$CH_3$, —NHC(=O)$CH_2CH_3$, —$NCH_3C$(=O)$CH_2CH_3$, —NHC(=O)-cyclopropyl, —$NCH_3C$(=O)-cyclopropyl, —NHC(=O)Ph, —$NCH_3C$(=O)Ph, and the like.

Said "sulfonamido" refers to a —$NR_4S$(=O)$_2R_6$, or a —$NR_4R_5S$(=O)$_2R_6$, in which $R_4$ may be the same as (or may not be the same as) $R_5$ and $R_4R_5$ are hydrogen or alkyl, or $R_4$ and $R_5$, together with the nitrogen atom to which they are attached, form a heterocyclic ring, like morpholino, piperazinyl, piperidino and the like. $R_6$ refers to a sulfonamino substituents, for example, $C_{1-6}$ lower alkyl, $C_{3-8}$ cycloalkyl, $C_{3-20}$ heterocycloalkyl, $C_{5-20}$ aryl, and $C_{5-20}$ heteroaryl, wherein alkyl, cycloalkyl, heterocycloalkyl, aryl, and heteroaryl are as defined above. Representative sulfonamido groups include, —NHS(=O)$_2CH_3$, —$NCH_3S$(=O)$_2CH_3$, —NHS(=O)$_2$Ph, and —$NCH_3S$(=O)$_2$Ph,

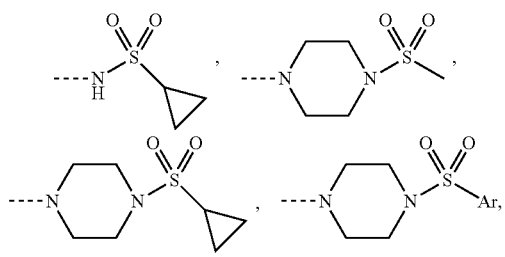

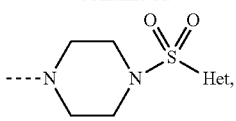

Ar and Het are as described above.

Said "ureido" refers to —NR$_3$C(O)NR$_4$R$_5$, where R$_3$ is hydrogen or alkyl; R$_4$ and R$_5$ are defined as above.

Said "methylsulfonyl" refers to CH$_3$SO$_2$—.

Said "prodrug" refers to a compound which, when metabolized in vivo, converts back to the original active compound. Typically, the prodrug is inactive, or less active than the active compound, but may provide advantageous handling, administration, or metabolic properties.

Said "optional" or "optionally" means that the subsequently described event or circumstance may or may not occur, and that the description includes instances where the event or circumstance may or may not occur. For example, "heterocyclyl optionally substituted with an alkyl group" means that the alkyl may or may not be present, and the description includes situations where the heterocyclic group is substituted with an alkyl group and situations where the heterocyclic group is not substituted with the alkyl group.

Said "pharmaceutical composition" refers to a mixture of one or more of the compounds of formula (I) as described in present invention herein, or hydrates, or solvates, or isomers, or physiologically/pharmaceutically acceptable salts or prodrugs thereof, with other chemical components, such as physiologically/pharmaceutically acceptable carriers and recipients. The purpose of a pharmaceutical composition is to facilitate administration of a compound to warm blood animals and human.

Said "exemplary compound" refers to the compound which given from the present invention, such as: the exemplary compound 8-1 is illustrated as example 1, the exemplary compound 8-2 is illustrated as example 2, and etc.

Synthesis of the Compounds of the Invention

The ureas, or cyclic forms thereof, compounds of the present invention may be synthesized by methods well known to those of skill in the art or using methods known in the art in combination with methods described herein.

Method 1:

Nitroprimidinechloride compound 1 used as a starting material, after substituted by morpholine, the nitro group was reduced by iron powder to obtain amine compound 3, condensed with compound 4 and then reduced by iron powder to get the key intermediate amine 6, which was coupled with isocyanate 7 to afford the target urea compound, as showed in scheme 1.

Scheme-1

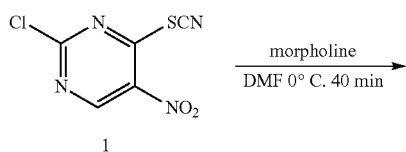

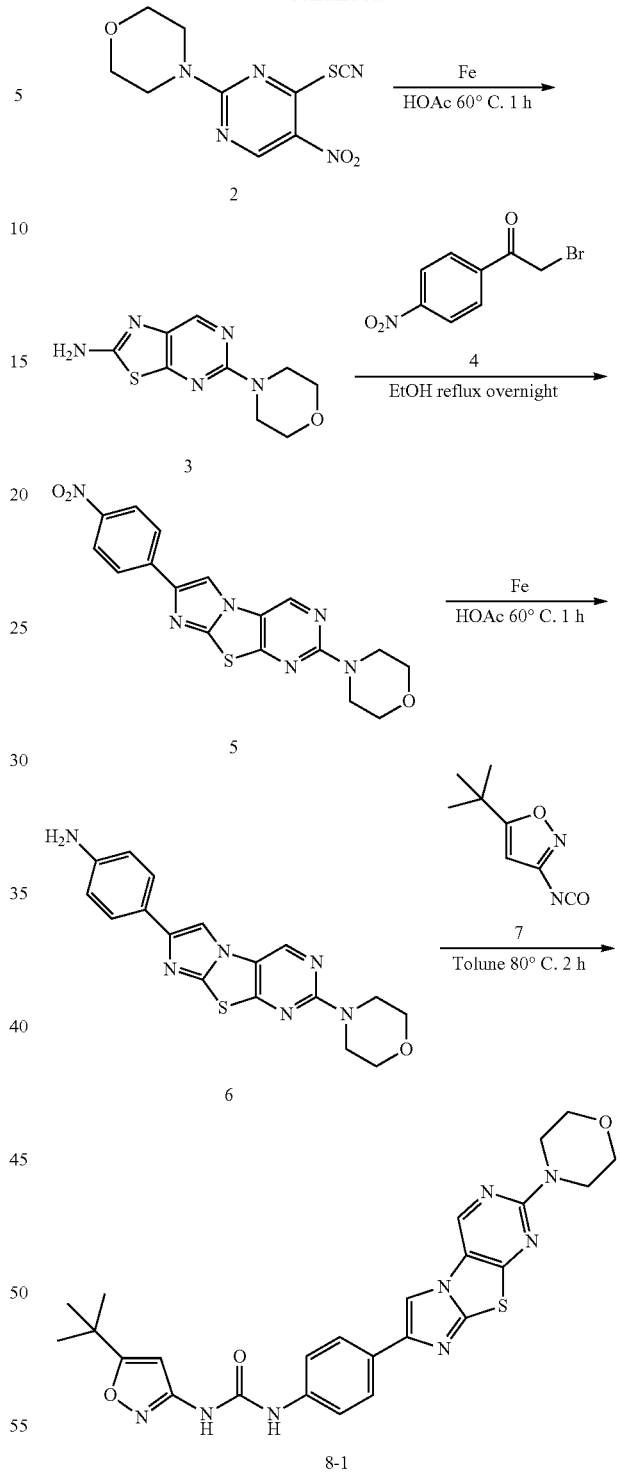

Method 2:

Compound 9 used as a starting material, the thiazole ring was opened by basic hydrolysis, then re-closed by acetyl chloride to get intermediate 12. After compound 12 was condensed with compound 4 to obtain the nitro compound 14, de-methylation by HBr to get the phenol intermediate 15, alkylated the phenol group by chloride compound 16, and the nitro compound 17 was reduced into amine 18 by iron powder, the target urea compound was obtained by reacting 18 with isocyanate 7, as showed in scheme 2.

Scheme-2
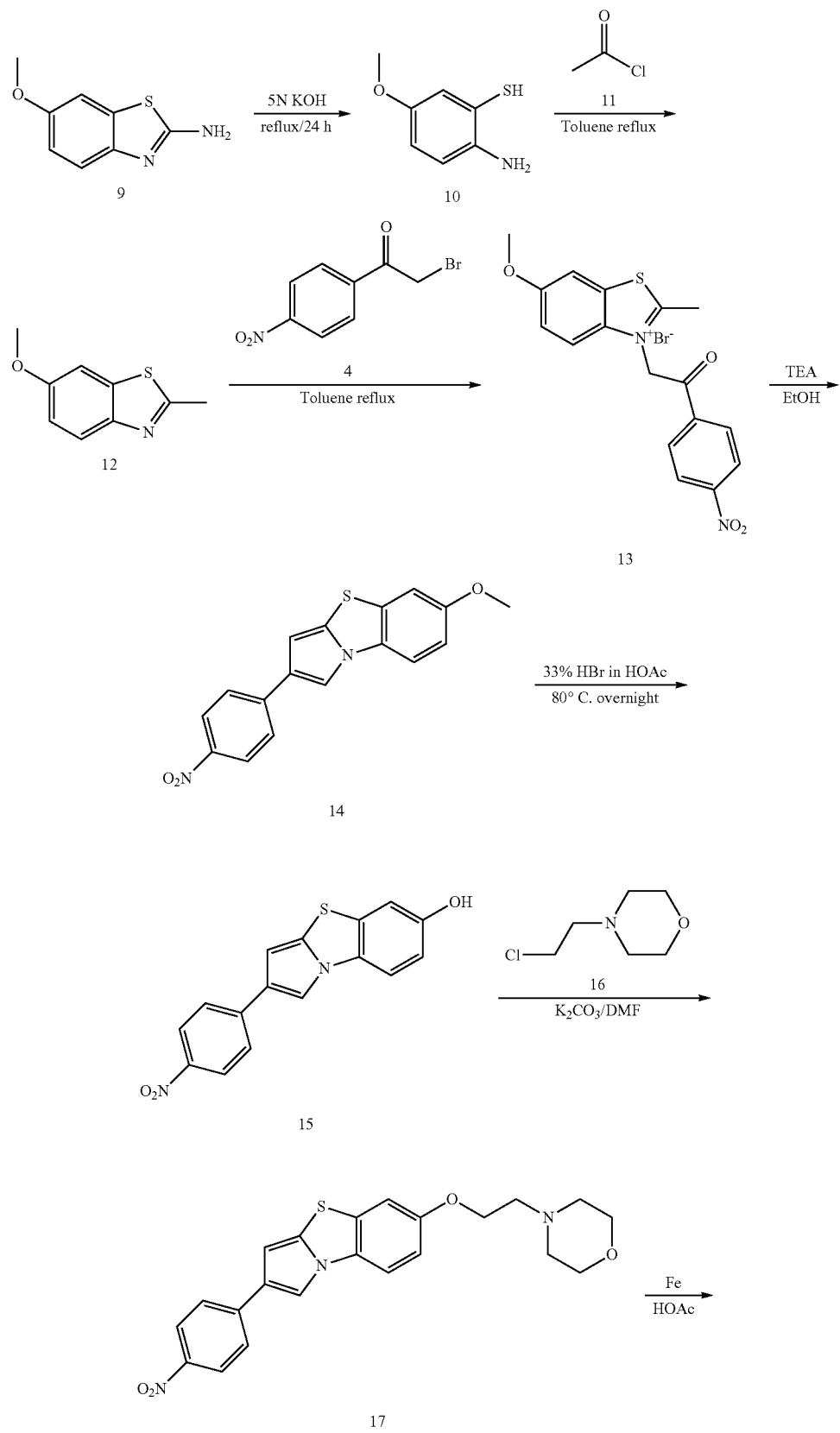

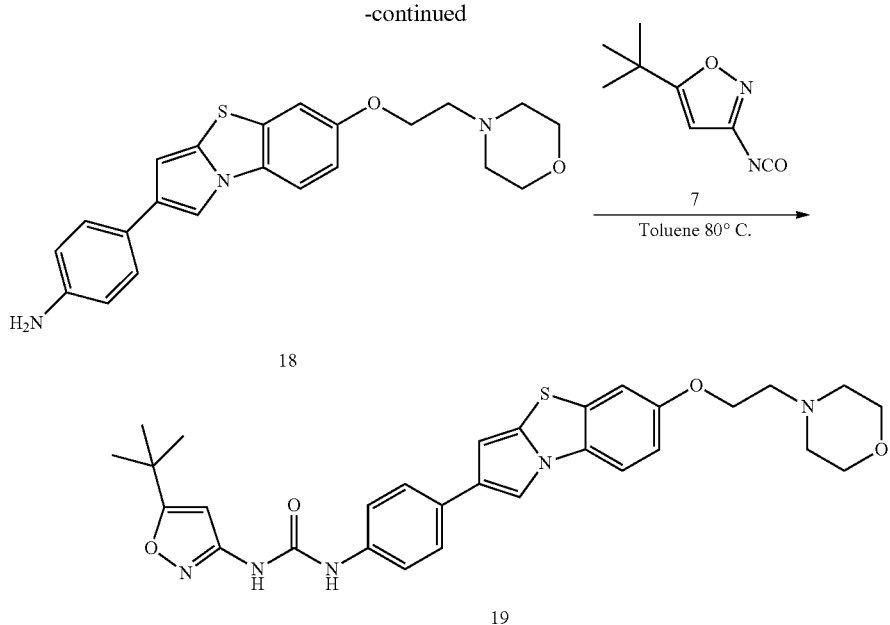

Method 3:

Chloronitropyridine 20 was used as starting material, after methoxylation, reduced nitro 21 into amine 22 by iron powder, then was converted into amniothiazole 23, demethylation to obtain phenol 24, condensed with compound 4 to obtain tricyclic nitro compound 25, after reacted with chloride 16, reduced nitro into amine 27 by iron powder, the final target urea compound was obtained by reacting 27 with isocyanate 7 as showed in scheme 3-A.

The other invented compounds could be made by from scheme 3-B to scheme 3-I.

Scheme 3-A

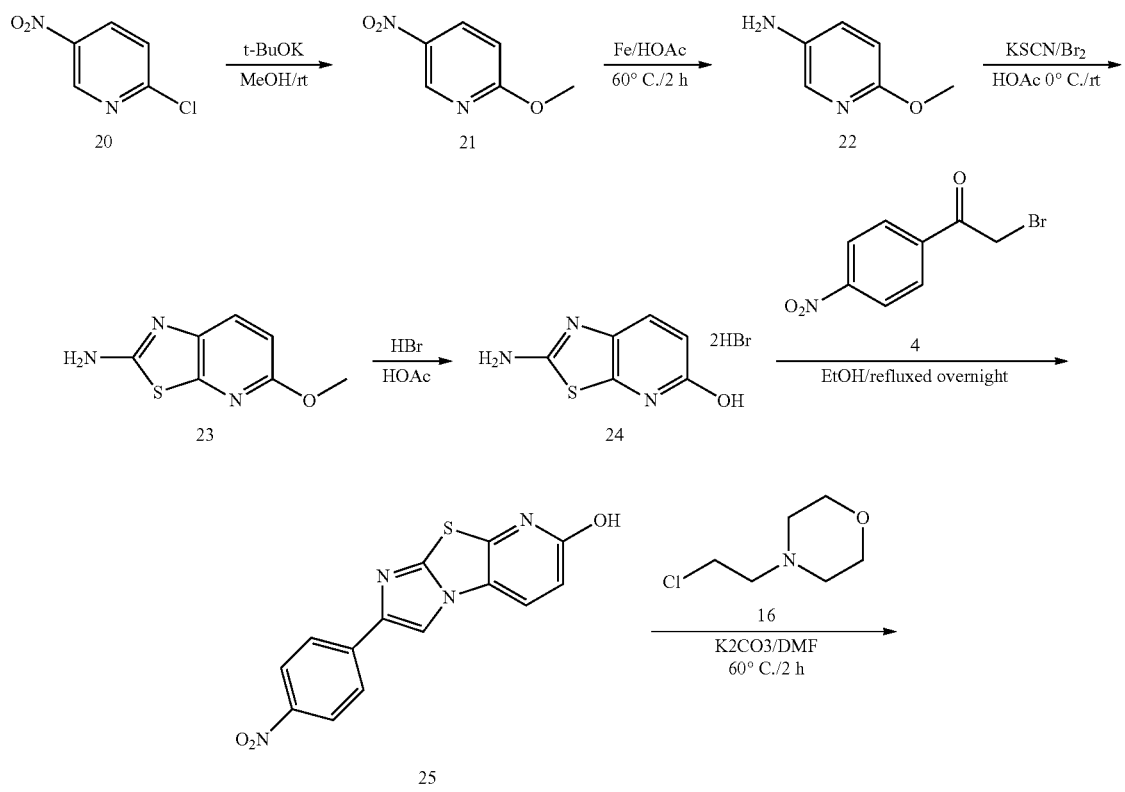

-continued
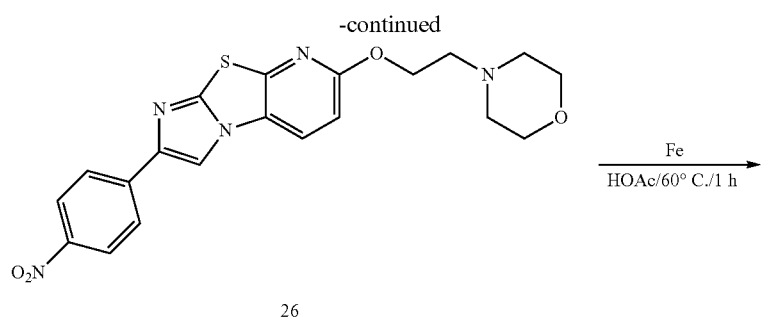
26
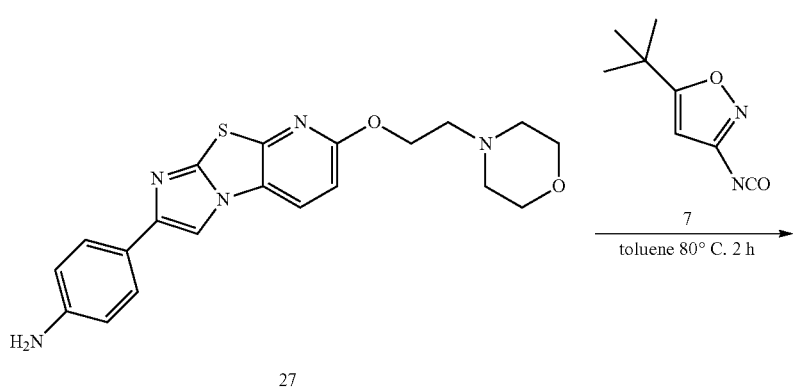
27
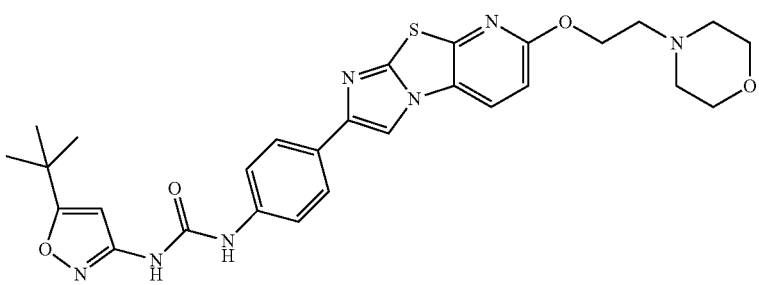
28-1
Scheme 3-B
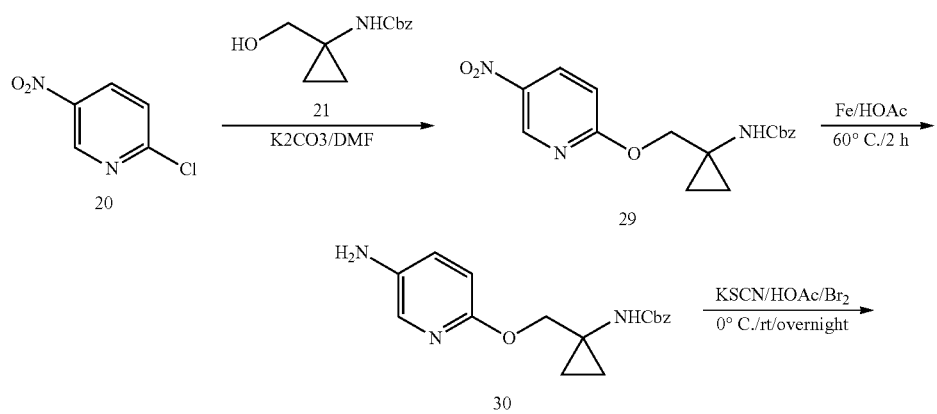

-continued
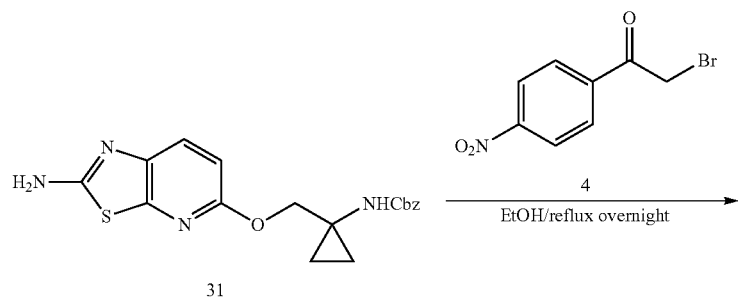
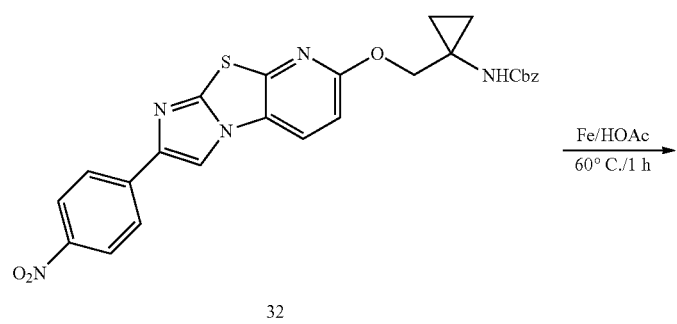
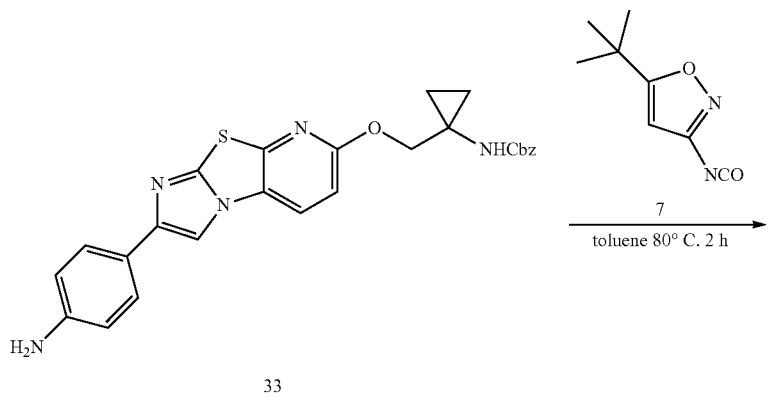
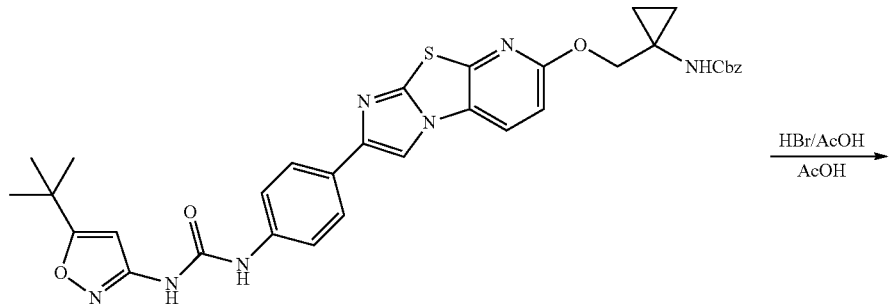

-continued
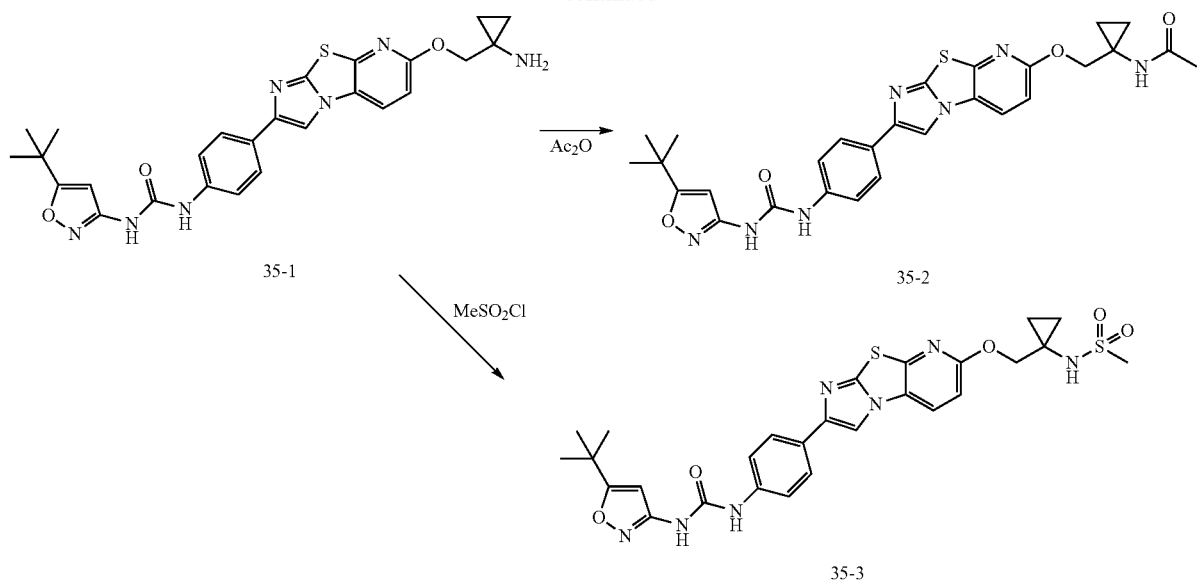
Scheme 3-C
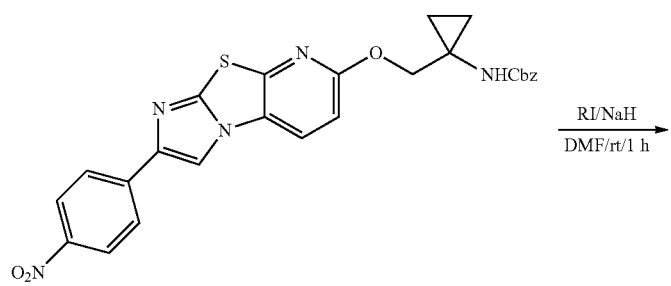
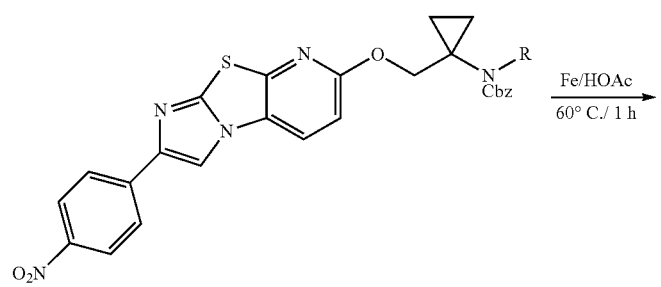
Re = Me, 36-1
= Et, 36-2
= n-Pr, 36-3

-continued
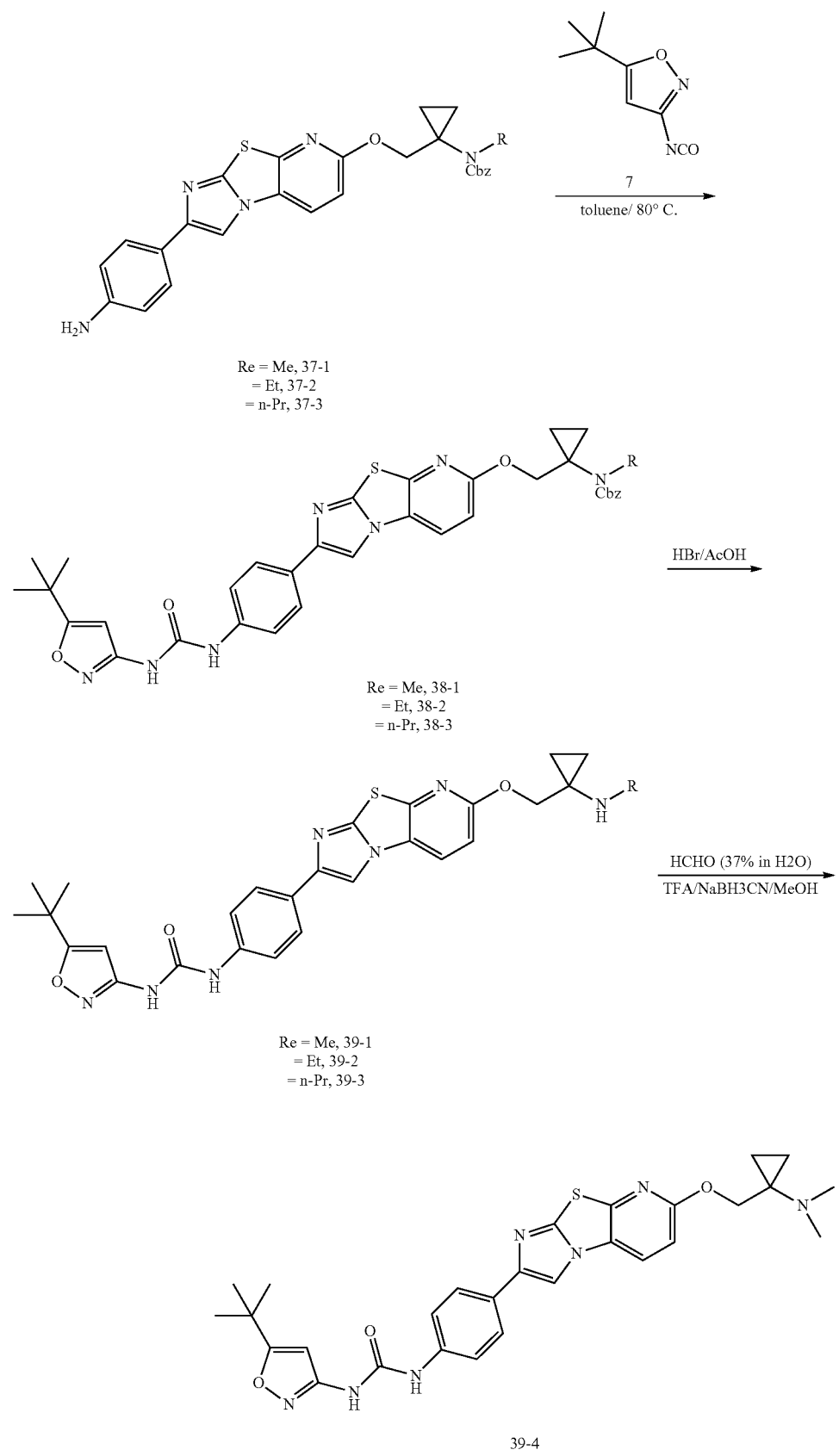

Scheme 3-D
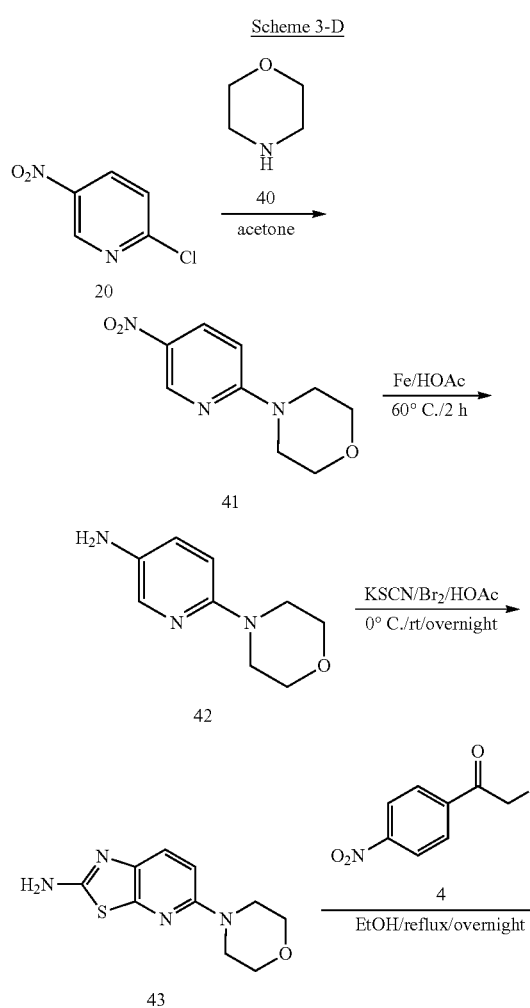
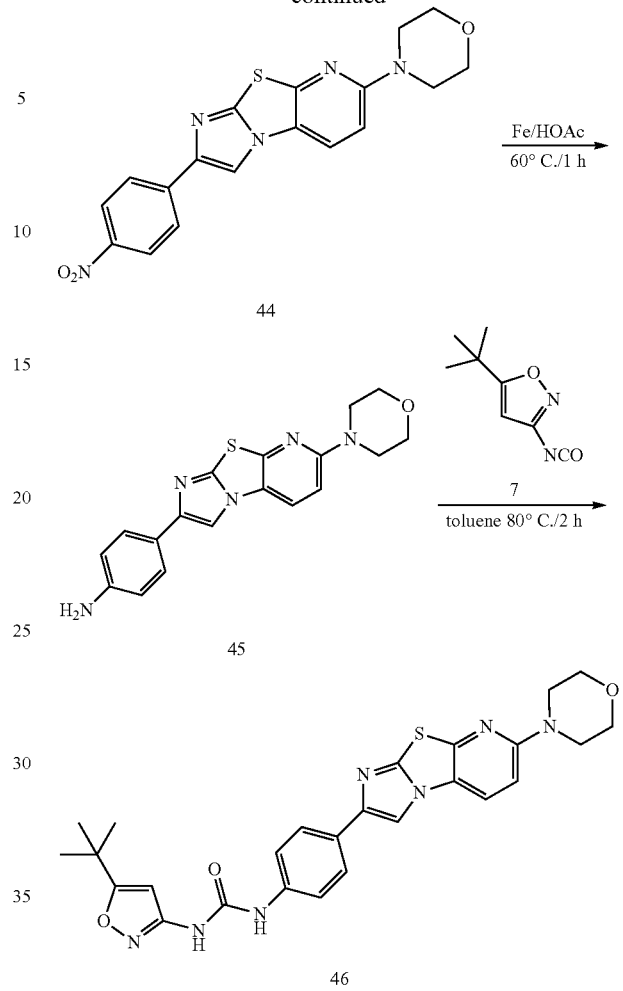
Scheme 3-E
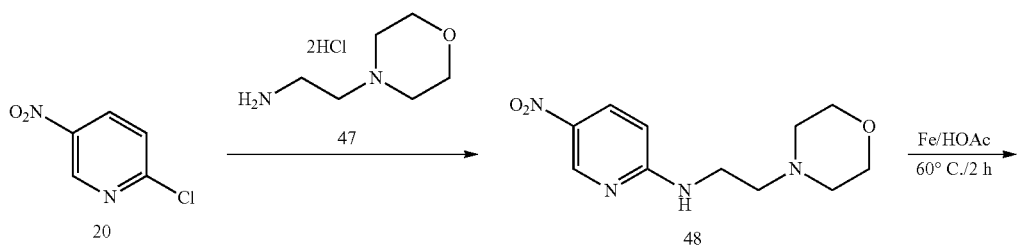
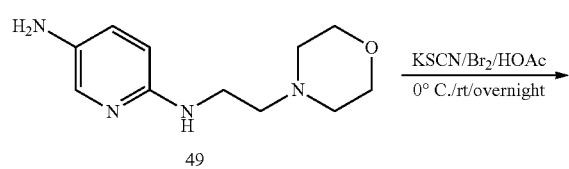

-continued
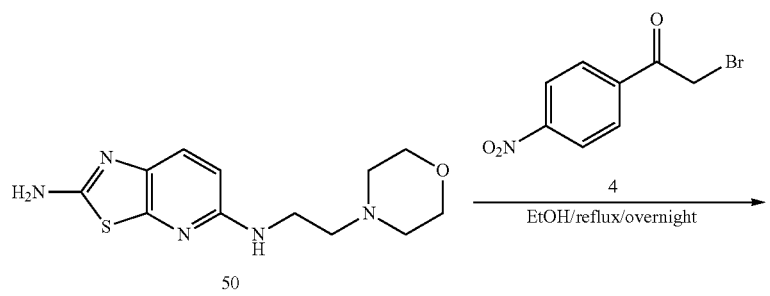
50
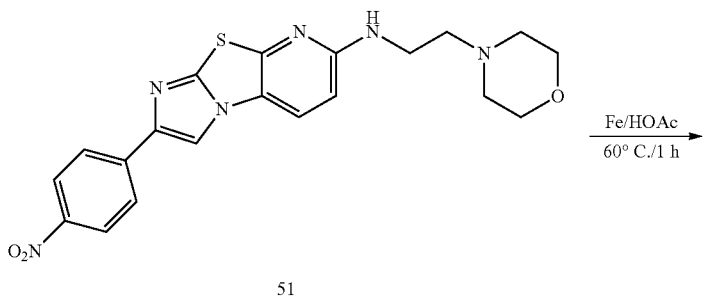
51
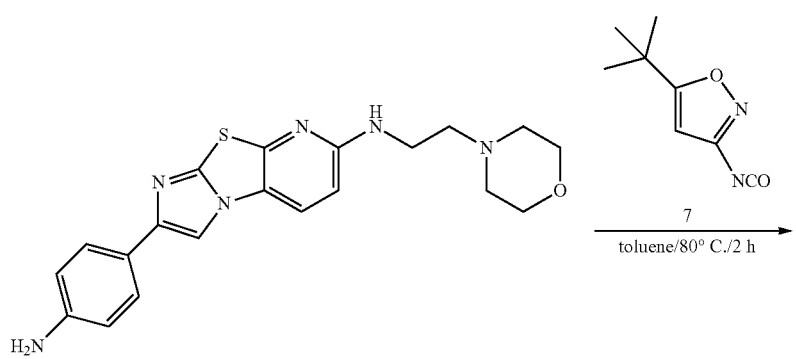
52
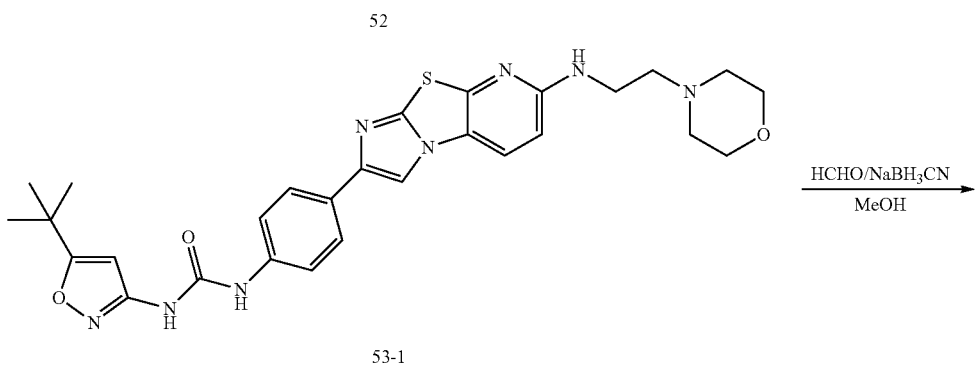
53-1
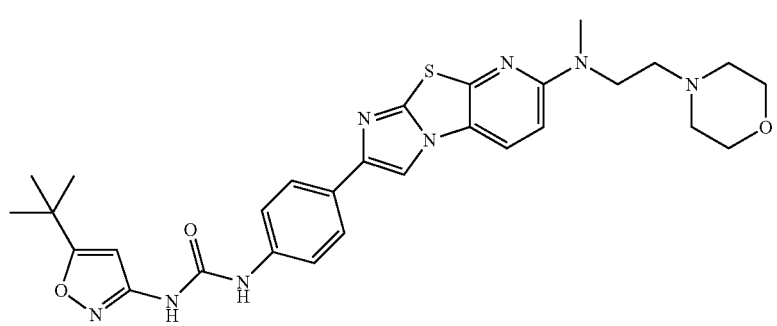
53-2

Scheme 3-F
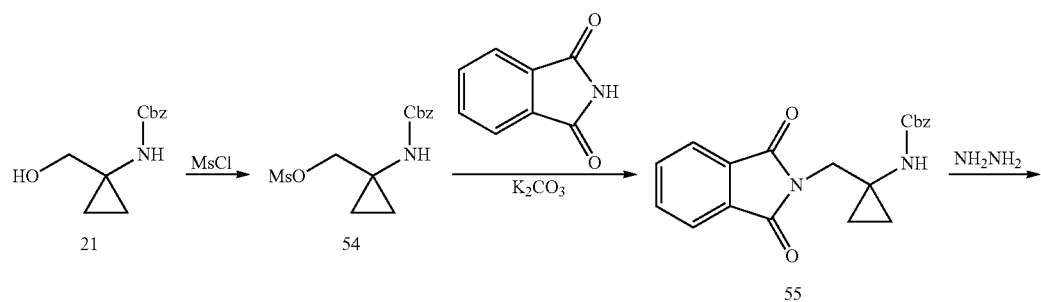
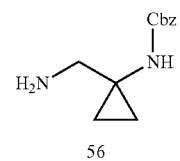
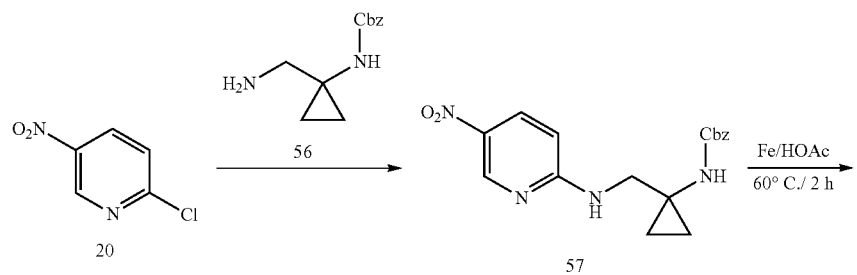
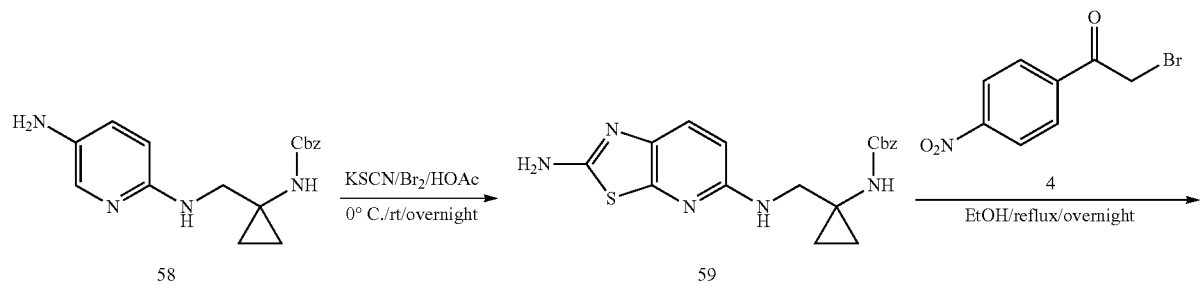
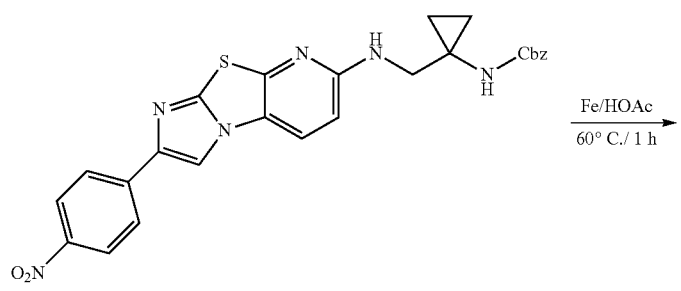

-continued
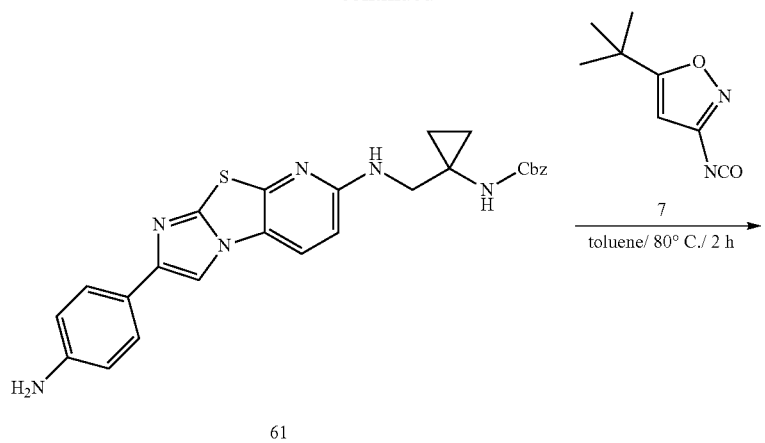
61
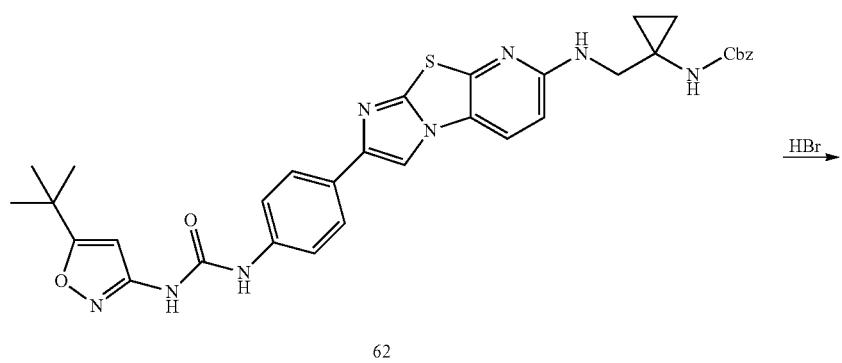
62
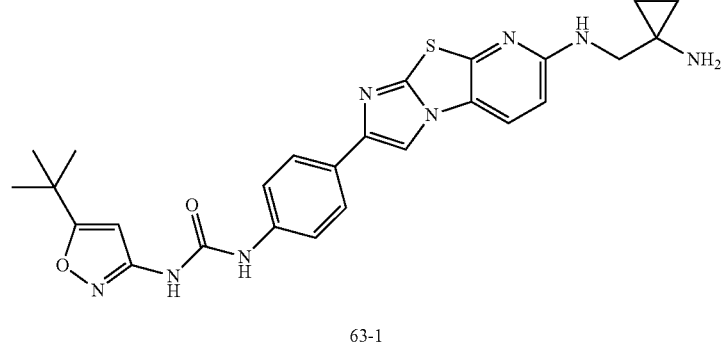
63-1
Scheme 3-G
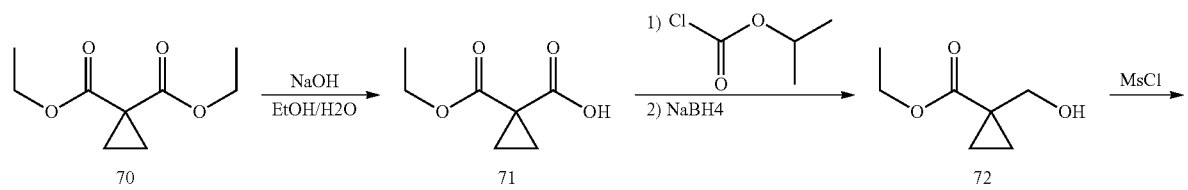

-continued
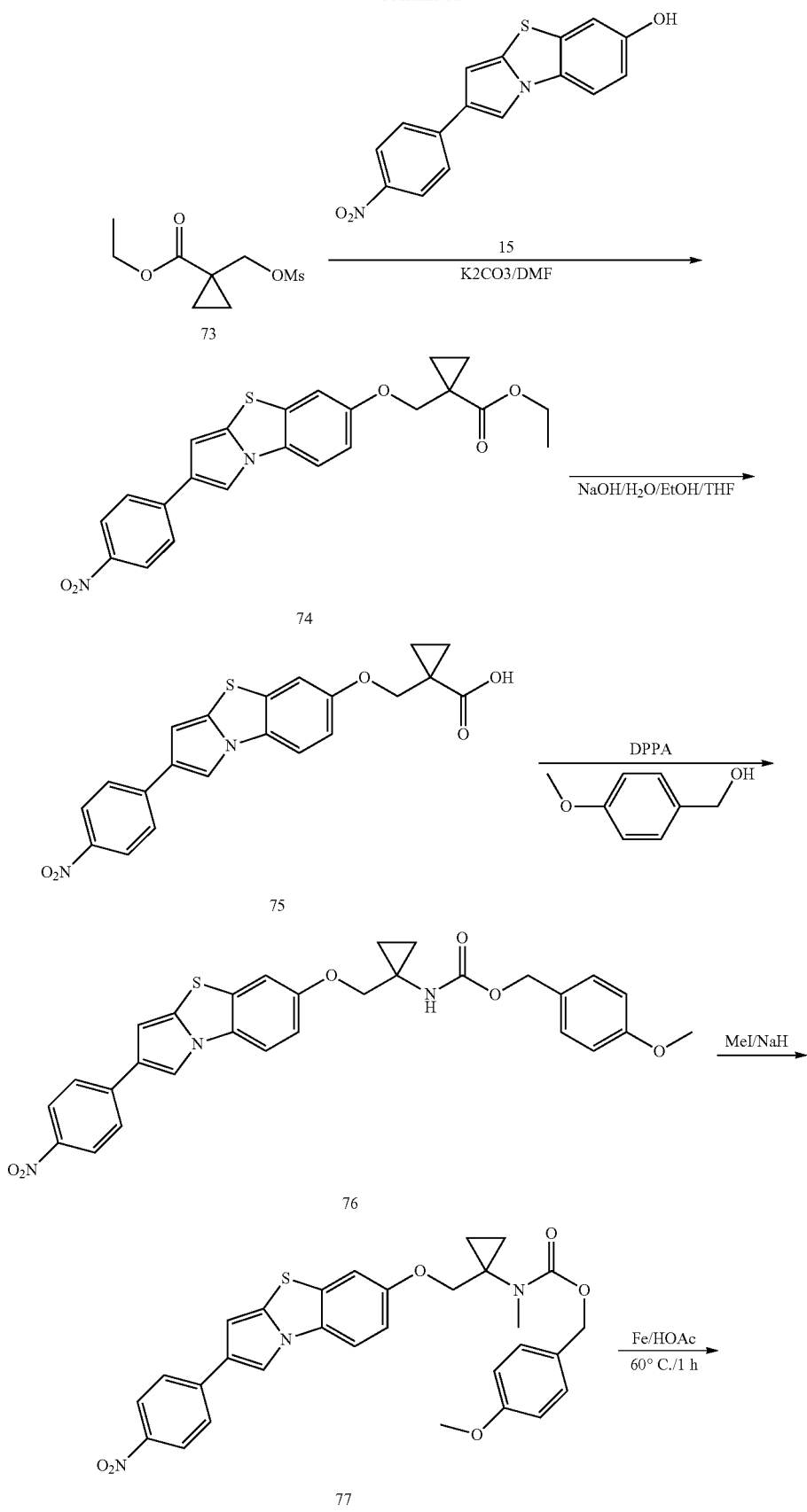

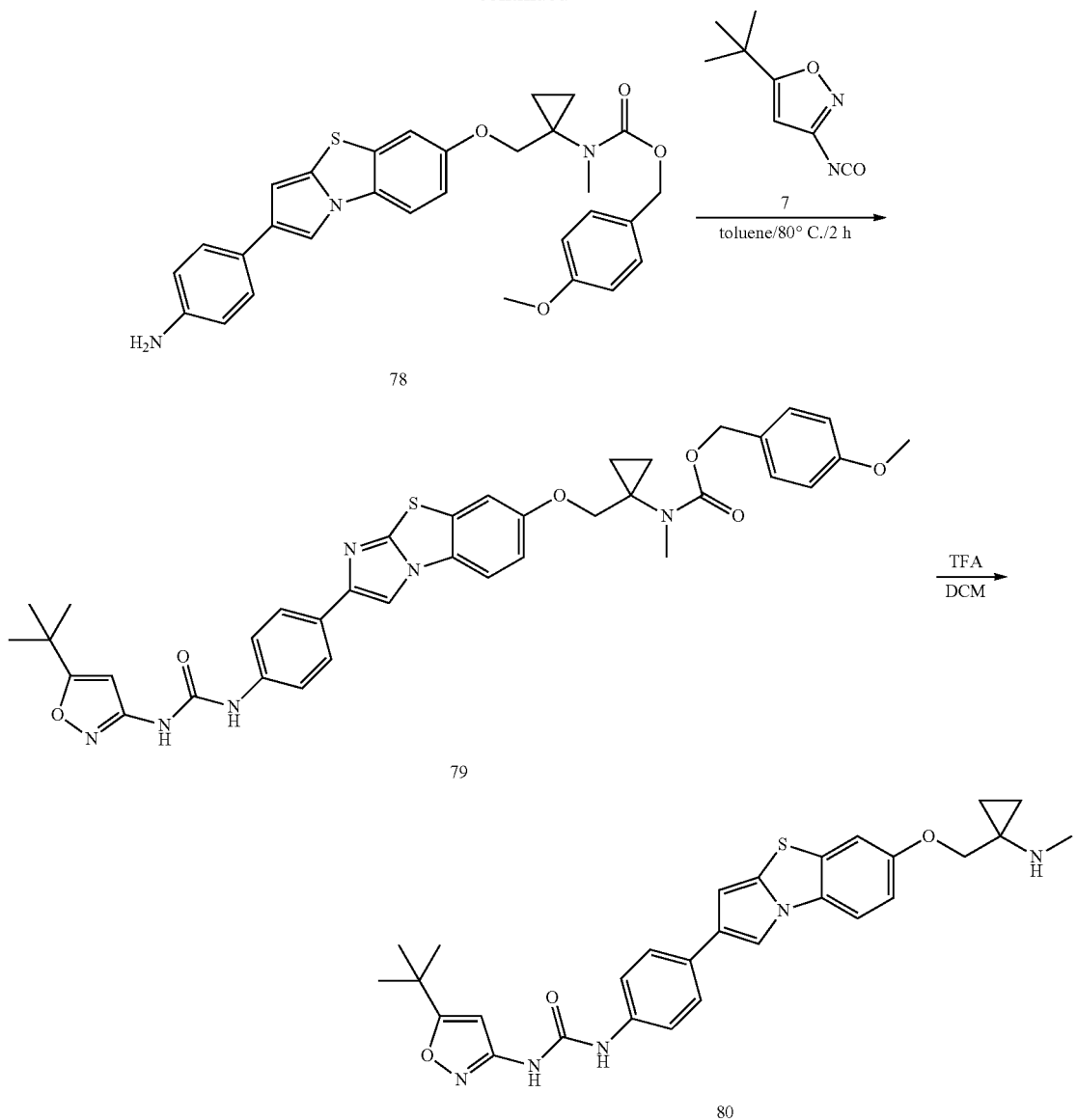
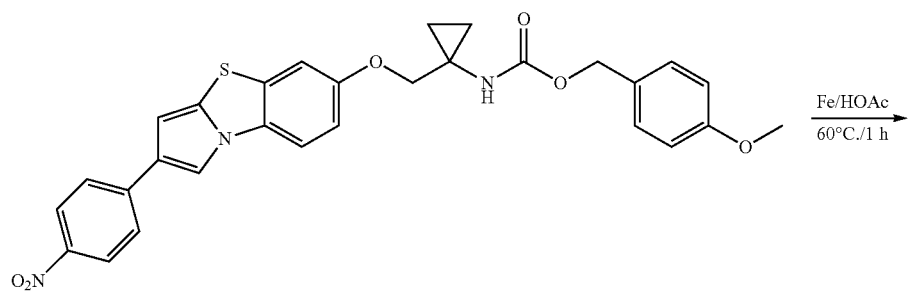
Scheme 3-H

-continued
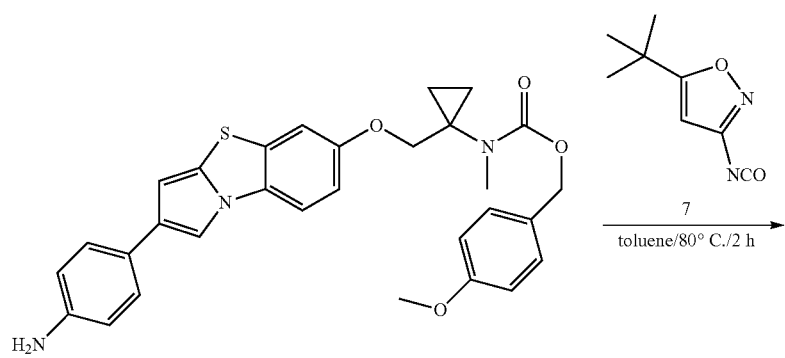
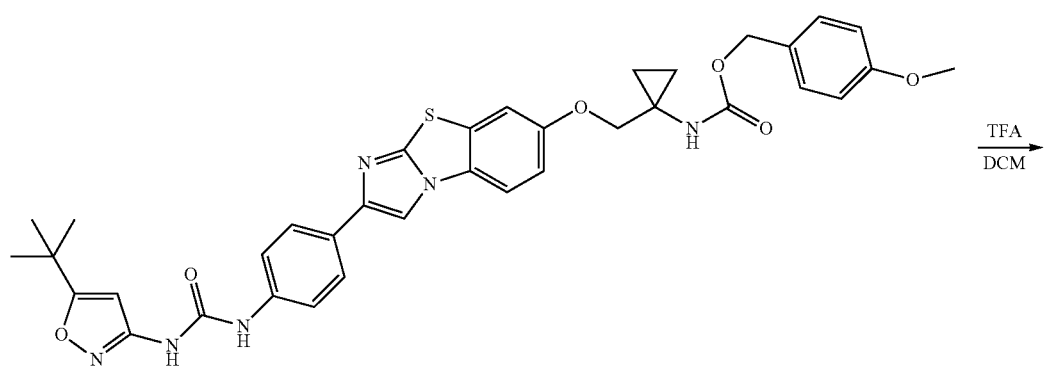
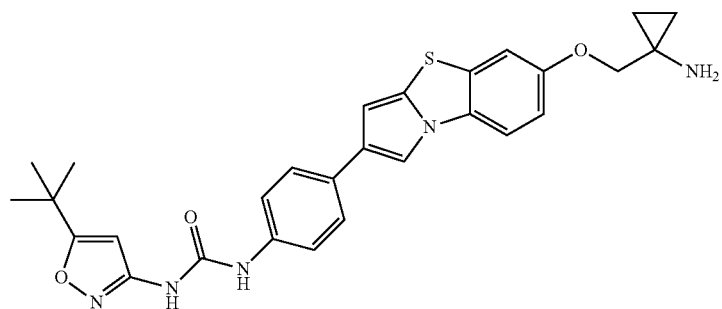
Scheme 3-I
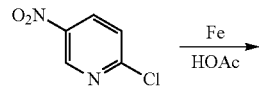

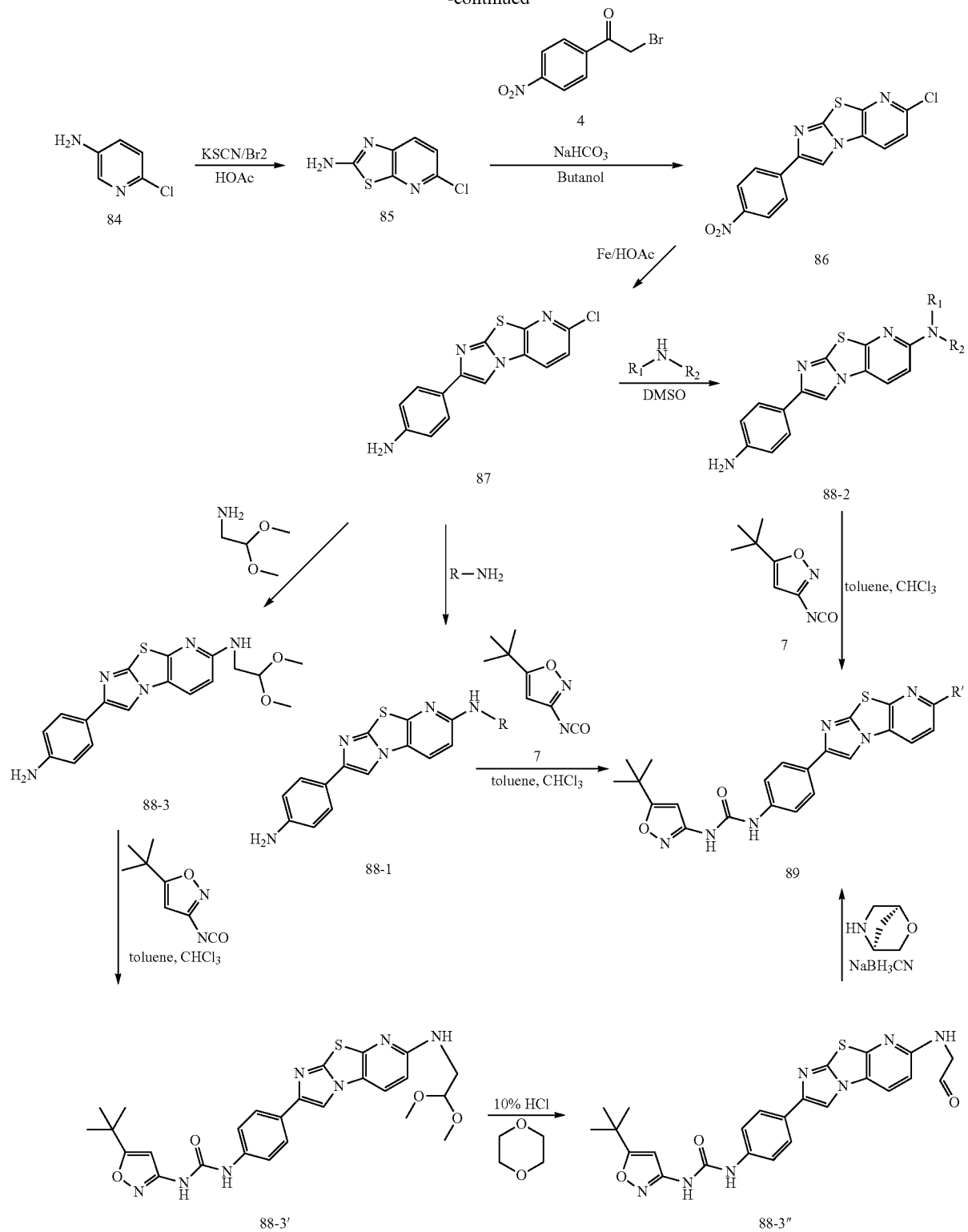

Method 4:
Nitroprimidinechloride compound 1 used as a starting material, after substituted by 2,2-dimethoxyethanamine 91, then reduced the nitro 91 by iron powder to obtain amine compound 92, the compound 92 was then condensed with compound 4, followed by the reduction of nitro group with zinc powder into amine 94, coupled with isocyanate 7 to form urea intermediate 95, and acid hydrolysis acetal into aldehyde 96 which was finally formed different 97 series compounds by reduction amination with different amines, as showed in scheme 4-A.

Scheme 4-A
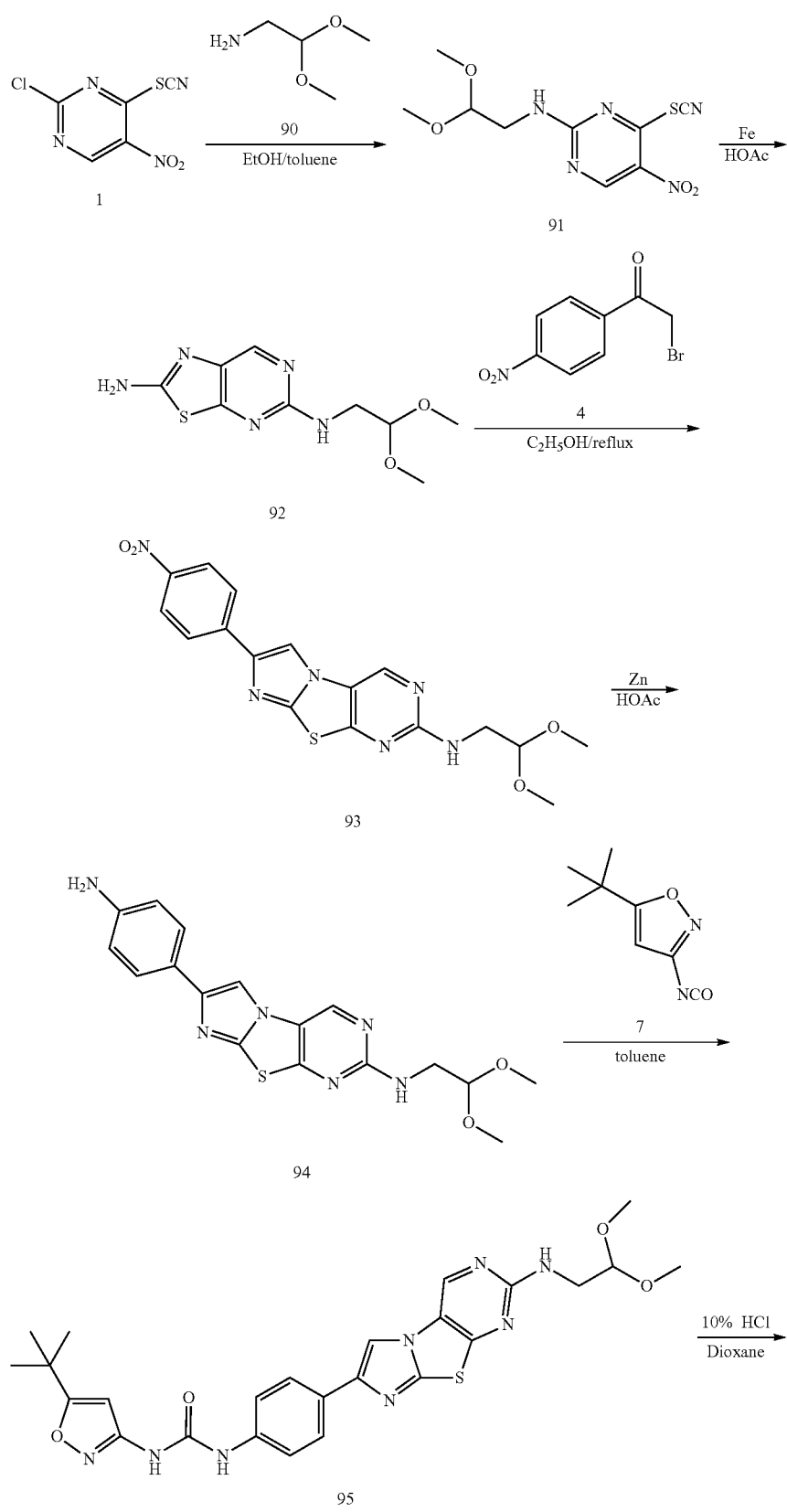

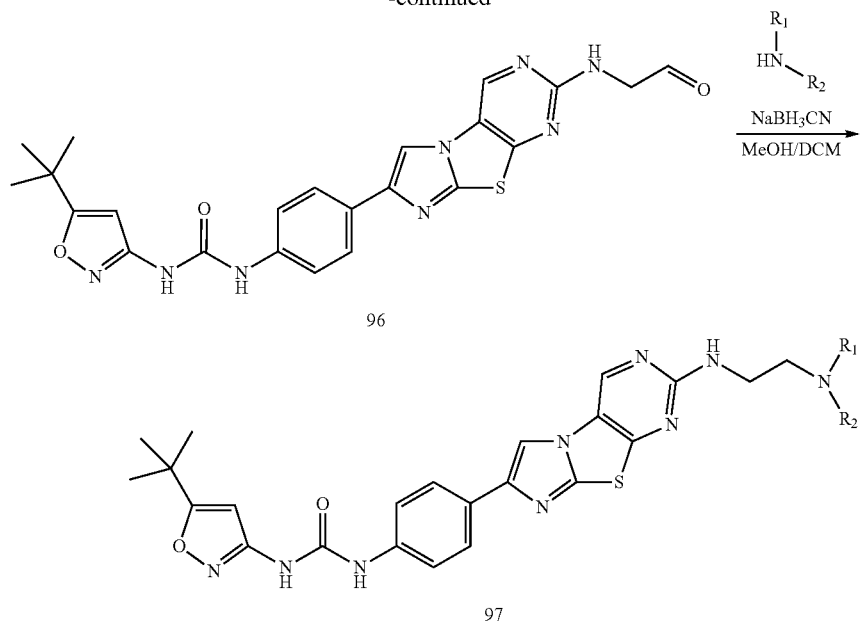

The ureas may be converted to thioureas by treating with Lawesson's reagent in the presence of toluene.

The term "protecting group Cbz" (see scheme 3-B, 3-C, 3-F) refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis.

The present invention also relates to a compounds of formula (I) or a pharmaceutically acceptable salt thereof, wherein a compound of formula (I) may be present in the form of free base or in the form of salts formed by acid addition which are pharmaceutically acceptable non-toxic. The pharmaceutically acceptable salts include hydrochloride, p-toluenesulfonate, benzenesulfonate, naphthalenesulfonate, tartarate, maleate, lactate, methanesulfonate, ethanesulfonate, sulfate, phosphate, citrate, acetate and trifluoroacetate, preferably p-toluenesulfonate, benzenesulfonate, methanesulfonate, hydrochloride, tartarate and trifluoroacetate.

Furthermore, the present invention relates to a pharmaceutical composition comprising a compound of formula (I) or a pharmaceutically acceptable salt thereof in an effective therapeutic dose, and a pharmaceutically acceptable carrier, and a use of the compounds of the present disclosure or pharmaceutical acceptable salts in the preparation of a medicament as a kinase inhibitor. In other words, this disclosure also provides a pharmaceutical composition comprising the above mentioned compounds in an effective therapeutic dose, as well as their use in the preparation of a medicament as Flt3 inhibitor.

The compounds of the present invention are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula (I) include conventional non-toxic salts or quarternary ammonium salts of the compounds of formula (I) formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glyeolic, stearic, lactic, malic, tartaric, citric, ascorbic, pamoic, sulfanilic, 2-acetoxybenzoic, fumaric, naphthalenesulfonic, toluenesulfonic, benzenesulfonic, ethanesulfonic, methanesulfonic, ethane disulfonic, oxalic, isethionic, trifluoroacetic and the like.

The pharmaceutically acceptable salts of the present invention can be synthesized by conventional chemical methods.

Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomer. All such isomers including optical, enantiomeric, diasteriomeric, stereoisomeric, epimeric, and geometric isomers are included in the present invention.

The compounds of the present invention may be in crystalline or non-crystalline form, it may exist in a number of different polymorphic forms, and may optionally be hydrated or solvated. This invention includes within its scope stoichiometric hydrates as well as compounds containing variable amount of water.

The present invention described herein also includes a pharmaceutical composition comprising a therapeutically effective amount of compound of formula (I) or a pharmaceutically acceptable salt thereof, a pharmaceutically acceptable carrier in the use of preparation of a medicament as kinase inhibitors.

Compounds provided herein are useful in treating conditions characterized by inappropriate FLT3 activity such as proliferative disorders. FLT3 activity includes, but is not limited to, enhanced FLT3 activity resulting from increased or de novo expression of FLT3 in cells, increased FLT3 expression or activity, and FLT3 mutations resulting in constitutive activation. The existence of inappropriate or abnormal FLT3 ligand and FLT3 levels or activity can be determined using well known methods in the art. For example, abnormally high FLT3 levels can be determined using commercially available ELISA kits. FLT3 levels can be determined using flow cytometric analysis, immunohistochemical analysis, and in situ hybridization techniques.

An inappropriate activation of the FLT3 can be determined by an increase in one or more of the activities occurring subsequent to FLT3 binding: (1) phosphorylation or autophosphorylation of FLT3; (2) phosphorylation of a FLT3 substrate, e.g., Stat5, Ras; (3) activation of an related complex, e.g., PI3K; (4) activation of an adaptor molecule; and (5) cellular proliferation. These activities are readily measured by well known methods in the art.

A compound of formula (I) disclosed herein would be useful for, but not limited to, the prevention or treatment of proliferative diseases, conditions, or disorders in a patient by administering to the patient a compound of formula (I) or a composition comprising a compound of formula (I) disclosed herein in an effective amount. Such diseases, conditions, or disorders include cancer, particularly hematopoietic cancer, metastatic cancer, atherosclerosis, and lung fibrosis.

Compounds disclosed herein would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment FLT3-mediated and/or CSF-1R mediated diseases like immune dysfunction, autoimmune diseases, kidney diseases, tissue transplant rejection, lupus erythematosis, multiple sclerosis, inflammatory bowel disease, rheumatoid arthritis, arthritis, asthma.

The compounds disclosed herein are also useful in the treatment of diabetic conditions such as diabetic retinopathy and microangiopathy.

The compounds disclosed herein are also useful in the reduction of blood flow in a tumor in a subject.

The compounds disclosed herein are also useful in the reduction of metastasis of a tumor in a subject.

Besides being useful for human treatment, these compounds are also useful for veterinary treatment of companion animals, exotic animals and farm animals, including mammals, rodents, and the like. In other embodiments, animals include horses, dogs, and cats. As used herein, the compounds of formula (I) disclosed herein include the pharmaceutically acceptable derivatives thereof.

Where the plural form is used for compounds, salts, and the like, this is taken to refer to also a single compound, salt, and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses VEGFR, or c-Met, that includes contacting the cell with a compound or composition disclosed herein, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention also provided herein a method of inhibiting VEGFR, and/or c-Met kinase activity in a biological sample that includes contacting the biological sample with a compound or composition disclosed herein. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly VEGFR or c-Met kinase activity, in a biological sample is useful for a variety of purposes known to one of skill in the art. Examples of such purposes include, but are not limited to, blood transfusion, organ-transplantation, biological specimen storage, and biological assays.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

When administered to a patient for the treatment of cancer, the dosage used can be varied depending upon the type of cancer, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering a compound of formula (I) orally or parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula (I) may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula (I) and a pharmaceutically acceptable carrier. The compounds of formula (I) may also be included in pharmaceutical compositions in combination with a second therapeutically active compound. The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen. Similarly, the carrier or diluent may include time delay material well known in the art, such as glyceryl monostearate or glycerol distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution. Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like. The amount of a compound of formula (I) used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

he active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, com, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Suitable coatings and the general preparation of coated implantable devices are described in U.S. Pat. Nos. 6,099, 562, 5,886,026 and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound disclosed herein are another embodiment disclosed herein. The compounds may also be coated on implantable medical devices, such as beads, or co-formulated with a polymer or other molecule, to provide a "drug depot" thus permitting the drug to be released over a longer time period than administration of an aqueous solution of the drug.

BRIEF DESCRIPTION OF THE DRAWING

FIG. 1 is demonstrated the antitumor effect on MV4-11 acute myeloid leukemia zenograft tumor model of the exemplary compound of the present invention. A (solvent) is used as a negative control group, B (Quizartinib) is used as a positive control group, and C (the exemplary compound of the present invention) is used in tested group.

EXAMPLES

The following examples serve to illustrate the compounds in this invention and the preparation process, but the examples should not be considered as limiting the scope of the invention.

The structures of all compounds were identified by nuclear magnetic resonance ($^1$H NMR) and mass spectrometry (MS). $^1$H NMR chemical shifts ($\delta$) were recorded in ppm ($10^{-6}$). NMR was performed on a Bruker AVANCE-400 spectrometer. The suitable solvents were deuterated-chloroform (CDCl$_3$), deuterated-dimethyl sulfoxide (DMSO-d$_6$) and deuterated-methanol (CD$_3$OD) with tetramethylsilane (TMS) as an internal standard and chemical shifts were recorded in ppm ($10^{-6}$).

The analytical low-resolution mass spectra (MS) were recorded on Agilent 1200 HPLC/6120 using a XBridge C18, 4.6×50 mm, 3.5 µm, using a gradient elution method: 5%-95% B for 1.5 min followed by 95% B over 2 min.

Solvent A: (10 mM Ammonium hydrogen carbonate in water)
Solvent B: Acetonitrile

The average of inhibitory rate of Flt3 kinase and IC$_{50}$ was determined by a Caliper's mobility shift assay (MSA).

Thin-layer silica-gel was Yantai Huanghai HSGF254 or Qingdao GF254 silica-gel plate. Column chromatography generally used Yantai Huanghai 200-300 mesh silica gel as carrier.

The following abbreviations have been used:
DMSO-D$_6$: deuterated-dimethyl sulfoxide;
CDCl$_3$: deuterated-chloroform;
CD$_3$OD: deuterated-methanol;
THF: tetrahydrofuran;
DMF: N,N-dimethylformamide;
EtOAc: ethyl acetate;
MeOH: methanol;
EtOH: ethanol;
MeCN: acetonitrile;
DIPEA: diisopropylethylamine;
TEA: triethylamine;
DCM: dichloromethane;
HOAc: acetic acid;
Cbz: benzyloxycarbonyl;
MeI: iodomethane;
HCHO: formaldehyde;
NaH: sodium hydride;
Br$_2$: bromine;
HBr: hydrogen bromide;
KSCN: potassium thiocyanate;
t-BuOK: potassium tert-butoxide;
Fe: iron powder;
K$_2$CO$_3$: potassium carbonate;
KOH: potassium hydroxyide;
DPPA: Diphenylphosphonic azide;
CH$_3$SO$_2$Cl(TsCl): methyl aminosulfonyl;
NaBH$_3$CN: sodium cyanoborohydride;
NH$_2$NH$_2$: hydrazine.

All the following intermediates were prepared according to either the reported literatures or by the methods described in this invention.

Examples 1-6

Compounds 8-1 to 8-6 were Made by the Method in Scheme-1

Synthesis of Compound 2

To a mixture of 2-chloro-5-nitro-4-thiocyanatopyrimidine (compound 1) (100 mg, 0.46 mmol) in DMF (50 ml) was added morpholine (60 mg, 0.69 mmol). After the mixture was stirred at rt for 1 h, water (20 ml) was added and then the precipitate was collected by the filtration to afford the crude compound 2 (83 mg, yield 43%) as a yellow solid, used in the next step without further purification.

m/z: [M+H]$^+$ 267.9

Synthesis of Compound 3

To a mixture of compound 2 (230 mg, 0.86 mmol) in HOAc (5 ml) was heated to 60° C., and then iron powder (125 mg, 2.24 mmol) was added. After the mixture was stirred at the same temperature for 1 h, the mixture was filtered through celite. The filtrate was evaporated, and the residue was dissolved in EtOAc (50 ml). Insoluble materials was removed by filtration, the filtrate was neutralized with saturated NaHCO$_3$ solution and then washed with brine dried over Na$_2$SO$_4$, and concentrated to give crude compound 3 (170 mg, yield 83%), used in the next step without further purification.

m/z: [M+H]$^+$ 238.0

Synthesis of Compound 5

To a mixture of compound 3 (170 mg, 0.72 mmol) in EtOH (10 ml) was added 2-bromo-1-(4-nitrophenyl)ethanone 4 (174 mg, 0.72 mmol). After the mixture was refluxed overnight, the reaction was cooled to room temperature, filtration of the resulting precipitate to afford crude compound 5 (66 mg, yield 24%) as a yellow solid, used in the next step without further purification.

m/z: [M+H]$^+$ 383.0

Synthesis of Compound 6

A mixture of compound 5 (65 mg, 0.17 mmol) in HOAc (5 ml) was heated to 60° C., and then iron powder (94 mg, 1.7 mmol) was added. After the mixture was stirred at the same temperature for 1 h, the mixture was filtered through celite. The filtrate was evaporated, the residue was neutralized with saturated NaHCO$_3$ solution, and extracted with EtOAc (20 ml×3). The combined organic extracts were washed with brine, dried over Na$_2$SO$_4$, filtered and concentrated to afford crude compound 6 (60 mg, yield 100%) as a red solid, used in the next step without further purification.

m/z: [M+H]$^+$ 353.1

The Synthesis of Compound 8-1

A mixture of compound 6 (20 mg, 0.056 mmol) and 5-tert-butyl-3-isocyanatoisoxazole 7 (11 mg, 0.068 mmol) in toluene (5 ml) was stirred at 80° C. for 2 h until the reaction finished (monitored by TLC). After cooled to room temperature, the reaction was then added with a mixture of DCM (10 ml), water (5 ml) and saturated NaHCO$_3$, The aqueous phase was extracted with DCM (10 ml×2), and the combined organic extracts were dried over NaSO$_4$, filtered and concentrated to volume of about 2 ml and petroleum ether was added to formation of a solid. The precipitate was collected by filtration to afford crude compound 8-1 (7 mg, yield 24%) as a pink solid.

m/z: [M+H]$^+$ 519.0

H$^1$NMR (CDCl$_3$): δ 9.32 (1H, br), 8.50 (1H, s), 7.83-7.79 (4H, m), 7.59-7.56 (2H, m), 5.92 (1H, s), 3.86 (4H, d, J=4.8 Hz), 3.82 (4H, d, J=4.0 Hz), 1.39 (9H, s).

Compound 8-2 was prepared according to the method of 8-1 in scheme-1, as a pink solid.

m/z: [M+H]$^+$ 477.0

Compound 8-3 was prepared according to the method of 8-1 in scheme-1, as an off-white solid.

m/z: [M+H]$^+$ 618.3

Compound 8-4 was prepared according to the method of 8-1 in scheme-1, as an off-white solid (TFA salt)

m/z: [M+H]$^+$ 518.2

Compound 8-5 was prepared according to the method of 8-1 in scheme-1, as a yellow solid.

m/z: [M+H]$^+$ 532.1

Compound 8-6 was prepared according to the method of 8-1 in scheme-1, as a light yellow solid.

m/z: [M+H]$^+$ 602.3

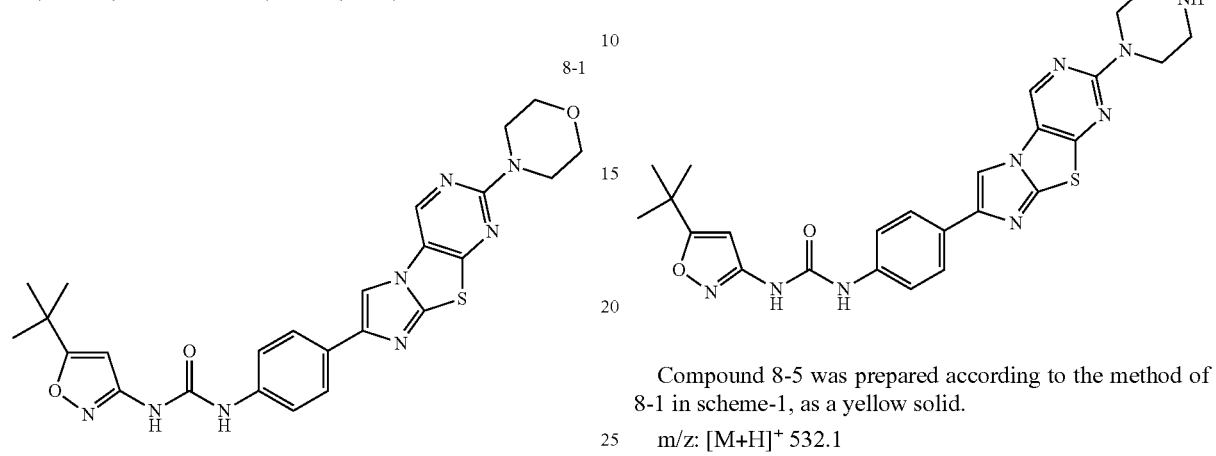

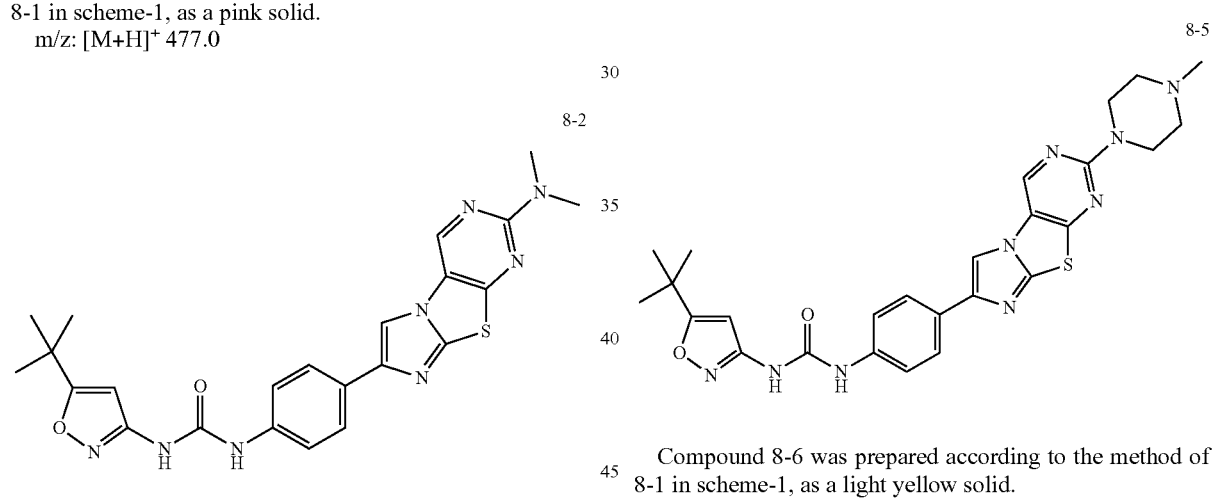

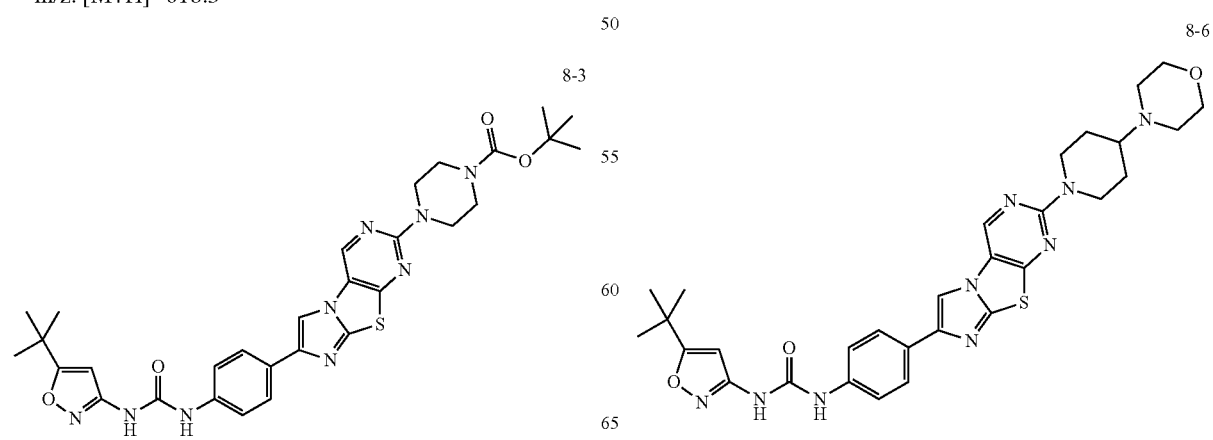

Example 7

Compound 19 was Made by the Method in Scheme-2

Synthesis of Compound 10

A mixture of compound 9 (3.0 g, 16.65 mmol) in aqueous KOH (5 N, 30 ml) was heated to reflux for 24 h. After cooled to room temperature, the reaction solution was adjusted pH=6 by adding concentrated HCl. The precipitated solid was collected by filtration, and dried under vacuum to afford crude compound 10 (2.4 g, yield 93%) as a brown solid, used in next step without further purification.

Synthesis of Compound 12

To a mixture of compound 10 (0.3 g, 1.93 mmol) in toluene (4 ml) was added acetyl chloride (compound 11) (0.167 g, 2.13 mmol) dropwise in 15 min. After the mixture was heated at 80° C. overnight, cooled to room temperature, the mixture was diluted with DCM (20 ml), and the adjusted pH=8 by saturated NaHCO$_3$. The organic phase was separated, washed with brine, dried over Na$_2$SO$_4$, and concentrated to give the desired crude compound 12 (0.23 g, yield 66%) as yellow oil, used in next step without further purification.

$^1$HNMR (CDCl$_3$): δ7.82 (1H, d, J=8.8 Hz), 7.28 (1H, d, J=2.4 Hz), 7.04 (1H, dd, J$_1$=8.8 Hz, J$_2$=2.4 Hz), 3.86 (3H, s), 2.79 (3H, s)

Synthesis of Compound 13

A mixture of compound 12 (1.5 g, 8.37 mmol) and compound 4 (2-bromine-4'-nitrobenzene ketone) (2.04 g, 8.37 mmol) in 5 ml of toluene was refluxed overnight. Filtration of resulted precipitate to afford the crude compound 13 (2.7 g, yield 76%) as a yellow solid, used in the next step without further purification.

Synthesis of Compound 14

To a mixture of compound 13 (1.0 g, 2.36 mmol) in EtOH (10 ml), was slowly added TEA (262 mg, 2.6 mmol). After the mixture was heated to 105° C. for 30 min, the mixture was cooled to room temperature. Filtrated of the resulted precipitate to afford crude compound 14 (0.76 g, yield 99%) as a yellow solid, used in the next step without further purification.

m/z: [M+H]$^+$ 325.0

Synthesis of Compound 15

A mixture of compound 14 (300 mg, 0.31 mmol) in 33% HBr in HOAc (6 ml) in a sealed tube was stirred at 100° C. overnight (monitored by TLC). After the reaction was cooled to room temperature, the mixture was diluted with EtOAc (100 ml), filtered and the cake was dissolved in DCM (20 ml) and washed with saturated NaHCO$_3$ solution. After the aqueous phase was extracted with DCM (20 ml×3), the combined organic phase was washed with brine, dried over Na$_2$SO$_4$, filtered, concentrated to a volume about 5 ml, petroleum ether (10 ml) was added and an yellow solid was precipitated out, collected the solid by the filtration to afford crude compound 15 (220 mg, yield 76%) as a yellow solid, used in the next step without further purification.

m/z: [M+H]$^+$ 311.0

Synthesis of Compound 17

To a mixture of compound 15 (50 mg, 0.16 mmol) in DMF (2 ml), was added K$_2$CO$_3$ (33 mg, 0.24 mmol) and 4-(2-chloroethyl) morpholine 16 (48 mg, 0.32 mmol). After the mixture was heated to 60° C. for 4 h, the mixture was partitioned between with DCM (20 ml) and water (10 ml), the aqueous phase was then extracted with DCM (10 ml×2). The combined organic phase was washed with brine, dried over Na$_2$SO$_4$, filtered and concentrated to give crude compound 17 (68 mg, yield 100%) as a yellow solid, used in the next step without further purification.

m/z: [M+H]$^+$ 424.0

Synthesis of Compound 18

A mixture of compound 17 (68 mg, 0.16 mmol) in HOAc (3 ml) was heated to 60° C., and then iron powder (89 mg, 1.61 mmol) was added. After the mixture was stirred at the same temperature for 1 h, the mixture was filtered through celite. The filtrate was evaporated and added in DCM (10 ml), then neutralized with aqueous saturated NaHCO$_3$ solution, and finally the aqueous phase was extracted with DCM (10 ml×2). The combined organic phase was washed with brine, dried over Na$_2$SO$_4$, filtered and concentrated to give crude compound 18 (47 mg, yield 74%), used in the next step without further purification.

m/z: [M+H]$^+$ 394.1

Synthesis of Compound 19

To a mixture of compound 18 (47 mg, 0.12 mmol) in toluene (5 ml), was added compound 7 (5-tert-butyl-3-isocyanatoisoxazole) (24 mg, 0.14 mmol). After the mixture was stirred at 80° C. for 2 h, the mixture was diluted with water (10 ml), and extracted with DCM (10 ml×3). The combined organic phase was washed with saturated NaHCO$_3$ solution and brine, separately, dried over Na$_2$SO$_4$, filtered and concentrated to afford crude product, which was purified by preparative TLC (5% MeOH in DCM), and then recrystallized from DCM and petroleum ether to give compound 19 (8 mg, yield 12%) as a yellow solid.

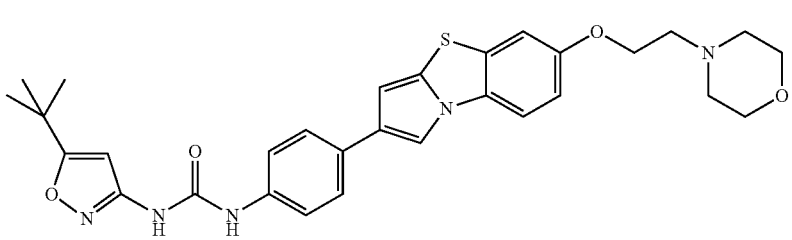

m/z: [M+H]$^+$ 560.2

H$^1$NMR (DMSO-d$_6$): δ 9.52 (s, 1H), 8.87 (s, 1H), 8.19 (s, 1H), 7.81-7.79 (d, J=8.8 Hz, 1H), 7.58-7.45 (m, 5H), 7.07 (m,

1H), 6.66 (s, 1H), 6.52 (s, 1H), 4.14 (t, J=5.6 Hz, 2H), 3.59 (t, J=4.4 Hz, 4H), 3.3 (m, 4H), 2.72 (t, J=5.6 Hz, 2H), 1.30 (s, 9H).

Examples 8-22

Compounds 28-1 to 28-15 were Made by the Method in Scheme-3-A

Synthesis of 2-methoxy-5-nitropyridine

A mixture of compound 20 (5.6 g, 35.3 mmol) in MeOH (50 ml) was added potassium tert-butoxide (5 g, 44.5 mmol). After the mixture was stirred at rt for 1 h, the mixture was poured into water (500 ml), filtration of resulted precipitate, air-dried to afford 2-methoxy-5-nitropyridine (5.04 g, yield 93%) as a white powder, used in the next step without further purification.

Synthesis of Compound 22

A mixture of 2-methoxy-5-nitropyridine (5.0 g, 32.4 mmol) in HOAc (50 ml) was added iron powder (5 g, 89.53 mmol). After the mixture was heated to 60° C. for 2 h, the mixture was filtered through celite, and the filtered cake was washed with HOAc and then water. The filtrate was concentrate and the residue was neutralized with saturated NaHCO$_3$ solution, the aqueous phase was extracted with DCM (100 ml), and insoluble materials were removed by filtration. After the aqueous phase was extracted with DCM (100 ml×4), the combined organic phase was washed with brine and concentrated to afford crude product, which was purified by silica gel column chromatography (2% MeOH in DCM) to afford compound 22 (3.5 g, yield 86%) as a brown oil m/z: [M+H]$^+$ 125.2

Synthesis of Compound 23

A mixture of compound 22 (3.4 g, 27.39 mmol) and potassium thiocyanate (11.7 g, 120.5 mmol) in HOAc (50 ml) at 0° C., bromine (2.35 ml in 25 ml of HOAc) was added from a dropping funnel at such a rate that the temperature never rose beyond 0° C. After all the bromine has been added (75 min), the mixture was stirred at rt overnight. The mixture was quenched by saturated Na$_2$SO$_3$ solution, concentrated under vacuum and the residue was neutralized with saturated NaHCO$_3$ solution, and then DCM (100 ml) was added. Insoluble materials were removed by filtration, and the separated aqueous phase was extracted with DCM (100 ml×4). The combined organic phase was washed with brine, dried over NaSO$_4$, filtered and concentrated to afford crude compound 23 (4.0 g, yield 80%) as a yellow solid, used in the next step without further purification.

m/z: [M+H]$^+$ 182.2

Synthesis of Compound 24

Compound 23 (0.5 g, 2.76 mmol) was dissolved in 33% HBr in HOAc (5 ml), the mixture was stirred at 130° C. for 3 h, and cooled to room temperature. The mixture was solidified by adding acetone (10 ml). The desired compound 24 (800 mg, yield 88%) was collected by filtration as a white solid, used in the next step without further purification.

m/z: [M+H]$^+$ 168.1

Synthesis of Compound 25

A mixture of compound 24 (hydrobromide) (400 mg) in EtOH (10 ml) was added potassium carbonate (400 mg), the mixture was stirred at rt for 1 h. The solid was filtered off and the filtrate was concentrated to afford compound 24 in the form of a free base (205 mg, 1.23 mmol), which was then dissolved in EtOH (15 ml). The resulted solution was added compound 4 (394 mg, 1.61 mmol). After the resulted mixture was refluxed overnight, filtration of the resulted precipitate to afford crude compound 25 (140 mg, yield 37%) as a yellow solid, used in the next step without further purification.

m/z: [M+H]$^+$ 313.1

Synthesis of Compound 26

A mixture of compound 25 (50 mg, 0.16 mmol) in DMF (2 ml) was added potassium carbonate (44 mg, 0.32 mmol) and 4-(2-chloroethyl) morpholine (compound 16) (35 mg, 0.24 mmol). After the mixture was stirred at 60° C. for 2 h, the reaction mixture was poured into water (10 ml), the precipitated solid was collected by filtration, washed with water and methyl tert-butyl ether to give crude compound 26 (30 mg, yield 44%) as a yellow solid, used in the next step without further purification.

m/z: [M+H]$^+$ 426.2

Synthesis of Compound 27

A mixture of compound 26 (30 mg, 0.07 mmol) in HOAc (2 ml) was heated to 60° C., and to this mixture was added iron powder (39 mg, 0.7 mmol). After the reaction mixture was stirred at 60° C. for 1 h, the mixture was filtered through celite, and the filtrate was concentrated under vacuum. The concentrated residue was neutralized with saturated NaHCO$_3$ solution, and the aqueous was extracted with 2% methanol in DCM (10 ml×5), the combined organic extracts were washed with brine, dried over NaSO$_4$, filtered and concentrated to afford crude product, which was purified by preparative TLC (5% MeOH in DCM) to afford compound 27 (27 mg, yield 97%) as a yellow solid.

m/z: [M+H]$^+$ 396.2

Synthesis of Compound 28-1

A mixture of compound 27 (27 mg, 0.068 mmol) and 5-tert-butyl-3-isocyanatoisoxazole 7 (12 mg, 0.075 mmol) in toluene (3 ml) was stirred at 80° C. for 2 h until the reaction completed (monitored by TLC). After cooled to room temperature, the reaction was portioned between DCM (5 ml) and saturated NaHCO$_3$ solution (10 ml). The aqueous phase was then extracted with DCM (10 ml×2), and the combined organic extracts were dried over NaSO$_4$, filtered and concentrated to volume of about 5 ml and then petroleum ether (5 ml) was added to the formation of a solid. The precipitate was collected by filtration to afford compound 28-1 (11 mg, yield 28%) as a yellow solid.

m/z: [M+H]$^+$ 562.2

H$^1$NMR (DMSO-d$_6$): δ 9.72-9.65 (1H, br), 9.25-9.19 (1H, br), 8.63 (1H, s), 8.32-8.30 (1H, d, J=8.8 Hz), 7.79-7.77 (2H, d, J=9.2 Hz), 7.54-7.52 (2H, d, J=8.4 Hz), 7.07-7.05 (1H, d, J=8.8 Hz), 6.53 (1H, s), 4.44 (2H, t, J=5.6 Hz), 3.57 (4H, t, J=4.4 Hz), 3.3 (4H, m), 2.72 (2H, t, J=6.0 Hz), 1.31 (9H, s).

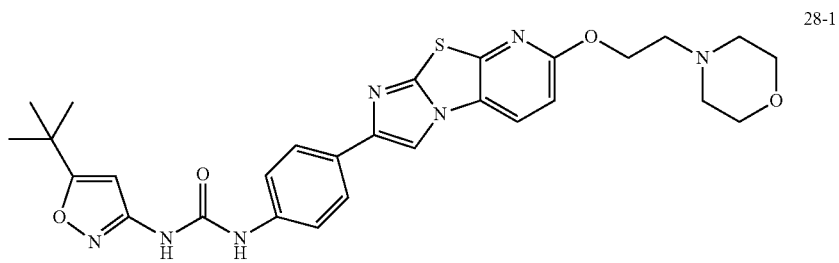 [SMILES: CC(C)(C)c1cc(NC(=O)Nc2ccc(-c3cn4c(n3)sc3nc(OCCN5CCOCC5)ccc34)cc2)no1]
Compound 28-2 was prepared according to the method of 28-1 in scheme 3-A as a yellow solid.
m/z: [M+H]+ 520.2
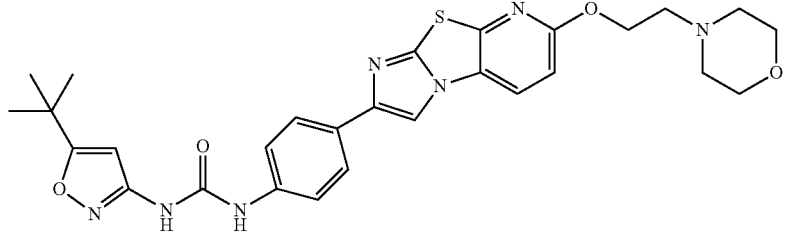
Compound 28-3 was prepared according to the method of 28-1 in scheme 3-A as a yellow solid.
m/z: [M+H]+ 561.2
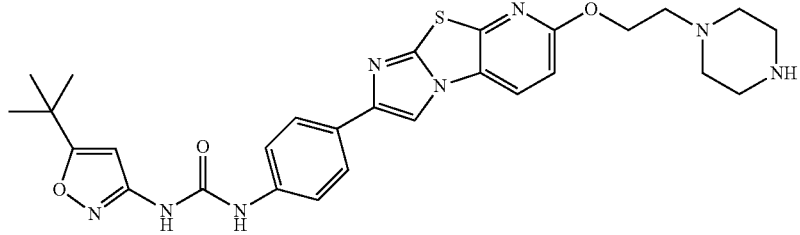
Compound 28-4 was prepared according to the method of 28-1 in scheme 3-A as a yellow solid.
m/z: [M+H]+ 575.3
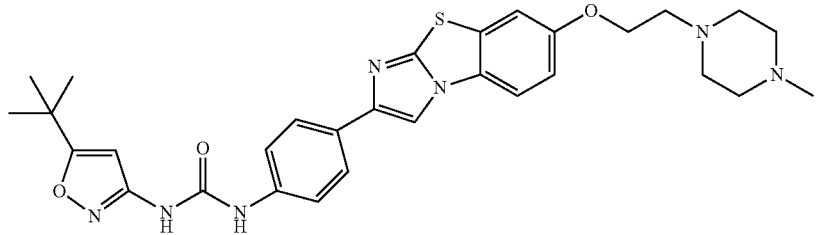

Compound 28-5 was prepared according to the method of 28-1 in scheme 3-A as an red solid.
m/z: [M+H]+ 617.1
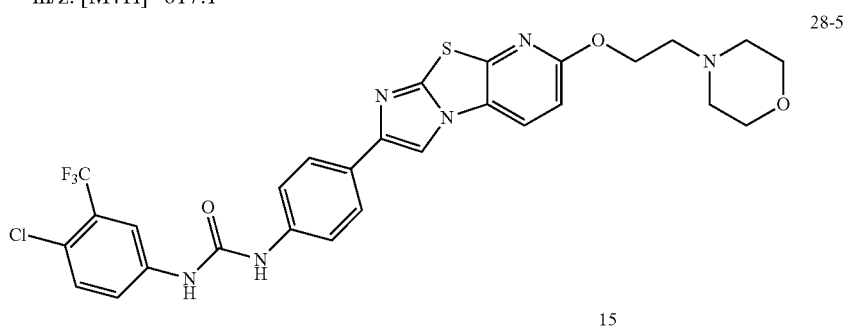
Compound 28-6 was prepared according to the method of 28-1 in scheme 3-A as a white solid.
m/z: [M+H]+ 576.3
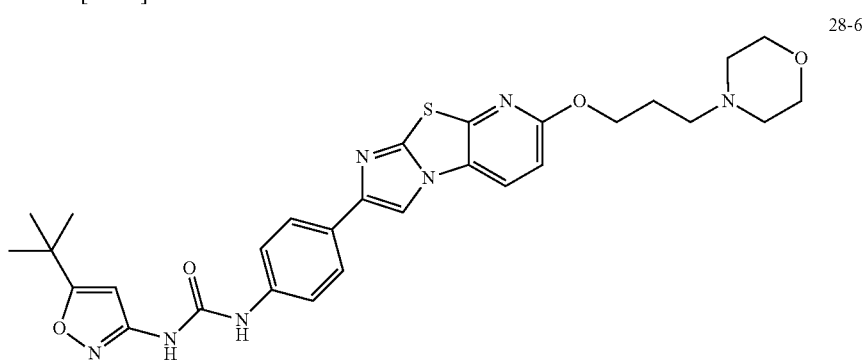
Compound 28-7 was prepared according to the method of 28-1 in scheme 3-A as a yellow solid.
m/z: [M+H]+ 573.3
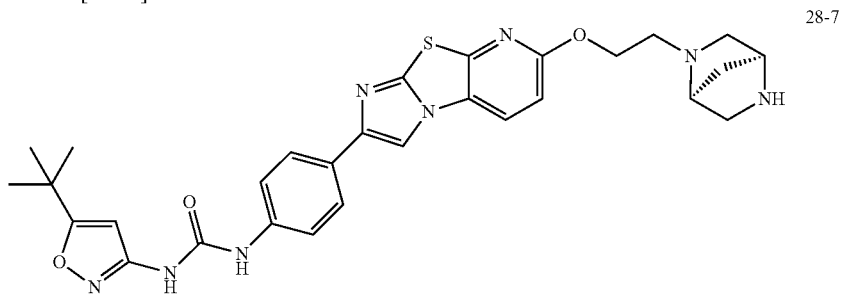
Compound 28-8 was prepared according to the method of 28-1 in scheme 3-A as a white solid.
m/z: [M+H]+ 587.3
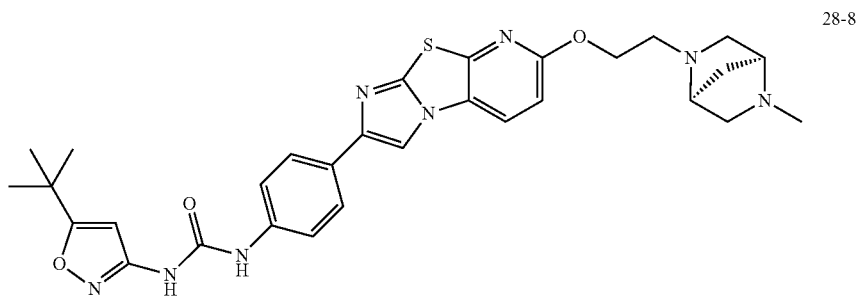 [SMILES: CN1C[C@@H]2C[C@H]1CN2CCOc1ccc2c(n1)sc1nc(-c3ccc(NC(=O)Nc4cc(C(C)(C)C)on4)cc3)cn12]

Compound 28-9 was prepared according to the method of 28-1 in scheme 3-A as a white solid.
m/z: [M+H]+ 546.3

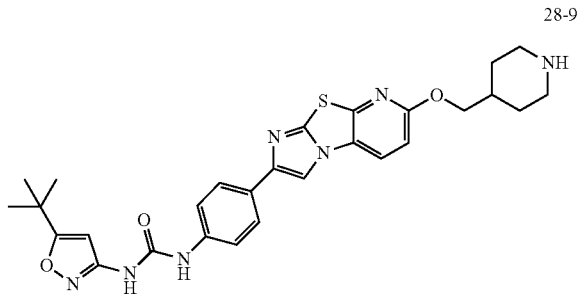 [SMILES: CC(C)(C)c1cc(NC(=O)Nc2ccc(-c3cn4c(n3)sc3nc(OCC5CCNCC5)ccc34)cc2)no1]

28-9

Compound 28-10 was prepared according to the method of 28-1 in scheme 3-A as white solid.
m/z: [M+H]+ 560.3

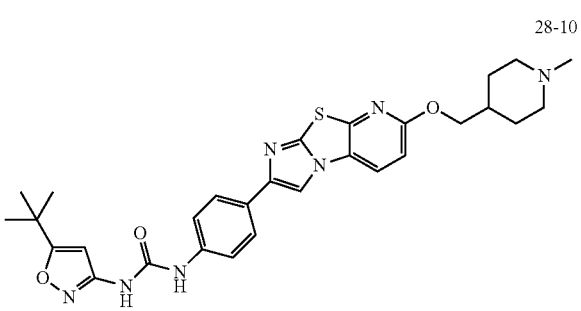 [SMILES: CN1CCC(COc2ccc3c(n2)sc2nc(-c4ccc(NC(=O)Nc5cc(C(C)(C)C)on5)cc4)cn23)CC1]

28-10

Compound 28-11 was prepared according to the method of 28-1 in scheme 3-A as white solid.
m/z: [M+H]+ 518.3

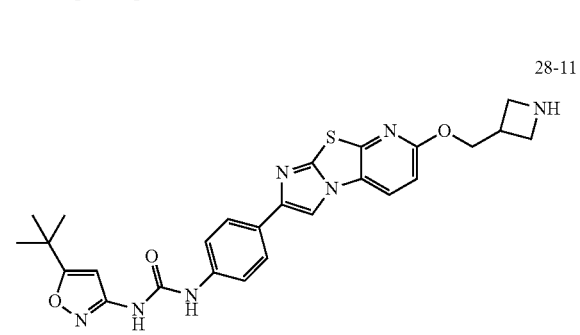 [SMILES: CC(C)(C)c1cc(NC(=O)Nc2ccc(-c3cn4c(n3)sc3nc(OCC5CNC5)ccc34)cc2)no1]

28-11

Compound 28-12 was prepared according to the method of 28-1 in scheme 3-A as white solid.
m/z: [M+H]+ 548.2

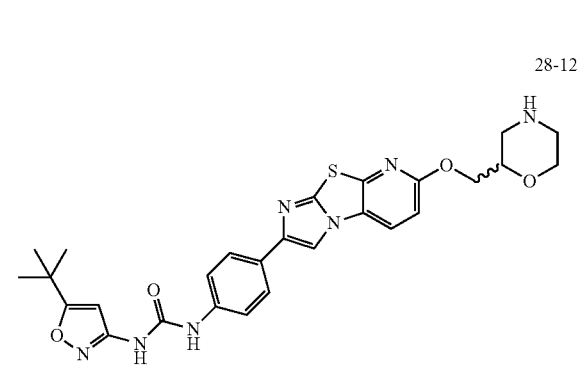 [SMILES: CC(C)(C)c1cc(NC(=O)Nc2ccc(-c3cn4c(n3)sc3nc(OCC5CNCCO5)ccc34)cc2)no1]

28-12

Compound 28-13 was prepared according to the method of 28-1 in scheme 3-A as white solid.
m/z: [M+H]+ 562.3

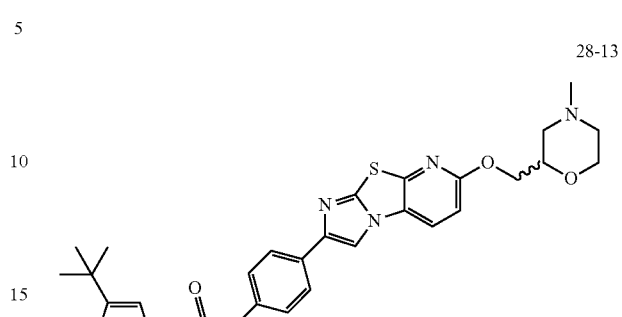

28-13

Compound 28-14 was prepared according to the method of 28-1 in scheme 3-A as a off-white solid.
m/z: [M+H]+ 548.3

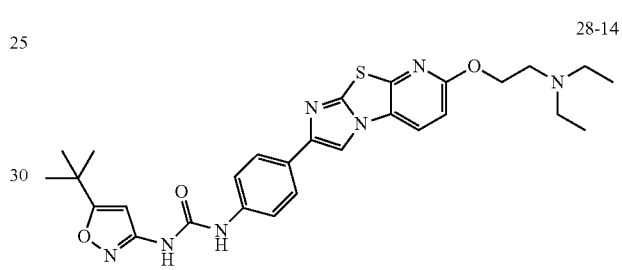

28-14

Compound 28-15 was prepared according to the method of 28-1 in scheme 3-A as a off-white solid.
m/z: [M+H]+ 574.3

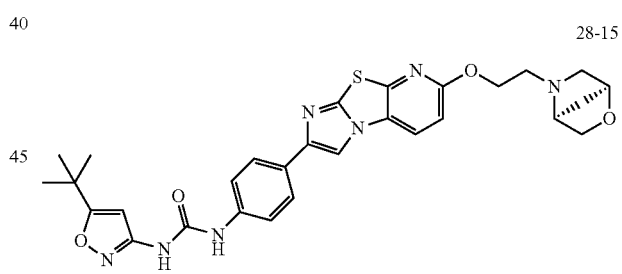

28-15

Examples 23-25

Compounds 35-1 to 35-3 were Made by the Method in Scheme-3-B

Synthesis of Compound 29

To a mixture of compound 20 (500 mg, 3.15 mmol) and compound 21 (907 mg, 4.10 mmol) in DMF (15 ml) was added $K_2CO_3$ (871 mg, 6.31 mmol). The mixture was heated to 60° C. and stirred for 48 h. The mixture was diluted with DCM (150 ml), the organic phase was washed with water, brine, dried $Na_2SO_4$ separately filtered and concentrated to afford crude product, which was purified by silica gel column chromatography (0-5% MeOH in DCM) to afford compound 29 (430 mg, yield 32%) as a yellow solid.
m/z: [M+H]+ 344.1

Synthesis of Compound 30

To a mixture of compound 29 (350 mg, 1.02 mmol) in HOAc (30 ml) was added iron powder (1.14 g, 20.39 mmol). The mixture was heated to 60° C. and stirred for 2 h. The mixture was concentrate and the residue was neutralized with saturated NaHCO₃ solution, and extracted with DCM (100 ml). The organic layer was washed with brine, dried Na₂SO₄. The solvent was removed under vacuum. The crude product was purified by preparative TLC (5% MeOH in DCM) to afford compound 30 (210 mg, yield 66%) as a white solid.

m/z: [M+H]⁺ 314.3

Synthesis of Compound 31

To a solution of compound 30 (53 mg, 0.169 mmol) in HOAc (2 ml) was added KSCN (73 mg, 0.761 mmol). After the solution was cooled to 0° C., then Br₂ (40 mg, 0.253 mmol) in HOAc (1 ml) was added dropwise that the temperature never rose beyond 0° C. After all the bromine has been added (60 min), the mixture was stirred at rt overnight. The mixture was quenched by saturated Na₂SO₃ solution, and concentrated. The residue was neutralized with saturated NaHSO₄ solution, and DCM (100 ml) was added. Insoluble materials were removed by filtration, and the separated aqueous phase was extracted with DCM (100 ml×4). The combined organic phase was washed with brine, dried over NaSO₄, filtered and concentrated to afford crude product, which was purified by preparative TLC (5% MeOH in DCM) to afford compound 31 (34 mg, yield 54%) as a white solid.

m/z: [M+H]⁺ 371.1

Synthesis of Compound 32

To a mixture of compound 31 (34.0 mg, 0.091 mmol) in EtOH (3 ml) was added compound 4 (2-bromo-1-(4-nitrophenyl)ethanone) (22.4 mg, 0.091 mmol). The resulted mixture was refluxed overnight. Filtrated of the resulted precipitate to afford crude compound 32 (12 mg, yield 25%) as a yellow solid, used in the next step without further purification.

m/z: [M+H]⁺ 516.1

Synthesis of Compound 33

A mixture of compound 32 (20 mg, 0.038 mmol) and iron powder (43 mg, 0.775 mmol) in HOAc (5 ml) was heated to 60° C. and stirred for 2 h, mixture was then filtered through celite, the filtrate was concentrated. The residue was neutralized with saturated NaHCO₃ solution, extracted with DCM (10 ml×5). The combined extracts were washed with brine, dried over NaSO₄, filtered and concentrated to afford crude product, which was purified by preparative TLC (5% MeOH in DCM) to afford compound 33 (8 mg, yield 42%) as a yellow solid.

m/z: [M+H]⁺ 486.2

Synthesis of Compound 34

A mixture of compound 33 (8 mg, 0.016 mmol) and 5-tert-butyl-3-isocyanatoisoxazole 7 (3.2 mg, 0.019 mmol) in toluene (2 ml) was stirred at 80° C. for 2 h. The reaction was added with DCM (5 ml), and the mixture was neutralized with saturated NaHCO₃ solution. The aqueous phase was extracted with DCM (10 ml×2), and the combined organic extracts were dried over NaSO₄, filtered and concentrated to give the crude product which was purified by preparative TLC (7% MeOH in DCM) to afford compound 34 (7.0 mg, yield 65%) as a yellow solid.

m/z: [M+H]⁺ 652.2

Synthesis of Compound 35-1

To a mixture of compound 34 (4 mg, 6.1 umol) in AcOH (2 ml) was added 33% HBr in HOAc (1 ml), the mixture was stirred at rt. for 3 h. The mixture was then diluted with DCM (30 ml) and water (20 ml), neutralized with saturated NaHCO₃, and extracted with DCM (10 ml×2). The combined organic extracts were dried over NaSO₄, filtered and concentrated to give the crude product, and washed by DCM (3 ml) to afford pure compound 35-1 (1.5 mg, yield 47%) as a white solid.

m/z: [M+H]⁺ 518.2

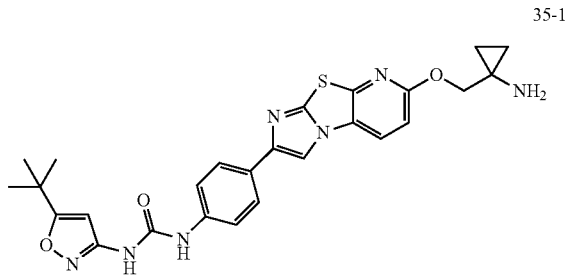 [SMILES: CC(C)(C)c1cc(NC(=O)Nc2ccc(-c3cn4c(n3)sc3nc(OCC5(N)CC5)ccc34)cc2)no1]

35-1

Synthesis of Compound 35-2

The solution of compound 35-1 (15 mg, 0.029 mmol) in DCM (2 ml) was added triethyl amine (6 mg, 0.058 mmol), 4-N,N-dimethylaminopyridine (4 mg, 0.029 mmol), and acetic anhydride (6 mg, 0.058 mmol). The resulted reaction solution was stirred at RT for 2 h, and the reaction was concentrated and purified by preparative TLC (7% MeOH in DCM) to afford compound 35-2 (7 mg, yield 43%), as a light yellow solid.

m/z: [M+H]⁺ 560.3

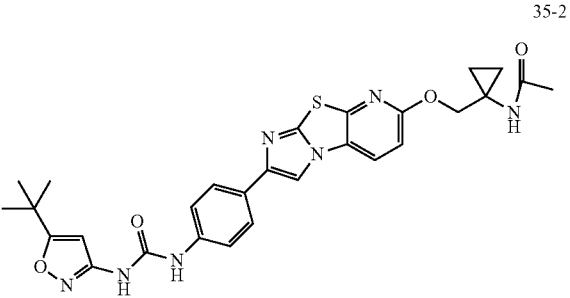 [SMILES: CC(=O)NC1(COc2ccc3c(n2)sc2nc(-c4ccc(NC(=O)Nc5cc(C(C)(C)C)on5)cc4)cn23)CC1]

35-2

Synthesis of Compound 35-3

The solution of compound 35-1 (15 mg, 0.029 mmol) in DCM (2 ml), was added triethyl amine (6 mg, 0.058 mmol), and methanesulfonyl chloride (4 mg, 0.032 mmol). The resulted reaction solution was stirred at rt for 2 h, and the reaction was concentrated and purified by preparative TLC (7% MeOH in DCM) to afford compound 35-3 (1.2 mg, yield 6.9%), as a white solid.

m/z: [M+H]⁺ 596.3

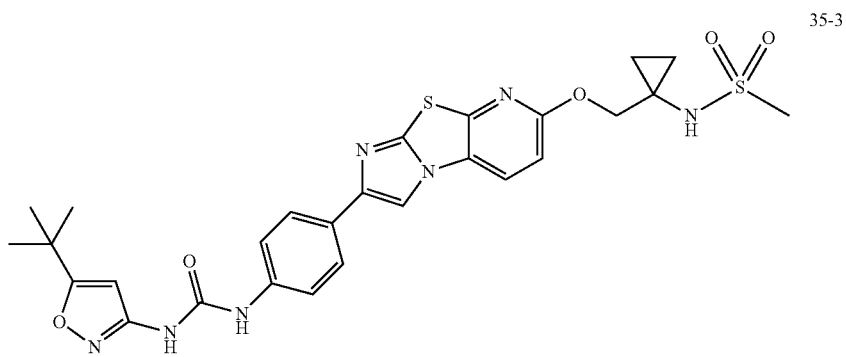 [SMILES: CC(C)(C)c1cc(NC(=O)Nc2ccc(-c3cn4c(n3)sc3nc(OCC5(NS(C)(=O)=O)CC5)ccc34)cc2)no1]

35-3

Example 26

Compound 35-4 was Made by the Method in Scheme-3-B, Through Using (S)-(−)-1-Boc-2-Pyrrolidinemethanol to Replace Intermediate 21, as a Light Pink Solid

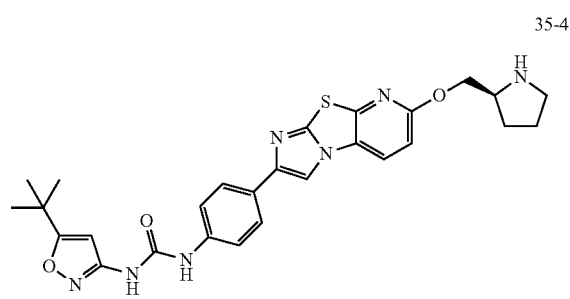 [SMILES: CC(C)(C)c1cc(NC(=O)Nc2ccc(-c3cn4c(n3)sc3nc(OC[C@@H]5CCCN5)ccc34)cc2)no1]

35-4 m/z: [M+H]⁺ 532.3

Examples 27-30

Compounds 39-1 to 39-4 were Made by the Method in Scheme-3-C

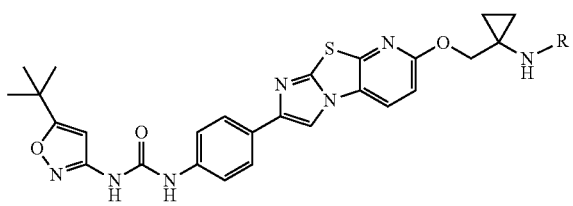

R = Me, 39-1
= Et, 39-2
= n-Pr, 39-3

Synthesis of Compound 36-1

A mixture of compound 32 (50 mg, 0.096 mmol) in DMF (2 ml) was added 60% NaH (19.4 mg, 0.484 mmol). After stirred for 30 min at rt, CH₃I (68.8 mg, 0.484 mmol) was added to the mixture. The mixture was stirred at rt for 30 min. The reaction mixture was diluted with DCM (30 ml), washed with water, brine, dried Na₂SO₄, filtered and concentrated to afford crude product, which was washed by petroleum ether to afford crude compound 36-1 (50 mg, yield 97%) as a yellow solid, used in the next step without further purification.

m/z: [M+H]⁺ 530.1

Synthesis of Compound 37-1

A mixture of 36-1 (50 mg, 0.094 mmol) and iron powder (105 mg, 1.890 mmol) in HOAc (10 ml) was heated to 60° C. and stirred for 2 h. The mixture was filtered through celite, and the filtrate was concentrated. The residue was neutralized with aqueous saturated NaHCO₃ solution, and the aqueous was extracted with DCM (10 ml×5). The combined organic extracts were washed with brine, dried over NaSO₄, filtered and concentrated to afford crude product, which was purified by preparative TLC (5% MeOH in DCM) to afford 37-1 (23 mg, yield 49%) as a yellow solid, used in the next step without further purification.

m/z: [M+H]⁺ 500.2

Synthesis of Compound 38-1

A mixture of compound 37-1 (23 mg, 0.046 mmol) and 5-tert-butyl-3-isocyanatoisoxazole 7 (9.1 mg, 0.055 mmol) in toluene (3 ml) and CHCl₃ (1.5 ml) was stirred at 80° C. for 2 h, and the reaction was diluted with DCM (5 ml), and the mixture was then neutralized with aqueous saturated NaHCO₃ solution. The aqueous phase was extracted with DCM (10 ml×2), and the combined organic extracts were dried over NaSO₄, filtered and concentrated to give the crude product, which was purified by preparative TLC (7% MeOH in DCM) to afford compound 38-1 (19 mg, yield 62%) as a white solid.

m/z: [M+H]⁺ 666.2

Synthesis of Compound 39-1

To a mixture of compound 38-1 (10.0 mg, 15 umol) in AcOH (2 ml) was added 33% HBr in HOAc (1 ml), the mixture was stirred at rt for 3 h. The mixture was partitioned between DCM (30 ml) and water (20 ml), neutralized with saturated NaHCO₃, and the aqueous was extracted with DCM (10 ml×2). The combined organic extracts were dried over NaSO₄, filtered and concentrated to give the crude product which was purified by preparative TLC (7% MeOH in DCM) to afford compound 39-1 (4.2 mg, yield 53%) as a white solid.

m/z: [M+H]⁺ 532.3

¹HNMR (DMSO-d₆): δ 9.56 (1H, s), 8.91 (1H, s), 8.64 (1H, s), 8.33-8.31 (1H, d, J=8.8 Hz), 7.79-7.77 (2H, d, J=8.8 Hz), 7.54-7.52 (2H, d, J=8.8 Hz), 7.09-7.07 (1H, d, J=8.8 Hz), 6.53 (1H, s), 4.32 (2H, s), 2.35 (3H, s), 1.31 (9H, s), 0.64 (4H, m)

Compound 39-2 was prepared according to the method of 39-1 in scheme 3-C as a off-white solid.

m/z: [M+H]⁺ 546.3

¹HNMR (DMSO-d₆): δ 9.55 (1H, s), 8.93 (1H, s), 8.64 (1H, s), 8.33-8.31 (1H, d, J=8.8 Hz), 7.79-7.77 (2H, d, J=8.8 Hz), 7.54-7.52 (2H, d, J=8.4 Hz), 7.09-7.07 (1H, d, J=8.8 Hz), 6.52 (1H, s), 4.32 (2H, s), 2.75-2.69 (2H, q, J=7.2), 1.31 (9H, s), 1.00-0.96 (3H, t, J=7.2 Hz), 0.65 (4H, s).

Compound 39-3 was prepared according to the method of 39-1 in scheme 3-C as a light yellow solid.

m/z: [M+H]⁺ 560.3

Synthesis of Compound 39-4

A mixture of compound 39-1 (15 mg, 0.028 mmol) in MeOH (5 ml) was added 37% formaldehyde (0.1 ml) and one drop of TFA. After the mixture was stirred at rt. for 4 h, NaBH₃CN (18 mg, 0.293 mmol) was added to the reaction mixture, and stirred overnight at rt. The solvent was removed under vacuum, and the residue was partitioned between DCM (50 ml) and water (20 ml). The separated aqueous phase was extracted with DCM (10 ml×2), and the combined organic extracts were washed with brine, dried over NaSO₄, and concentrated to give the crude product which was purified by preparative TLC (7% MeOH in DCM) to afford compound 39-4 (11 mg, yield 71%) as a white solid.

m/z: [M+H]⁺ 546.2

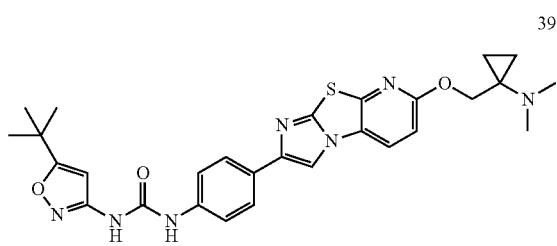

39-4

Example 31

Compound 46 was Made by the Method in Scheme-3D

Synthesis of Compound 41

A mixture of compound 20 (5.0 g, 31.54 mmol) in DMF (50 ml), was slowly add morpholine 40 (6.87 g, 78.84 mmol). The mixture was stirred at rt for 1 h, and yellowish solid was precipitated out. The resulted suspension was poured in to water (100 ml) and the precipitate solid was collected by filtration, and washed with tret-Butyl methyl ether, air-dried to give the crude compound 41 (7.4 g, yield 100%) as a light yellow solid, used in the next step without further purification.

m/z: [M+H]⁺ 210.1

Synthesis of Compound 42

A mixture of compound 41 (4 g, 19.1 mmol) in HOAc (40 ml) was added iron powder (5.34 g, 89.53 mmol). The mixture was heated to 60° C. and stirred for 2 h, then the mixture was filtered through celite, the filtered cake was washed with HOAc and then water. The filtrate was concentrated and the residue was neutralized with saturated NaHCO₃ solution, the aqueous was extracted with EtOAc (100 ml×5) and DCM (100 ml×2). The organic combined extracts were washed with brine, dried over NaSO₄, filtered and concentrated to afford crude compound 42 (2.7 g, yield 79%) as a red solid, used in the next step without further purification.

m/z: [M+H]⁺ 180.3

Synthesis of Compound 43

To a mixture of compound 42 (2.0 g, 11.2 mmol) in HOAc (20 ml) was added KSCN (4.7 g, 49.1 mmol), and the solution was cooled to 0° C. To this reaction solution was added Br₂ (0.95 ml in 20 ml HOAc) by a dropping funnel at such a rate that the temperature never rose above 0° C. After all the bromine has been added (75 min), the mixture was stirred at rt overnight. The mixture was quenched by saturated Na₂SO₃ solution, concentrated under vacuum and the residue was neutralized with saturated NaHCO₃ solution. The aqueous was added DCM (100 ml), and insoluble materials were removed by filtration. The separated aqueous phase was then extracted with DCM (100 ml×2), and the combined organic extracts were washed with brine, dried over NaSO₄, filtered and concentrated under vacuum to afford crude product, which was purified by column chromatography on silica gel (2%-3% MeOH in DCM) to afford compound 43 (450 mg, yield 17%) as a yellow solid.

m/z: [M+H]⁺ 237.1

Synthesis of Compound 44

To a solution of compound 43 (200 mg, 0.85 mmol) in EtOH (5 ml), was added 2-bromo-1-(4-nitrophenyl)ethanone 4 (206 mg, 0.85 mmol), the reaction solution was refluxed overnight. The resulted precipitate was collected by filtration to afford crude compound 44 (144 mg, yield 45%) as a yellow solid, used in the next step without further purification.

Synthesis of Compound 45

To a mixture of compound 44 (140 mg, 0.37 mmol) in HOAc (10 ml) heated to 60° C. was added iron powder (102 mg, 1.84 mmol), and the mixture was stirred at the same temperature for 1 h. The mixture was filtered through celite, and the filtrate was evaporated and residue was neutralized with saturated NaHCO₃ solution, and the aqueous was extracted with DCM (20 ml×3). The combined organic extracts were washed with brine, dried over Na₂SO₄, filtered and concentrated to afford crude product, which was purified by silica gel column chromatography (2%-3% MeOH in DCM) to afford compound 45 (26 mg, yield 20%) as a yellow solid.

m/z: [M+H]⁺ 352.2

Synthesis of Compound 46

A mixture of compound 45 (10 mg, 0.028 mmol) and 5-tert-butyl-3-isocyanatoisoxazole 7 (9 mg, 0.056 mmol) in the mixed solvents of toluene (3 ml) and chloroform (3 ml) was stirred at 80° C. for 2 h until the reaction finished (monitored by TLC). The reaction was diluted with DCM (10 ml), and the mixture was neutralized with saturated NaHCO₃ solution. The aqueous phase was extracted with DCM (5 ml), and the combined organic extracts were dried over NaSO₄, filtered and concentrated to volume of about 5 ml and petroleum ether (5 ml) was added to formation of a solid. The precipitate was collected by filtration to afford crude compound 46 (10.8 mg, yield 73%) as an off-white solid.

m/z: [M+H]$^+$ 518.2

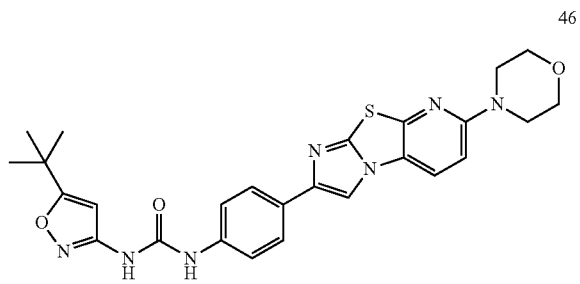 [SMILES: CC(C)(C)c1cc(NC(=O)Nc2ccc(-c3cn4c(n3)sc3nc(N5CCOCC5)ccc34)cc2)no1]

46

Examples 32-33

Compounds 53-1 to 53-2 were Made by the Method in Scheme-3-E

Synthesis of Compound 48

To a solution of compound 20 (50 mg, 0.315 mmol) and compound 47 (64 mg, 0.315 mmol) in acetonitrile (10 ml) was added DIPEA (122 mg, 0.946 mmol). The mixture was stirred at rt for 48 h, and was diluted with DCM (20 ml), washed with water, brine, and dried Na$_2$SO$_4$. The solvent was removed under vacuum, and the crude product was purified by silica gel column chromatography (100% DCM to 5% MeOH in DCM) to afford compound 48 (58 mg, yield 73%) as a yellow oil.

m/z: [M+H]$^+$ 253.2

Synthesis of Compound 49

To a solution of compound 48 (200 mg, 0.792 mmol) in HOAc (10 ml) was added iron powder (442 mg, 7.93 mmol). After the mixture was heated to 60° C. and stirred for 2 h, the mixture was concentrate and the residue was neutralized with aqueous saturated NaHCO$_3$ solution, water extracted with DCM (100 ml). The organic phase was washed with brine, dried Na$_2$SO$_4$, filtered and concentrated to give the crude product which was purified by preparative TLC (15% MeOH in DCM) to afford compound 49 (75 mg, yield 42%) as a yellow solid.

m/z: [M+H]$^+$ 223.3

Synthesis of Compound 50

A solution of compound 49 (72 mg, 0.323 mmol) and KSCN (141 mg, 1.460 mmol) in HOAc (5 ml) was cooled to 0° C., then Br$_2$ (77 mg, 0.485 mmol) in HOAc (1 ml) was added dropwise that the temperature never rose beyond 0° C. After all the bromine has been added (60 min), the mixture was stirred at rt overnight, and the reaction was quenched by saturated Na$_2$SO$_3$ solution. The reaction mixture was concentrated and the residue was neutralized with aqueous saturated NaHCO$_3$ solution, and diluted with DCM (100 ml). Insoluble materials were removed by filtration, and the separated aqueous phase was extracted with DCM (50 ml×4). The combined organic extracts were washed with brine, dried over NaSO$_4$, filtered and concentrated to afford crude product which was purified by preparative TLC (5% MeOH in DCM) to afford compound 50 (26 mg, yield 29%) as a brown solid.

m/z: [M+H]$^+$ 280.2

Synthesis of Compound 51

To a mixture of compound 50 (26 mg, 0.093 mmol) in EtOH (5 ml) was added 2-bromo-1-(4-nitrophenyl)ethanone 4 (22.7 mg, 0.093 mmol). The resulted mixture was refluxed overnight, and the resulted precipitate was collected by filtration to afford crude compound 51 (23 mg, yield 58%) as a yellow solid, used in the next step without further purification.

m/z: [M+H]$^+$ 425.1

Synthesis of Compound 52

A mixture of compound 51 (30 mg, 0.070 mmol) and iron powder (78 mg, 1.410 mmol) in HOAc (5 ml) was heated to 60° C. for 2 h. Then the mixture was filtered through celite, and the filtrate was concentrated. The residue was neutralized with saturated NaHCO$_3$ solution, extracted with DCM (10 ml×5), and the combined organic extracts were washed with brine, dried over NaSO$_4$, filtered and concentrated to afford crude product, which was purified by preparative TLC (7% MeOH in DCM) to afford compound 52 (26 mg, yield 93%) as a yellow solid.

m/z: [M+H]$^+$ 395.2

Synthesis of Compound 53-1

A mixture of compound 52 (26 mg, 0.065 mmol) and 5-tert-butyl-3-isocyanatoisoxazole 7 (13 mg, 0.079 mmol) in toluene (3 ml) and CCl$_4$ (1.5 ml) was stirred at 80° C. for 1 h. The reaction was concentrated to give the crude product, which was purified by preparative TLC (7% MeOH in DCM) to afford compound 53-1 (12 mg, yield 32%) as a yellow solid.

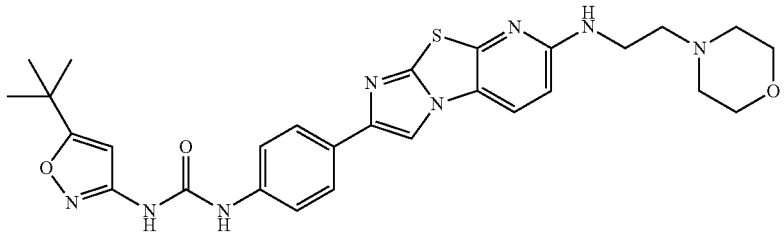

53-1 m/z: [M+H]$^+$ 561.2

$^1$HNMR (DMSO-d$_6$) δ9.54 (1H, s), 8.87 (1H, s), 8.50 (1H, s), 7.98-7.96 (1H, d, J=4.8 Hz), 7.77-7.75 (2H, d, J=8.8 Hz), 7.52-7.49 (2H, d, J=8.8 Hz), 6.96 (1H, t, J=5.6 Hz), 6.70-6.68

(1H, d, J=8.8 Hz), 6.52 (1H, s), 3.59 (4H, t, J=4.4 Hz), 3.43-3.36 (4H, m), 2.43 (4H, br), 1.30 (9H, s)

Synthesis of Compound 53-2

To a mixture of compound 53-1 (5 mg, 0.008 mmol) in MeOH (3 ml) was added 37% formaldehyde (0.04 ml) and one drop of TFA, and the mixture was stirred at rt for 4 h, then NaBH$_3$CN (28 mg, 0.445 mmol) was added. After stirred overnight, the solvent was removed under vacuum, and the mixture was diluted with DCM (20 ml), washed with water, brine, and dried over Na$_2$SO$_4$. The solvent was removed under vacuum, and the crude product was purified by preparative TLC (7% MeOH in DCM) to afford compound 53-2 (3.5 mg, yield 68%) as a white solid.

filtrate was concentrated to give crude compound 56 (410 mg, yield 90%) as a colorless oil, used in the next step without further purification.

m/z: [M+H]$^+$ 221.3

Synthesis of Compound 57

To a solution of compound 20 (316 mg, 2.00 mmol) and compound 56 (400 mg, 1.82 mmol) in acetonitrile (20 ml), was added DIPEA (469 mg, 3.63 mmol). The resulted solution was stirred 48 h at room temperature. The reaction mixture was portioned between DCM and water (20 ml, each), then the organic phase was washed by water, brine, dried over Na$_2$SO$_4$, filtered, and concentrated to give crude product, which was purified by silica gel column chromatography (0-5% MeOH in DCM) to afford compound 57 (300 mg, yield 48%) as a yellow solid.

m/z: [M+H]$^+$ 343.3

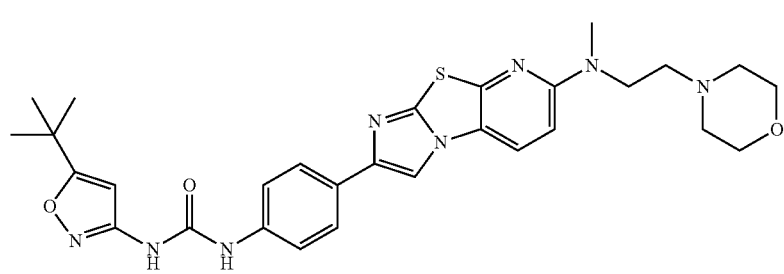

53-2 m/z: [M+H]$^+$ 575.3

Examples 34-35

Compounds 63-1 to 63-2 were Made by the Method in Scheme-3F

Synthesis of Compound 54

To a stirring ice-cooled solution of compound 21 (500 mg, 2.26 mmol) and triethylamine (457 mg, 4.52 mmol) in DCM (10 ml), was added methanesulfonyl chloride (310 mg, 2.71 mmol) dropwise. The mixture was stirred 0.5 h at 0° C., then the mixture was washed by water, and brine, the organic phase was dried over Na$_2$SO$_4$, filtered and concentrated to give the crude compound 54 (650 mg, yield 96%) as a white solid, used in the next step without further purification.

Synthesis of Compound 55

To a suspension of isoindoline-1,3-dione (540 mg, 3.67 mmol) and potassium carbonate (304 mg, 2.2 mmol) in DMSO (10 ml) at 100° C., was added compound 54 (550 mg, 1.84 mmol, dissolved in DMSO (2 ml). After the mixture was stirred 0.5 h at 100° C., the reaction mixture was cooled down, and diluted with EtOAc (50 ml). The reaction mixture was washed by water and brine, dried over Na$_2$SO$_4$, concentrated to give the crude compound 55 (620 mg, yield 96%) as a white solid, used in the next step without further purification.

Synthesis of Compound 56

A stirring solution of compound 55 (720 mg, 2.05 mmol) and hydrazine hydrate (0.5 ml in EtOH (20 ml) was refluxed for 4 h. The insoluble material was filtered off and the filtrate was concentrated to give the residue which was dissolved in DCM. After insoluble material was removed by filtration, the The Synthesis of Compound 58

To the solution of compound 57 (300 mg, 0.876 mmol) in HOAc (15 ml), was added iron powder (244 mg, 4.38 mmol). The resulted mixture was stirred at 60° C. for 1 h. The mixture was concentrated and the residue was neutralized with saturated NaHCO$_3$ solution, the aqueous phase was extracted with DCM (100 ml), and the combined organic phase was washed with water and brine, dried over Na$_2$SO$_4$, filtered and concentrated to afford crude compound 58 (250 mg, yield 91%) as a brown solid, used in the next step without further purification.

m/z: [M+H]$^+$ 313.2

Synthesis of Compound 59

To an ice-cooling stirring mixture of compound 58 (250 mg, 0.80 mmol) and KSCN (350 mg, 3.60 mmol) in HOAc (10 ml), was added bromine (191 mg, 1.2 mmol, dissolved in 2 ml HOAc) dropwise over 60 min. After the resulted mixture was stirred at room temperature for 60 min, the reaction mixture was quenched by saturated Na$_2$SO$_3$ solution and neutralized with NaHCO$_3$ solution, then the mixture was diluted by DCM (100 ml), and insoluble impurity was filtered off. The separated aqueous phase was extracted with DCM (50 ml×4), and the combined organic phase was washed with brine, dried over Na$_2$SO$_4$, filtered and concentrated to afford crude product, which was purified by silica gel column chromatography (0-5% MeOH in DCM) to afford compound 59 (26 mg, yield 29%) as a brown solid.

m/z: [M+H]$^+$ 370.3

Synthesis of Compound 60

To a solution of compound 59 (75 mg, 0.093 mmol) in EtOH (5 ml), was added 2-bromo-1-(4-nitrophenyl)ethanone 4 (22.7 mg, 0.093 mmol). After the resulted reaction solution was refluxed overnight, the reaction mixture was concentrated, and the residue was purified by preparative TLC (7% MeOH in DCM) to afford compound 60 (10 mg, yield 10%) as a yellow solid.

m/z: $[M+H]^+$ 515.2

Synthesis of Compound 61

To a stirring solution of compound 60 (10 mg, 0.019 mmol) in HOAc (5 ml), was added iron powder (10 mg, 0.194 mmol). After the resulted mixture was stirred 1 h at 60° C., the reaction mixture was cooled down to room temperature, and filtered through celite. Then the filtrate was concentrated, and the residue was neutralized with saturated NaHCO$_3$ solution, the aqueous phase was extracted with DCM (10 ml×5), and the combined organic phase was washed with brine, dried over Na$_2$SO$_4$, filtered and concentrated to afford crude compound 61 (9.0 mg, yield 96%) as a yellow solid, used in the next step without further purification.

m/z: $[M+H]^+$ 485.3

Synthesis of Compound 62

To a stirring solution of compound 61 (9.0 mg, 0.018 mmol) in toluene (3 ml) and chloroform (1.5 ml), was added 5-tert-butyl-3-isocyanatoisoxazole (3 mg, 0.018 mmol). After the mixture was stirred 1 h at 80° C., the mixture was concentrated and the residue was purified by preparative TLC (7% MeOH in DCM) to afford compound 62 (7 mg, yield 58%) as a yellow solid.

m/z: $[M+H]^+$ 651.3

Synthesis of Compound 63-1

To a stirring solution of compound 62 (7 mg, 10 umol) in HOAc (3 ml), was added 33% HBr-HOAc solution (1 ml). After the resulted mixture was stirred 1 h at room temperature, the reaction solution was partitioned between DCM (30 ml) and water (20 ml). The aqueous phase was neutralized with saturated NaHCO$_3$ solution, and extracted with DCM (10 ml×2). The combined organic phase was washed with brine, dried over Na$_2$SO$_4$, filtered and concentrated to afford crude product, which was purified by preparative TLC (15% MeOH in DCM) to afford compound 63-1 (1.2 mg, yield 21%) as a white solid.

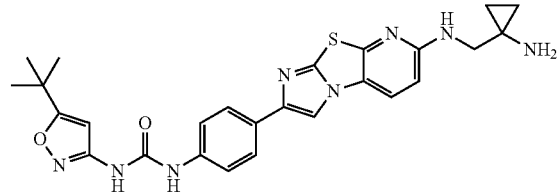

63-1 m/z: $[M+H]^+$ 517.2

Synthesis of Compound 63-2

Compound 63-2 was prepared in the same method as compound 63-1 in scheme-3-F by using the intermediate 69 instead of intermediate 56. it is a light yellow solid.

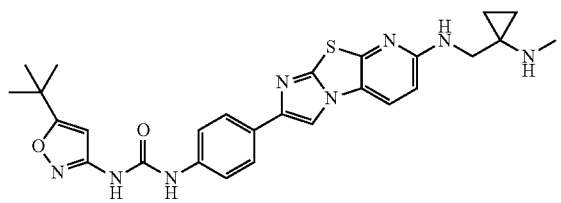

63-2 m/z: $[M+H]^+$ 531.2

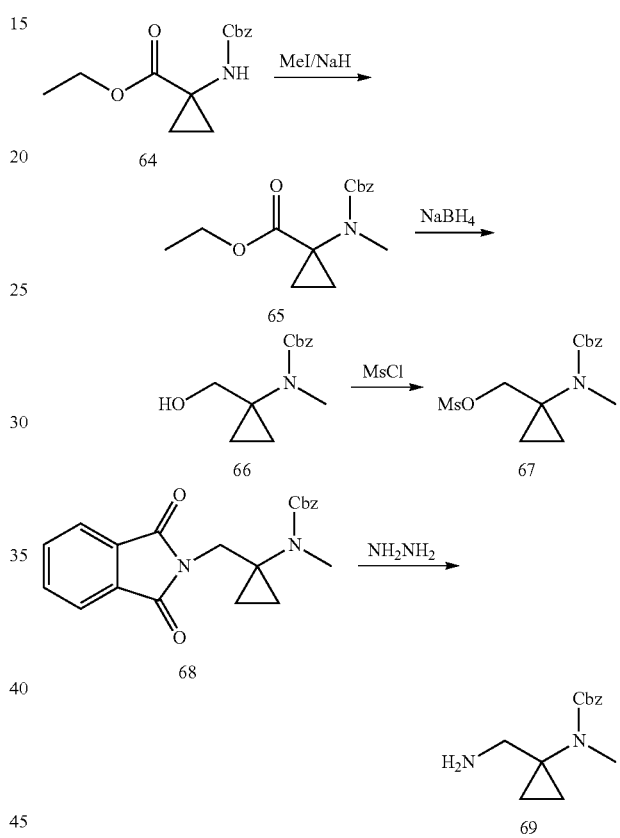

Synthesis of Compound 65

To an ice-cooling stirring solution of compound 64 (3.0 g, 11.4 mmol) in DMF (20 ml), was added NaH (0.68 g 60% 17.09 mmol) in small portion, then added MeI (0.85 ml, 13.6 mmol) dropwise. After the resulted mixture was stirred 1 h at room temperature (monitored by TLC), the mixture was diluted with EtOAc (150 ml), washed with water (50 ml×4), brine and dried over Na$_2$SO$_4$, filtered and concentrated to afford crude compound 65 (3.5 g, yield 100%) as a colorless oil, used in the next step without further purification.

Synthesis of Compound 66

To a solution of compound 65 (3.0 g, 10.8 mmol) in THF (30 ml), was added NaBH$_4$ (4.09 g, 0.18 mol). The resulted mixture was refluxed 0.5 h, then methanol (20 ml) was added dropwise at reflux, and the reaction was stirred at reflux for another 3 h. The reaction was concentrated to dryness under vacuum, water phase was extracted in EtOAc (50 ml), organic phase was washed with water (20 ml) and brine successively, dried over Na$_2$SO$_4$, filtered and concentrated to afford crude compound 66 (2.5 g, yield 98%) as a colorless oil, used in the next step without further purification.

Synthesis of Compound 67

To an ice-cooling solution of compound 66 (2.2 g, 9.35 mmol) and triethylamine (1.42 g, 14.03 mmol) in DCM (20 ml), was added Methanesulfonyl chloride (1.29 g, 11.2 mmol, dissolved in 5 ml DCM) dropwise, then resulted mixture was stirred 1 h at room temperature. The reaction solution was diluted with DCM (30 ml), washed with water (15 ml×3) and brine, dried over Na$_2$SO$_4$, filtered and concentrated to afford crude compound 67 (2.9 g, yield 99%) as a colorless oil, used in the next step without further purification.

Synthesis of Compound 68

To a suspension of Isoindoline-1,3-dione (4.23 g, 28.7 mmol) and potassium carbonate (4.63 g, 33.5 mmol) in DMSO (20 ml) at 100° C., was added compound 67 (3.0 g, 9.57 mmol, dissolved in DMSO (5 ml) dropwise. The reaction mixture was stirred for another 2 h at this temperature, then the reaction mixture cooled to room temperature and diluted with EtOAc (100 ml), washed with water (20 ml×4), brine, dried over Na$_2$SO$_4$, filtered and concentrated to give crude product, which was purified by preparative TLC (petroleum ether: EtOAc=5:1) to afford compound 68 (0.90 g, yield 26%) as a white solid, used in the next step without further purification.

Synthesis of Compound 69

A stirring solution of compound 68 (0.9 g, 2.47 mmol) and hydrazine hydrate (0.5 ml) in EtOH (10 ml) was refluxed for 2 h. The insoluble material was filtered off and the filtrate was concentrated, and then the residue was dissolved in DCM, after insoluble material was removed by filtration, the filtrate was concentrated to give crude compound 69 (550 mg, yield 95%), used in the next step without further purification.

m/z: [M+H]$^+$ 235.3

Example 36

Compound 80 was Made by the Method in Scheme-3-G

Synthesis of Compound 71

To a stirring solution of compound 70 (55.8 g, 300 mmol) in 95% EtOH (200 ml), was added aqueous NaOH (12 g, 300 mmol) (50 ml) dropwise. The reaction mixture was stirred overnight at room temperature, decompression to remove EtOH, water (300 ml) was added and the stirred. After the aqueous phase was washed with EtOAc (50 ml×2), the aqueous phase was acidified to pH 1.5 with aqueous 10% HCl and the aqueous phase was extracted with EtOAc (100 ml×3). The combined organic phase was dried over Na$_2$SO$_4$, filtered, and concentrated to give crude compound 71 (35 g, yield 73%) as a colorless oil, used directly in the next step without further purification.

Synthesis of Compound 72

To a stirring solution of compound 71 (1.0 g, 6.32 mmol) and triethylamine (0.97 ml, 7.59 mmol) in THF (18 ml) at −10° C., was added isobutyl chloroformate (0.90 ml, 6.96 mmol) dropwise. Then the reaction mixture was stirred 1 h at 0° C., the insoluble material was filtered off, and the filtrate was directly used later. To an ice-cooling solution of NaBH$_4$ (0.71 g, 18.97 mmol) in THF (10 ml) and water (2.5 ml), was added the filtrate obtained above dropwise. After the reaction mixture was allowed to stirred at 0° C. for 1 h, then reaction mixture was poured into 10% of aqueous solution HOAc, the aqueous phase was extracted with EtOAc (30 ml×3), and the combined organic phase was washed with brine, dried over Na$_2$SO$_4$, filtered and concentrated to afford crude product, which was purified by silica gel column chromatography (Petroleum ether:ethyl acetate=9:1 to 2:1) to give compound 72 (0.65 g, yield 61%) as a colorless oil.

$^1$HNMR (CDCl$_3$): δ 4.15 (2H, q, J=7.0 Hz), 3.62 (2H, s), 1.28-1.23 (5H, m), 0.86 (2H, q, J=4.2 Hz)

Synthesis of Compound 73

To a stirring ice-cooling solution of compound 72 (200 mg, 1.39 mmol) and triethylamine (280 mg, 2.77 mmol) in DCM (10 ml), was added methanesulfonyl chloride (190 mg, 1.66 mmol, dissolve in 1 ml DCM) dropwise. The reaction mixture was stirred 1 h at 0° C., then diluted with DCM (20 ml), the organic phase was washed with water and brine, dried over Na$_2$SO$_4$, filtered and concentrated to afford crude compound 73 (300 mg, yield 97%) as a colorless oil, used directly in the next step without further purification.

Synthesis of Compound 74

To a stirring solution of compound 15 (5 mg, 0.016 mmol) in DMF (1 ml), was added cesium carbonate (5 mg, 0.016 mmol) and compound 73 (5 mg, 0.016 mmol). The resulted mixture was stirred 2 h at 130° C., and the reaction mixture was cooled down to room temperature, and diluted with DCM (20 ml) and water (10 ml). the water phase was extracted with DCM (10 ml×2)), the organic phase was washed with water, brine, dried over Na$_2$SO$_4$, filtered and concentrated to afford crude product which was purified by preparative TLC (DCM) to afford compound 74 (4 mg, yield 56%) as a yellow solid.

m/z: [M+H]$^+$ 437.2

Synthesis of Compound 75

To a stirring solution of compound 74 (10 mg, 0.022 mmol) in a mixed solvent of THF (1 ml), EtOH (0.5 ml) and water (0.25 ml), was added sodium hydroxide (18 mg, 0.22 mmol). The resulted mixture was stirred for 4 h at room temperature, and then the mixture was neutralized with aqueous HCl (2 N), pH=7, the solvent was concentrated, the aqueous phase was extracted with DCM (10 ml×3), and the combined organic phase was washed with brine, dried over Na$_2$SO$_4$, filtered and concentrated to afford the crude compound 75 (27 mg, yield 97%) as a yellow solid, used directly in the next step without further purification.

m/z: [M+H]$^+$ 409.3

Synthesis of Compound 76

To a stirring solution of compound 75 (40 mg, 0.097 mmol), 4-methoxybenzyl alcohol (40 mg, 0.293 mmol) in toluene (3 ml), was added triethylamine (29 mg, 0.293 mmol) and DPPA (53 mg, 0.195 mmol).

The resulted mixture was stirred 0.5 h at room temperature, then refluxed for 3 h. The reaction mixture was concentrated and the residue was purified by preparative TLC (petroleum ether:ethyl acetate=2:1) to give compound 76 (35 mg, yield 65%) as a yellow solid.

m/z: [M+H]$^+$ 544.2

Synthesis of Compound 77

To a solution of compound 76 (35 mg, 0.064 mmol) in DMF (2 ml), was added sodium hydride (60%, 7 mg, 0.321 mmol). The resulted mixture was stirred 30 min at room temperature, then MeI (45 mg, 0.321 mmol) was added, and stirred for a another 30 min. The mixture was diluted with DCM (30 ml), washed with water, brine and dried over Na$_2$SO$_4$, filtered and concentrated to afford crude product, which was purified by preparative TLC (petroleum ether:ethyl acetate=2:1) to afford compound 77 (30 mg, yield 83%) as a yellow solid.

m/z: [M+H]$^+$ 558.2

Synthesis of Compound 78

To a stirring solution of compound 77 (30 mg, 0.053 mmol) in HOAc (2 ml), was added iron powder (60 mg, 1.08 mmol). After the reaction mixture was stirred 1 h at 60° C., the mixture was filtered through celite, and the filtrate was concentrated to dryness. The residue was neutralized with saturated sodium bicarbonate solution, and extracted with DCM (10 ml×2). The combined organic phase was washed with brine, dried over Na$_2$SO$_4$, filtered and concentrated to afford crude compound 78 (25 mg, yield 88%), used in the next step without further purification.

Synthesis of Compound 79

To a solution of compound 78 (25 mg, 0.047 mmol) in a mixed solvent of toluene (1.5 ml) and chloroform (0.5 ml), was added 5-tert-butyl-3-isocyanatoisoxazole (10 mg, 0.056 mmol). The resulted solution was stirred 2 h at 80° C., then diluted with water (10 ml), extracted with DCM (10 ml×3). The combined organic phase was washed with brine, dried over Na$_2$SO$_4$, filtered, concentrated to give the crude compound, which was purified by preparative TLC (5% MeOH in DCM) to afford desired compound 79 (8 mg, yield 24%) as a yellow solid.

m/z: [M+H]$^+$ 694.3

Synthesis of Compound 80

A solution of compound 79 (8 mg, 0.011 mmol) and trifluoroacetic acid (0.3 ml) in DCM (3 ml) was stirred 2 hr at room temperature. The reaction solution was concentrated and the residue was dissolved in DCM (10 ml), washed with saturated sodium bicarbonate solution, brine, dried over Na$_2$SO$_4$, filtered and concentrated to afford the crude product, which was purified by preparative TLC (10% MeOH in DCM) to afford compound 80 (2.4 mg, yield 39%) as a white solid.

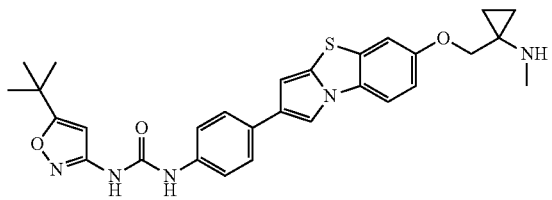

m/z: [M+H]$^+$ 530.3

Example 37

Compound 83 was Made by the Method in Scheme-3H

Synthesis of Compound 81

To a solution of compound 76 (25 mg, 0.045 mmol) in HOAc (2 ml), was added iron powder (51 mg, 0.919 mmol). After the mixture was stirred 1 h at 60° C., then the mixture was cooled down to room temperature, the solid was filtered off through celite, and the filtrate was concentrated. The residue was neutralized by aqueous saturated sodium bicarbonate, and the aqueous was extracted with DCM (10 ml×2). The combined organic phase was washed with brine, dried over Na$_2$SO$_4$, filtered and concentrated to afford crude compound 81 (20 mg, yield 84%), used directly in next step without further purification.

Synthesis of Compound 82

To a solution of compound 81 (20 mg, 0.038 mmol) in a mixed solvent of toluene (1.5 ml) and chloroform (0.5 ml), was added 5-tert-butyl-3-isocyanatoisoxazole 7 (8 mg, 0.046 mmol). After the resulted mixture was stirred 2 hr at 80° C., the reaction mixture was diluted by water (10 ml), and the aqueous was extracted with DCM (10 ml×3). The combined organic phase was washed with brine, dried over Na$_2$SO$_4$, filtered, concentrated to give the crude product, which was purified by preparative TLC (5% MeOH in DCM) to give the desired compound 82 (9 mg, yield 34%) as a yellow solid.

m/z: [M+H]$^+$ 680.3

Synthesis of Compound 83

A solution of compound 82 (9 mg, 0.013 mmol) and trifluoroacetic acid (0.2 ml) in DCM (2 ml) was stirred at room temperature for 0.5 h. The mixture was concentrated and the residue was dissolved in DCM (10 ml), washed with aqueous saturated sodium bicarbonate, brine, dried over Na$_2$SO$_4$, filtered and concentrated to afford crude product, which was purified by preparative TLC (10% MeOH in DCM) to afford compound 83 (1.2 mg, yield 17%) as a white solid.

m/z: [M+H]$^+$ 516.3

Examples 38-41

Compounds 89-1, 89-3, 89-4, and 89-5 were Made by the Method in Scheme-3-I

| Compound | R' | LCMS m/z: [M + H]+ |
|---|---|---|
| 89-1 | -NH-CH2CH2-N(CH3)2 | 519.3 |
| 89-3 | -NH-CH2CH2-N(Et)2 | 547.3 |
| 89-4 | -NH-CH2CH2-N(morpholine) | 573.3 |
| 89-5 | -N(piperidine)-N(morpholine) | 601.3 |

Synthesis of Compound 84

To a stirring solution of compound 20 (5.0 g, 31.5 mmol) in acetic acid (50 ml) was added iron powder (8.8 g, 157.6 mmol) in small portion at room temperature, the reaction was exothermic and the temperature rise to 80° C., end of added and kept the temperature at 40-50° C. and stirred for 2 h. The reaction was filtered through celite and washed with little acetic acid, the filtrate was evaporated to dryness, adjusted pH=8 with saturated solution of sodium bicarbonate, extracted with dichloromethane (100 ml×5). The combined organic phase was washed with brine, dried over $Na_2SO_4$, filtered and concentrated to afford crude compound 84 (3.9 g, yield 96%) as a brown solid, used directly in next step without further purification.

Synthesis of Compound 85

Compound 84 (2.5 g, 19.4 mmol) and potassium thiocyanate (8.5 g, 37.5 mmol) were dissolved in acetic acid (25 ml). To this solution was added dropwise a solution of bromine (1.5 ml, 29.2 mmol in acetic acid 10 ml) for about 60 min, the resulted mixture was stirred at room temperature for overnight, then water (20 ml) was added. The reaction mixture was stirred and filtered at 85° C., the filtered cake was washed by acetic acid. The obtained filtrate was concentrated to ⅓ volume, neutralized with aqueous ammonia solution to pH=6, the precipitate was collected by filtration to afford crude compound 85 (2.5 g, yield 69%) as a yellow solid, used directly in next step without further purification.

Synthesis of Compound 86

To a stirring solution of compound 85 (1.4 g, 7.5 mmol) in n-butanol (15 ml) was added 2-bromo-1-(4-nitrophenyl)ethanone 4 (2.02 g, 8.3 mmol) and sodium bicarbonate (0.63 g, 7.5 mol), the resulted mixture was stirred at refluxing for 4 h, then the reaction was cooled down to room temperature, filtered to afford the crude compound 86 (1.06 g, yield 42%) as a yellow solid, used directly in next step without further purification.
m/z: [M+H]+ 331.1

Synthesis of Compound 87

To a suspension of compound 86 (1.0 g, 3.02 mmol) in acetic acid (200 ml) was added iron powder (0.88 g, 15.8 mmol) in one portion at room temperature, the resulted mixture was stirred at 60° C. for 5 h. The reaction was filtered through celite. The filtrate was concentrated and neutralized with sodium bicarbonate, the water phase was extracted with DCM (100 ml×3) which include little MeOH, The combined organic phase was washed with brine and dried over $Na_2SO_4$, filtered and concentrated to afford crude compound 87 (0.26 g, yield 28%) as a brown solid, used directly in next step without further purification.
m/z: [M+H]+ 301.2

Synthesis of Compound 88-1

A solution of compound 87 (80 mg, 0.26 mmol) in $N_1,N_1$-dimethylethane-1,2-diamine (5 ml) was stirred at 125° C. for 3 days, then the mixture was evaporated to dryness, the residues was dissolved in ethyl acetate (100 ml) and washed sequentially with a saturated solution of ammonium chloride and brine. The organic phase was dried over $Na_2SO_4$, filtered and concentrated. The residue was purified by preparative TLC (6% methanol in dichloromethane) to afford compound 88-1 (60 mg, yield 64%) as a white solid.
m/z: [M+H]+ 353.3

Synthesis of Compound 88-2

A mixture of compound 87 (40 mg, 0.13 mmol) in DMSO (1 ml) and DMF (0.5 ml), potassium carbonate (90 mg, 0.66 mol) and (1S,4S)-2-oxa-5-azabicyclo[2.2.1]heptane (54 mg, 0.40 mmol) was added, stirred at 125° C. for 5 days. The reaction was cooled down to room temperature, diluted with ethyl acetate, washed with water (20 ml×3) and brine, dried over $Na_2SO_4$, filtered and concentrated, the residue was purified by preparative TLC (5% methanol in dichloromethane) to afford compound 88-2 (20 mg, yield 41%) as an off-white solid.
m/z: [M+H]+ 364.3

Synthesis of Compound 89-1

A solution of compound 88-1 (60 mg, 0.17 mmol) and 5-(tert-butyl)-3-isocyanatoisoxazole 7 (31 mg, 0.18 mmol) in a mixed solvent of toluene (5 ml) and chloroform (1 ml) was stirred at 80° C. for 2 h. The reaction mixture was filtered, the filtered cake was recrystallized from dichloromethane/toluene to afford compound 89-1 (45 mg, yield 51%) as a white solid.

Examples 42-44

Compounds 97-1 to 97-3 were Made by the Method in Scheme 4-A

| Compound | R | LCMS m/z: [M + H]$^+$ |
|---|---|---|
| 97-1 | -N(CH₃)₂ (dimethylamino) | 520.3 |
| 97-2 | -N(Et)₂ (diethylamino) | 548.3 |
| 97-3 | oxa-bridged piperidinyl | 574.3 |

Synthesis of Compound 91

To an ice-cooling solution of 2-chloro-5-nitro-4-thiocyanatopyrimidine (compound 1) (520 mg, 2.4 mmol) in toluene (10 ml) was added a solution of 2,2-dimethoxyethanamine (compound 90) (378 mg, 3.6 mmol) in ethanol (1 ml), the resulted mixture was stirred at room temperature for 1 h, then the mixture was filtered to afford compound 91 (650 mg, yield 95%) as a white solid, used directly in next step without further purification.

Synthesis of Compound 92

To a solution of compound 91 (630 mg, 2.21 mmol) in acetic acid (10 ml) was added iron powder (616 mg, 11.04 mmol) in one portion at room temperature, the resulted mixture was stirred at 60° C. for 1 h. The mixture was filtered through celite, the filtrate was evaporated to dryness, the residue was dissolved in dichloromethane contained 20% methanol (50 ml), adjusted pH=8 with saturated solution of sodium bicarbonate, the insoluble residue was filtered off. The filtrate was washed with sodium bicarbonate solution, brine, dried over Na$_2$SO$_4$, filtered and concentrated to afford crude compound 92 (350 mg, yield 62%) as a deep brown solid, used directly in next step without further purification.
m/z: [M+H]$^+$ 256.1

Synthesis of Compound 93

A mixture of compound 92 (150 mg, 0.58 mmol) and 2-bromo-1-(4-nitrophenyl)ethanone 4 (143 mg, 0.58 mmol) in ethanol (5 ml) was stirred at 60° C. for overnight, refluxed at 100° C. for 3 h, then the reaction mixture was cooled down to room temperature, filtered to afford crude compound 93 (120 mg, yield 51%) as a yellow solid, used directly in next step without further purification.
m/z: [M+H]$^+$ 401.1

Synthesis of Compound 94

To a stirring solution of compound 93 (500 mg, 1.25 mmol) in acetic acid (20 ml) was added zinc powder (408 mg, 6.24 mmol) at room temperature, the resulted mixture was stirred at 60° C. for 1 h. The mixture was filtered through celite, the filtrate was evaporated to dryness, neutralized with saturated solution of sodium bicarbonate, then the aqueous phase was extracted with dichloromethane contained 10% methanol (100 ml). The organic phase was washed with brine, dried over Na$_2$SO$_4$, filtered and concentrated to afford crude compound 94 (150 mg, yield 32%) as a brown solid, used directly in next step without further purification.

Synthesis of Compound 95

A mixture of compound 94 (50 mg, 0.13 mmol) and 5-(tert-butyl)-3-isocyanatoisoxazole 7 (24 mg, 0.14 mol) in a mixed solvent of toluene (5 ml), chloroform (1 ml) and 1,4-dioxane (1.5 ml) was stirred at 80° C. for 2 h. The mixture was concentrated, then the residue was purified by preparative TLC (7% methanol in dichloromethane) to afford compound 95 (50 mg, yield 51%) as a yellow solid.
m/z: [M+H]$^+$ 537.3

Synthesis of Compound 97-1

Compound 95 (15 mg, 0.03 mmol), dimethylamine hydrochloride (25 mg, 0.30 mmol) and zinc(II) chloride (20 mg) were dissolved in a mixed solvent of methanol (2.0 ml) and dichloromethane (1 ml), the resulted mixture was stirred at room temperature for 2 h, then sodium cyanoborohydride (20 mg, 0.30 mmol) was added to the solution and stirred for overnight. The reaction was added water (5 ml), and the reaction mixture was extracted with dichloromethane contained 20% methanol (5 ml×3). The combined organic phase was dried over Na$_2$SO$_4$, filtered and concentrated. The residue was purified by preparative TLC (15% methanol in dichloromethane) to afford compound 97-1 (6 mg, yield 37%) as a yellow solid.
m/z: [M+H]$^+$ 520.3

Compound 97-2 and 97-3 were prepared according to the method of 97-1 in scheme 4-A and the results were listed in the above table.

The Biological Assays:

The following representative assays (but not limited to) were performed in assessing the biological activities disclosed herein.

1. MV4-11 Cell Proliferation Assay

The effect of test compounds on cancer cell viability was tested in MV4-11 cell (ATCC, CRL-9591), a human leukemia cell line expressing constitutive active FLT3 receptor and contains internal tandem duplications (ITD) found in the AML patients. MV4-11 cells were plated in 96 well plates at 15,000 cells per well in 100 ul IMDM medium (Invitrogen, 12440-053) containing 10% fetal bovine serum. Test compounds were prepared in 100% DMSO and added to the cells to achieve final concentrations from 0.2 uM to 0.000001 uM (10 concentration points in 3 fold serial dilution). The culture plates were then incubated at 37 C in 5% $CO_2$ for 72 hours.

After 72 hours, the cell morphology was observed under an inverted microscope. Cell viability was then quantified at room temp using a CellTiter-Glo assay (Promega G7571) following the manufacture's instruction. Briefly, a volume of 100 ul Celltiter-Glo reagenet was added to each well to induce cell lysis. After 10 min incubation at RT, a luminescent signal was produced by measuring the amount of ATP. The signal was directly proportional to the number of viable cells present in culture.

The $IC_{50}$ values of compounds of the present invention in inhibiting MV4-11 cell proliferation are listed in following table 1.

TABLE 1

| Examplary compound | $IC_{50}$(nM) |
| --- | --- |
| compound 8-4 | 1.1 |
| compound 8-6 | 1.26 |
| compound 28-1 | 0.7 |
| compound 28-2 | 0.2 |
| compound 28-3 | 0.4 |
| compound 28-4 | 0.4 |
| compound 28-6 | 0.4 |
| compound 28-7 | 0.3 |
| compound 28-8 | 0.2 |
| compound 28-9 | 0.3 |
| compound 28-10 | 0.3 |
| compound 28-11 | 0.84 |
| compound 28-12 | 0.47 |
| compound 28-13 | 0.3 |
| compound 28-14 | 0.03 |
| compound 28-15 | 0.05 |
| compound 35-1 | 1.4 |
| compound 35-2 | 0.52 |
| compound 35-3 | 12.9 |
| compound 35-4 | 0.9 |
| compound 39-1 | 0.5 |
| compound 39-2 | 0.09 |
| compound 39-3 | 1.8 |
| compound 46 | 0.8 |
| compound 53-1 | 0.2 |
| compound 53-2 | 0.5 |
| compound 63-1 | 0.96 |
| compound 63-2 | 0.58 |
| compound 80 | 4.7 |
| compound 83 | 5.8 |
| compound 89-1 | 0.03 |
| compound 89-3 | 0.04 |
| compound 89-4 | 0.08 |
| compound 89-5 | 0.29 |
| Compound 97-1 | 0.03 |
| Compound 97-2 | 0.42 |
| Compound 97-3 | 0.07 |
| Quizartinib (positive control) | 0.56 |

Table 1 showed that most of the compounds of the present invention have the better MV4-11 cell proliferation inhibitory activities than Quizartinib.

2. FLT3 Kinase Inhibition Assay

FLT3 is a receptor tyrosine kinase involved in survival and proliferation of leukemic cells. Constitutively activating FLT3 mutations has been found in about 30% of all patients with acute myeloid leukemia (AML). The tested compounds were screened for their ability to inhibit FLT3 kinase activity using Caliper's mobility shift assay (MSA). The assay uses a microfluidic chip to measure the conversion of a fluorescent peptide substrate to a phosphorylated product following separation by electrophoresis. The signature of the fluorescence signal over time reveals the extent of the reaction.

Protein tyrosine kinase assays were carried out in a final volume of 25 ul containing 0.9 nM purified FLT3 (Carna, Cat 08-154) enzyme protein, 50 mM HEPES [pH=7.5], 0.0015% Brij-35, 10 mM $MgCl_2$, 2 mM DTT, 2% DMSO, 97 uM ATP, 1.5 uM peptide 2. Each Compound was added into the reaction to final concentrations from 300 nM to 0.015 nM (10 concentration points in 3 fold serial dilution). The assay was carried out in 384 well plates at 28° C. for 60 min and terminated by adding 25 ul stop buffer (containing 100 mM HEPES [pH=7.5], 0.015% Brij-35, 0.2% Coating Reagent #3, 50 mM EDTA). Data were collected on Caliper and converted into inhibition values. $IC_{50}$ values were obtained using XLfit graphic program.

$IC_{50}$ values of the compounds of the present invention in inhibiting the FLT3 kinase are listed in following table 2.

TABLE 2

| Examplary compound | $IC_{50}$ (nM) |
| --- | --- |
| compound 8-1 | 19 |
| compound 28-2 | 18 |
| compound 28-3 | 34 |
| compound 28-4 | 33 |
| compound 28-6 | 47 |
| compound 28-7 | 1.2 |
| compound 28-8 | 10.9 |
| compound 28-9 | 11 |
| compound 28-10 | 13 |
| compound 28-14 | 9.6 |
| compound 28-15 | 68 |
| compound 35-1 | 38 |
| compound 39-1 | 52 |
| compound 39-2 | 56 |
| compound 53-1 | 29 |
| compound 53-2 | 43 |
| Compound 89-1 | 10 |
| Compound 89-3 | 19 |
| Compound 89-4 | 28 |
| Compound 89-5 | 34 |
| Quizartinib (positive compound) | 72 |

Table 2 showed that most of the compounds of the present invention have the better FLT3 kinase inhibitory activities than Quizartinib.

3. The present invention compound(C) (3 mg/kg, po, qd) was evaluated in MV4-11 acute myeloid leukemia zenograft tumor model, Quizartinib (B) (3 mg/kg, po, qd)) used as a positive control.

Compound C (18 mg) in 22% 2-hydroxypropyl-β=cyclodextrin (60 ml), ultrasonic 15 min to dissolve, an average of 2.14 ml divided into each of the small bottle, reserved 22 bottles for experiment.

6-8 weeks NOD/SCID female mice (18-25 g) were used. Each mouse was inoculated subcutaneously at the right flank with MV4-11 tumor cells ($1\times10^7$) in 0.1 ml of PBS/Matrigel (1:1) for tumor development. The treatments were started when the mean tumor size reached 188 $mm^3$. The animals were separated even as test and control group randomly, and each group is consisted of 6 tumor-bearing mice. The test articles were orally administered (2.14 ml) to the tumor-bearing mice once a day. The date of tumor cell inoculation is denoted as day 0. The tumor volume was measured every four days, and the animals were scarified at 22 days. Statistical analyses of difference in tumor volume among the groups were evaluated using a one-way ANOVA followed by individual comparisons using Games-Howell (equal variance not assumed).

All data were analyzed using SPSS 17.0. p<0.05 was considered to be statistically significant. The antitumor activities of compounds of disclose are calculated by the formula: T C %=TRTV/CRTV×100%. (TRTV: drug treated group RTV; CRTV: vehicle treated group RTV). Evaluation standard: T/C (%)>40% considered as not effective; T/C (%) 40% considered as effective with P<0.05.

FIG. 1 showed the antitumor effect in MV4-11 acute myeloid leukemia zenograft tumor model assay of the exemplary compound of the present invention, where the mean tumor volume of the mice treated with either vehicle (A), positive control compound Quizartinib (B), or the exemplary compound (C) of the present invention is measured and plotted versus the dosing days. It can be seen that the present invention compound (C) (3 mg/kg, po, qd, 22 days) has demonstrated T/C=8% (P=0.011), compared to the positive control compound Quizartinib (B) (3 mg/kg, po, qd, 22 days) with T/C=9% (P=0.01), that means the exemplary compound (C) of the present invention may have the better antitumor effect in this model testing.

The invention claimed is:
1. A Compound of formula (I) or a pharmaceutically acceptable salt thereof,

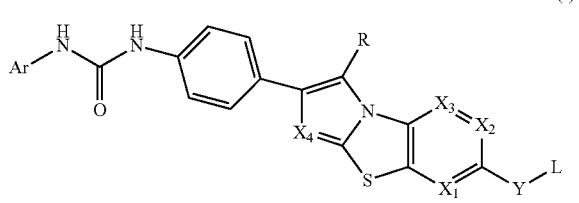

(I)

Ar is

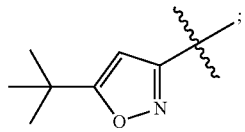 [SMILES: *c1cc(C(C)(C)C)on1]

L is H, optionally substituted or unsubstituted alkyl, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl; when substituted, the substituents are one or more groups independently selected from the group consisting of alkyl, cycloalkyl, cycloalkylalkyl, heterocycloalkyl, heterocycloalkylalkyl, amino, aminoalkyl, amido, aminocarbonyl, sulfonamido, acyl, hydroxyl, hydroxylalkyl, alkoxyl, —NHalkylhydroxyl, —NHalkoxyalkyl, —NHcycloalkyl, —NHcycloalkylalkyl, or —NHheterocycloalkyl;

Y is O, $NR_2R_2'$ or a direct bond;

$X_1$, $X_2$, $X_3$ and $X_4$ are independently N or $CR_1$; but when $X_4$ is N or $CR_1$, $X_1$, $X_2$, $X_3$ are not $CR_1$ at the same time; $R_1$ is H;

R is hydrogen;

$R_2$ and $R_2'$ are each independently selected from the group consisting of hydrogen, alkyl, cycloalkyl, or $R_2$, $R_2'$ together with the nitrogen atom to which they are attached, formed a 3- to 7-membered heterocycloalkyl ring, and the hetero atom is selected from at least one of O or N atoms, the 3- to 7-membered heterocycloalkyl ring is further optionally substituted with a group independently selected from alkyl, cycloalkyl, methylsulfonyl, acyl, or heterocycloalkyl.

2. The compound of formula (I) or a pharmaceutically acceptable salt thereof according to claim 1, wherein:
Ar is

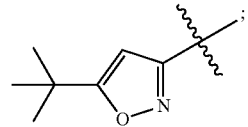 [SMILES: *c1cc(C(C)(C)C)on1]

L is H, optionally substituted or unsubstituted alkyl, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl; when substituted, the substituents are one or more groups independently selected from the group consisting of alkyl, cycloalkyl, cycloalkylalkyl, heterocycloalkyl, heterocycloalkylalkyl, amino, aminoalkyl, amido, aminocarbonyl, sulfonamido, acyl, hydroxyl, hydroxylalkyl, alkoxyl, —NHalkylhydroxyl, —NHalkoxyalkyl, —NHcycloalkyl, —NHcycloalkylalkyl, or —NHheterocycloalkyl;

Y is O or $NR_2R_2'$;

$X_1$ is N, $X_3$ is $CR_1$, $X_2$, $X_4$ are independently N or $CR_1$, $R_1$ is H;

R is hydrogen;

$R_2$ and $R_2'$ are each independently selected from the group consisting of hydrogen or alkyl, or $R_2$, $R_2'$ together with the nitrogen atom to which they are attached, formed a 3- to 7-membered heterocycloalkyl ring, and the hetero atom is selected from at least one of O or N atoms, the 3- to 7-membered heterocycloalkyl ring is further optionally substituted with a group independently selected from alkyl, cycloalkyl, methylsulfonyl, acyl, or heterocycloalkyl.

3. The compound of formula (I) or a pharmaceutically acceptable salt thereof according to claim 1, wherein:
Ar is

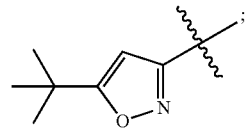 [SMILES: *c1cc(C(C)(C)C)on1]

L is optionally substituted or unsubstituted alkyl, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl; when substituted, the substituents are one or more groups independently selected from the group consisting of alkyl, cycloalkyl, cycloalkylalkyl, heterocycloalkyl, heterocycloalkylalkyl, amino, aminoalkyl, amido, aminocarbonyl, sulfonamido, acyl, hydroxyl, hydroxylalkyl, alkoxyl, —NHalkylhydroxyl, —NHalkoxyalkyl, —NHcycloalkyl, —NHcycloalkylalkyl, or —NHheterocycloalkyl;

Y is O;
X₁ is N, X₃ is CH, X₂, X₄ are independently N or CH;
R is hydrogen.

4. The compound of formula (I) or a pharmaceutically acceptable salt thereof according to claim 1, wherein:
Ar is

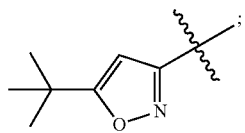 [SMILES: *c1cc(C(C)(C)C)on1]

L is H, optionally substituted or unsubstituted alkyl, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl; when substituted, the substituents are one or more groups independently selected from the group consisting of alkyl, cycloalkyl, cycloalkylalkyl, heterocycloalkyl, heterocycloalkylalkyl, amino, aminoalkyl, amido, aminocarbonyl, sulfonamido, acyl, hydroxyl, hydroxylalkyl, alkoxyl, —NHalkylhydroxyl, —NHalkoxyalkyl, —NHcycloalkyl, —NHcycloalkylalkyl, or —NHheterocycloalkyl;

Y is NR₂R₂';

R₂, R₂' is hydrogen or alkyl, or R₂, R₂' together with the nitrogen atom to which they are attached, formed a 3- to 7-membered heterocycloalkyl ring, and the hetero atom is selected from at least one of O or N atoms, the 3- to 7-membered heterocycloalkyl ring is further optionally substituted with a group independently selected from alkyl, cycloalkyl, methylsulfonyl, acyl, or heterocycloalkyl;

X₁ is N, X₃ is CH, X₂, X₄ are independently N or CH;
R is hydrogen.

5. The compound of formula (I) or a pharmaceutically acceptable salt thereof according to claim 1, wherein:
Ar is

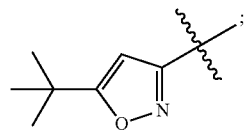 [SMILES: *c1cc(C(C)(C)C)on1]

L is optionally substituted or unsubstituted alkyl, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl; when substituted, the substituents are one or more groups independently selected from the group consisting of alkyl, cycloalkyl, cycloalkylalkyl, heterocycloalkyl, heterocycloalkylalkyl, amino, aminoalkyl, amido, aminocarbonyl, sulfonamido, acyl, hydroxyl, hydroxylalkyl, alkoxyl, —NHalkylhydroxyl, —NHalkoxyalkyl, —NHcycloalkyl, —NHcycloalkylalkyl, or —NHheterocycloalkyl;

Y is a direct bond;
X₁ is N, X₃ is CH, X₂, X₄ are independently N or CR₁; R₁ is H;
R is hydrogen.

6. The compound according to claim 1, which is selected from the following compounds consisting of,

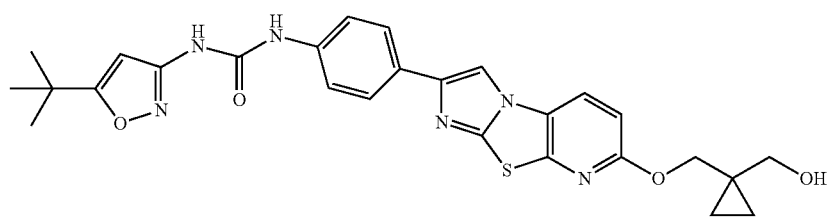

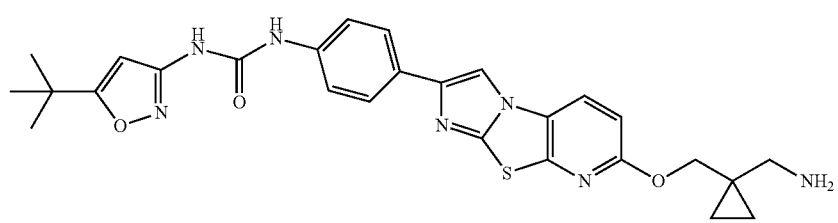

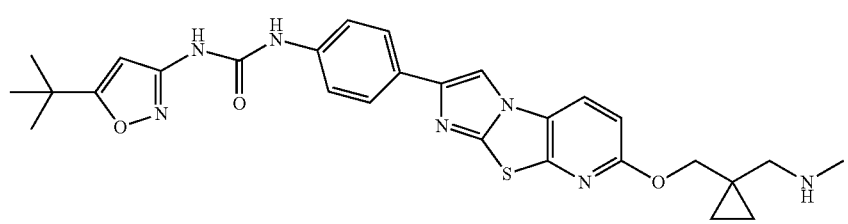

-continued
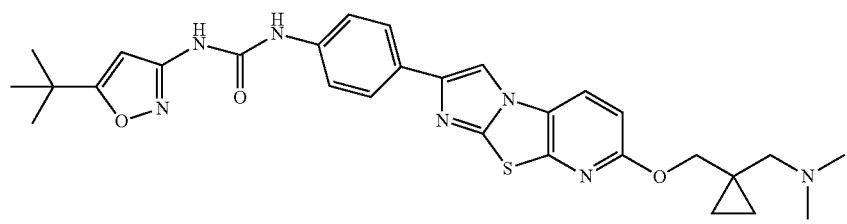
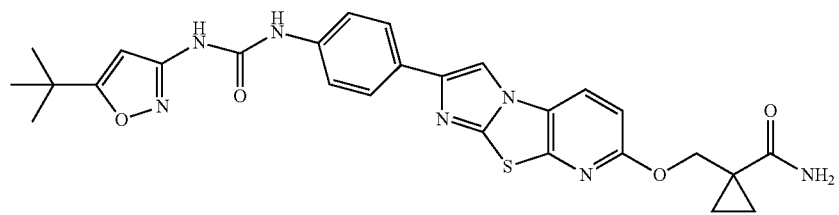
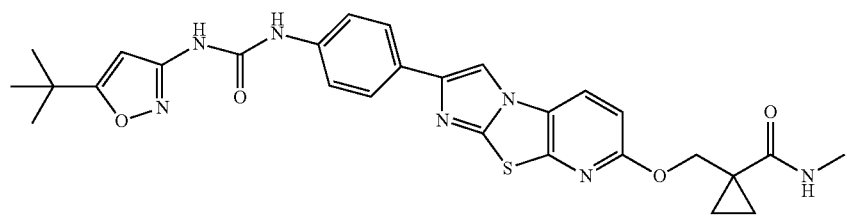
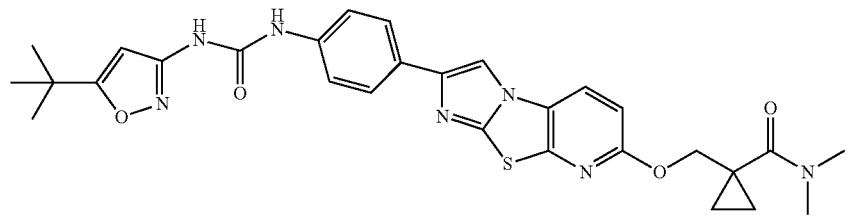
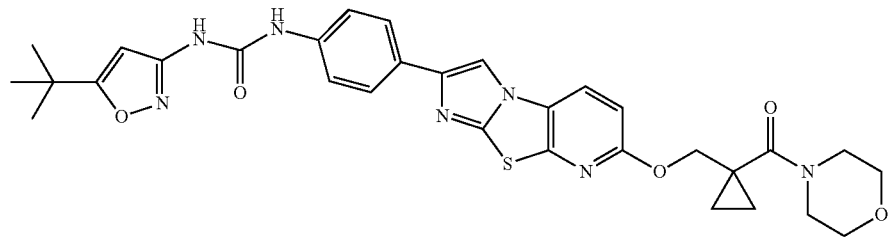
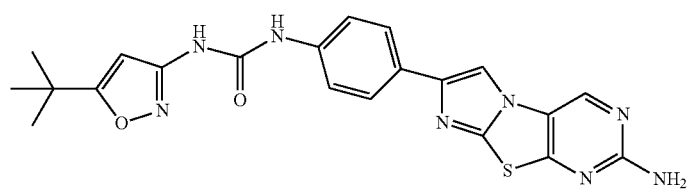
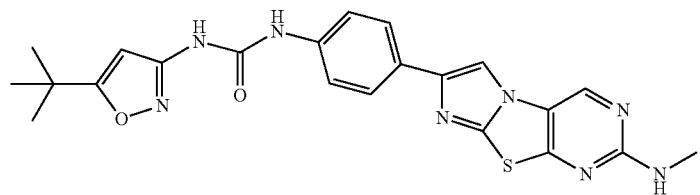
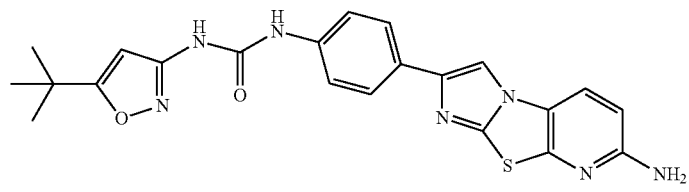

-continued
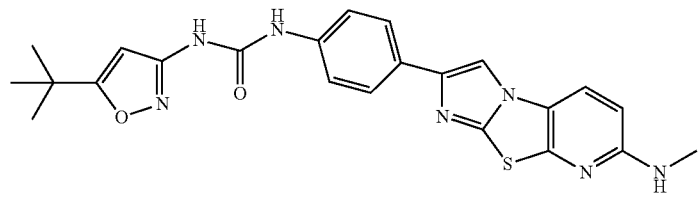
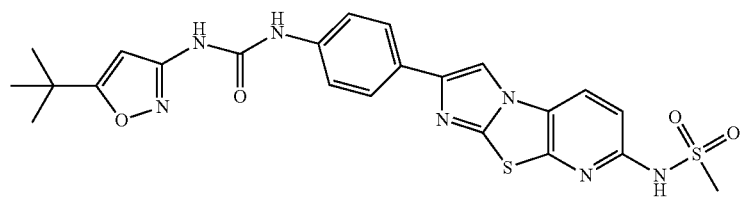
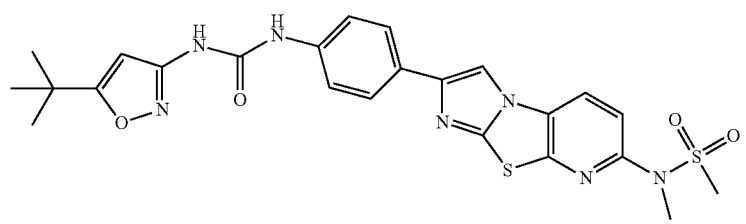
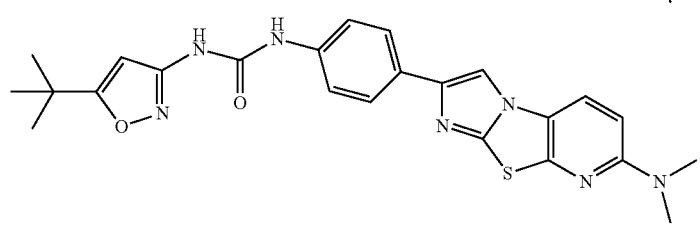
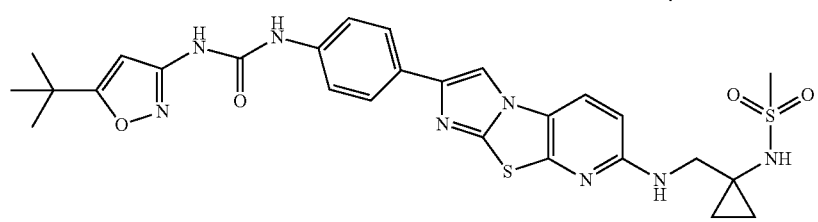
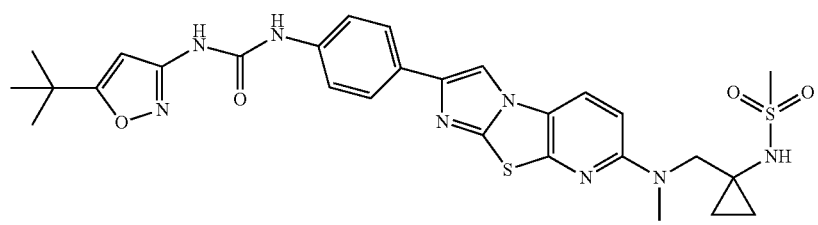
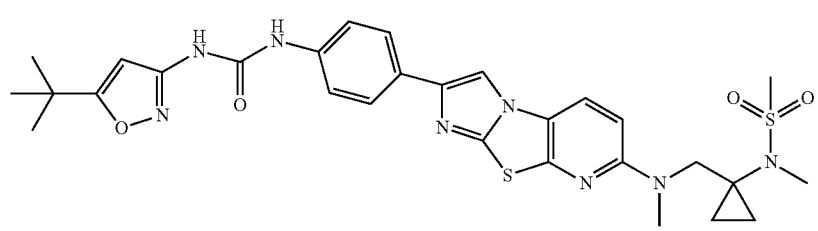
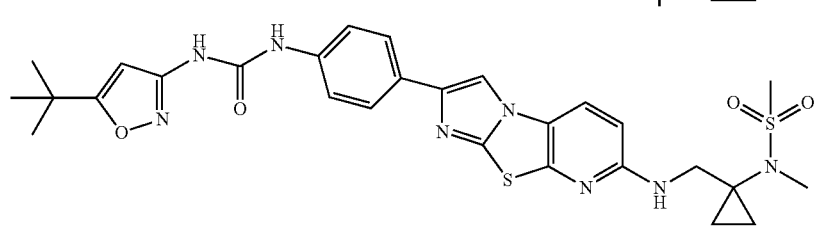

-continued
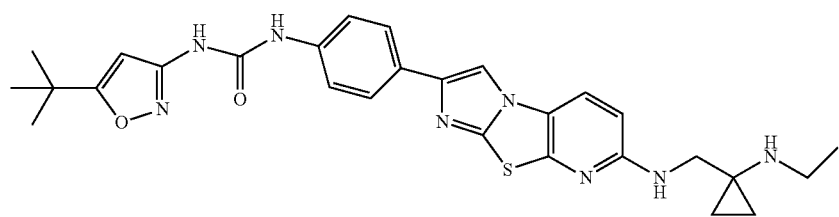
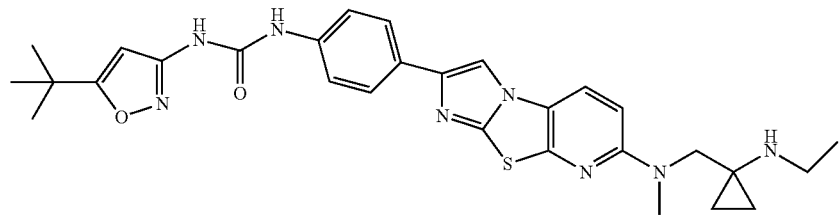
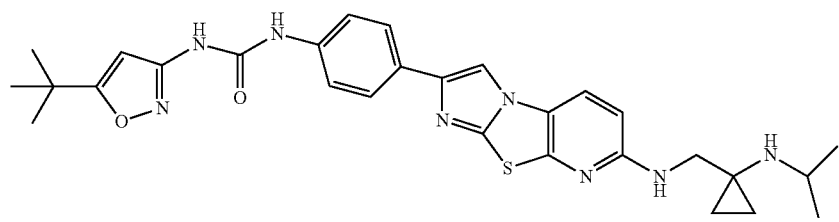
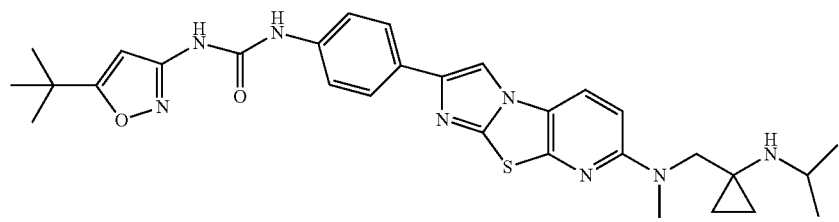
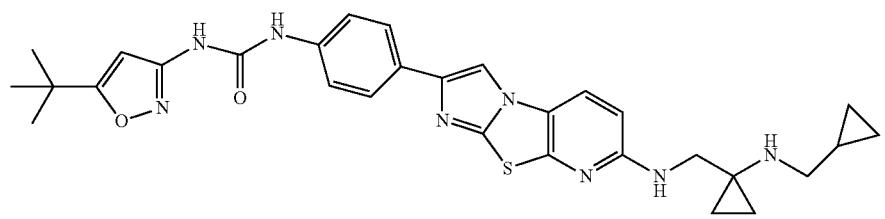
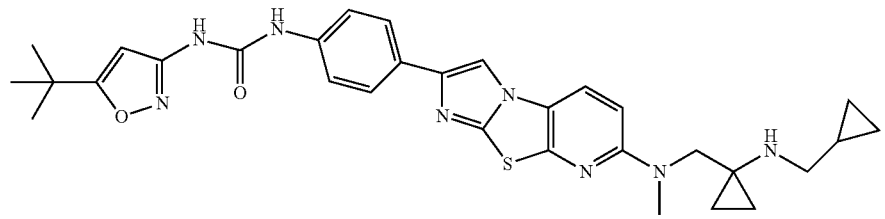
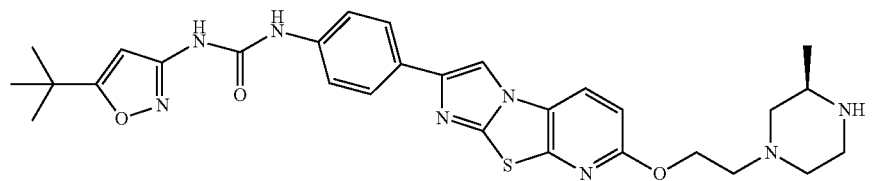
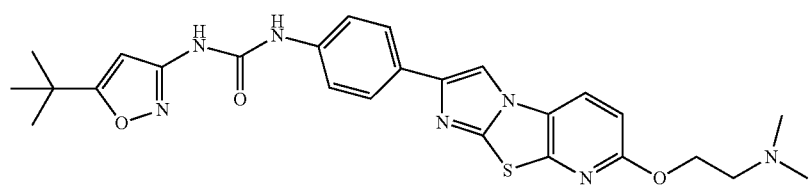

-continued
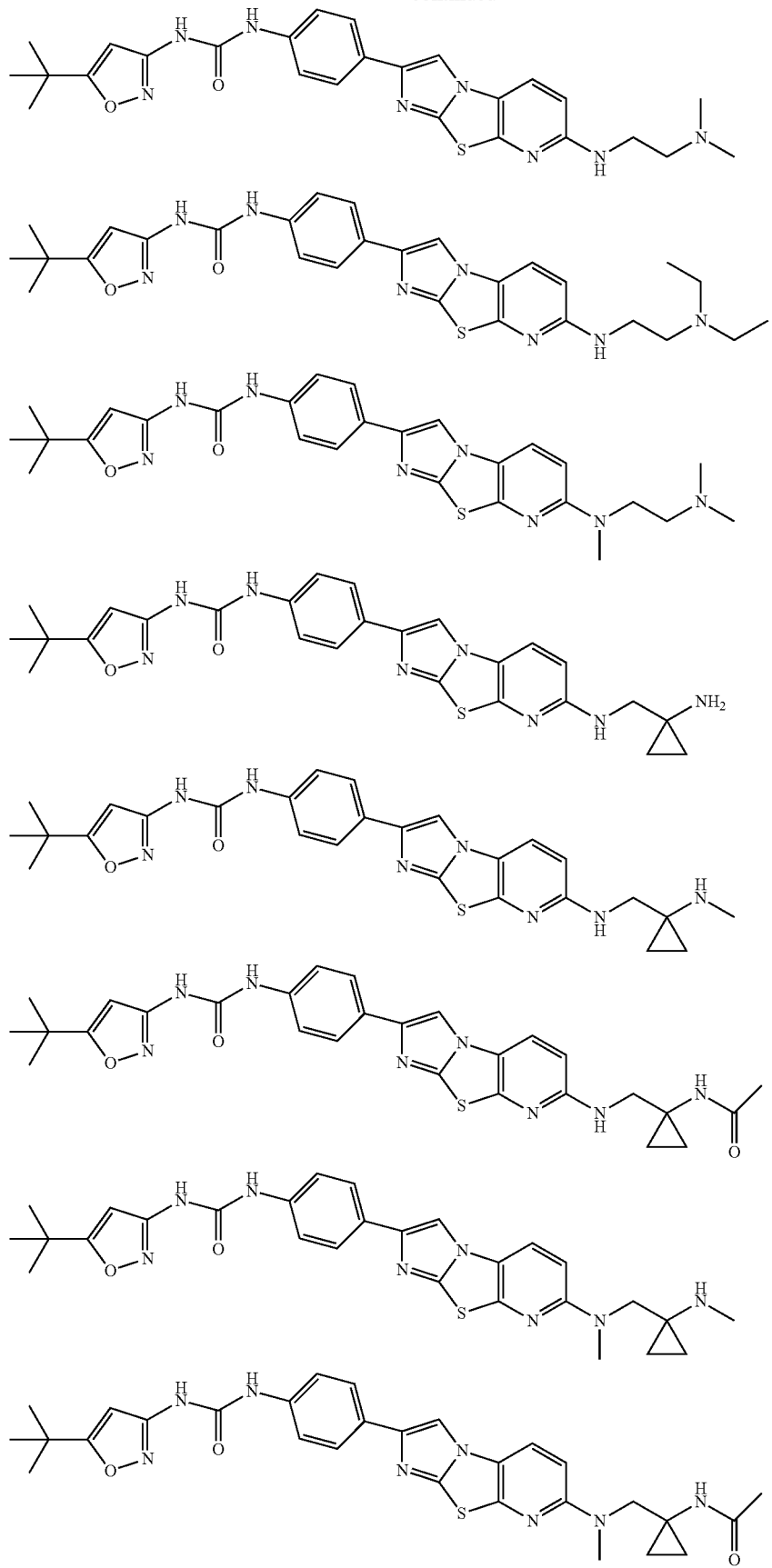

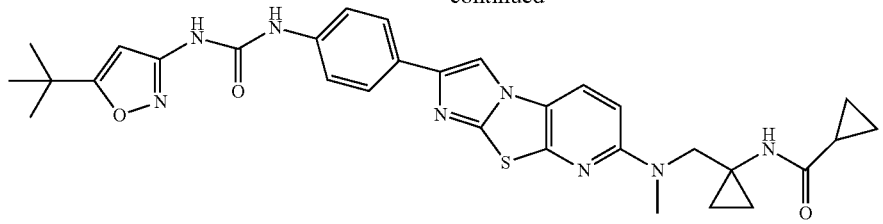
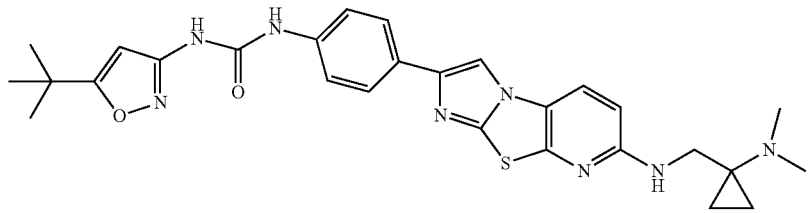
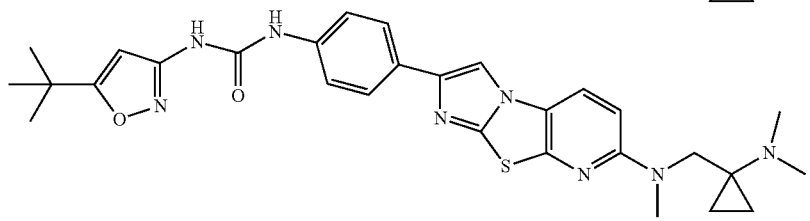
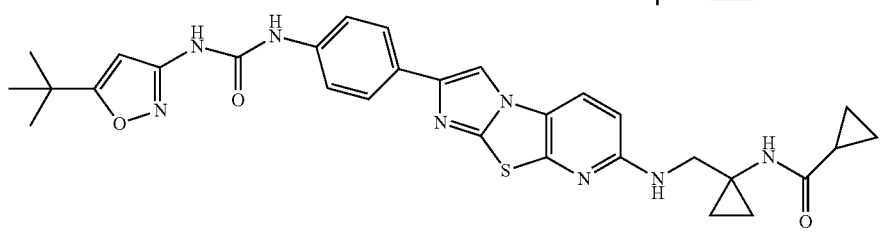
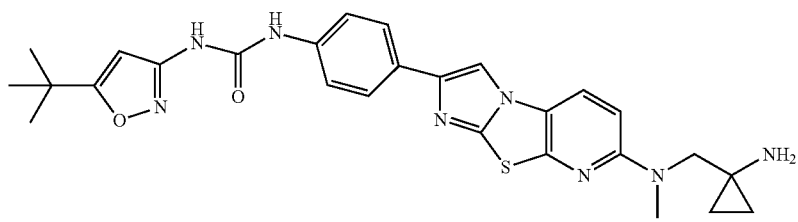
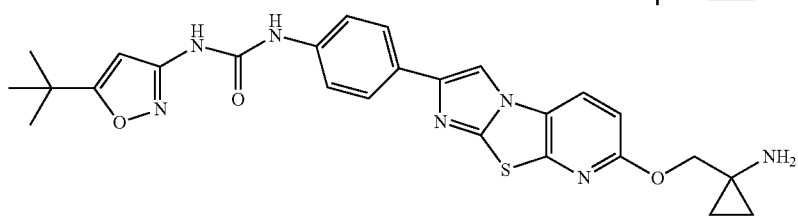
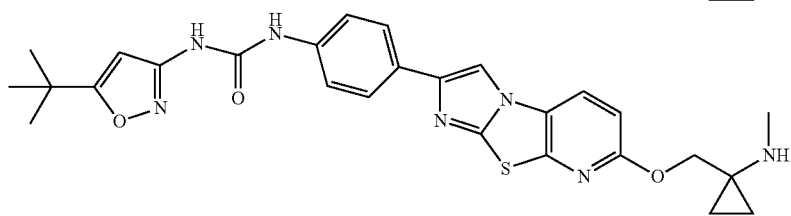
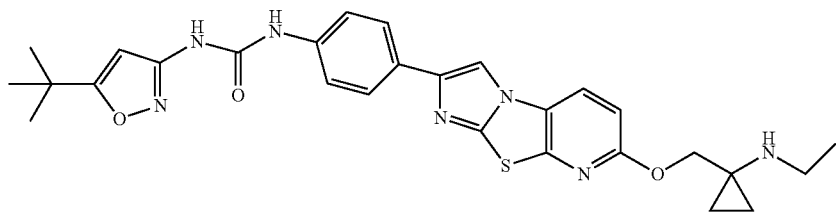

-continued
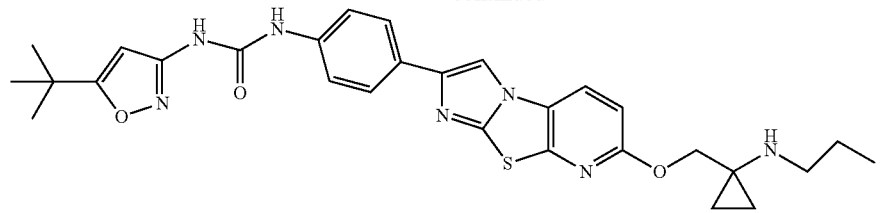
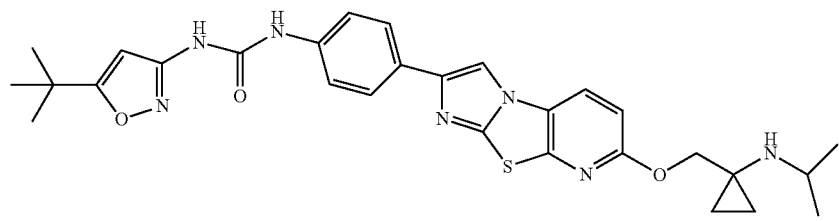
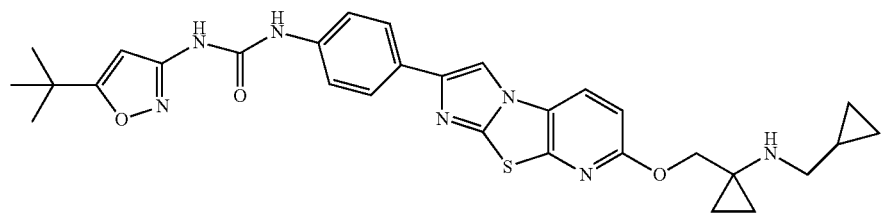
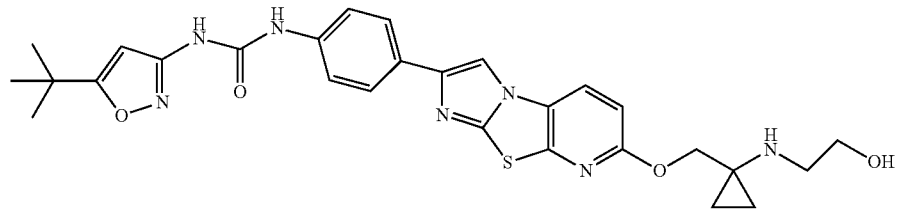
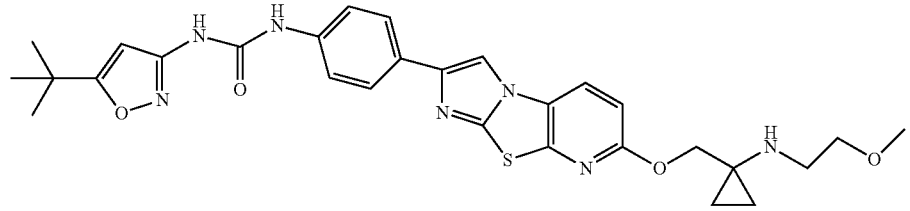
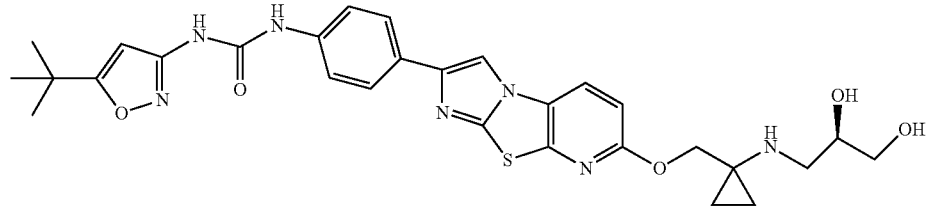
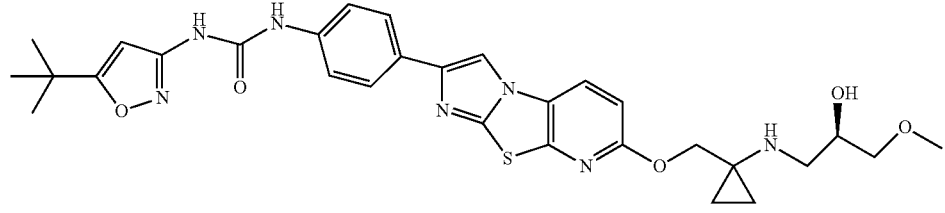
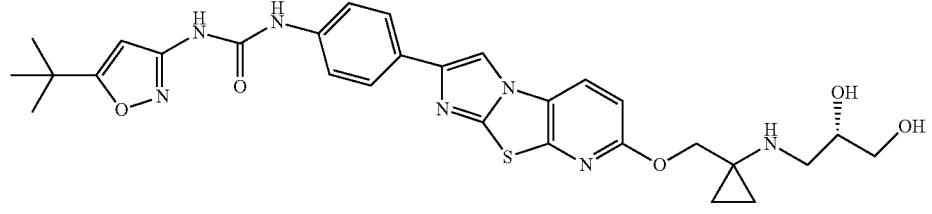

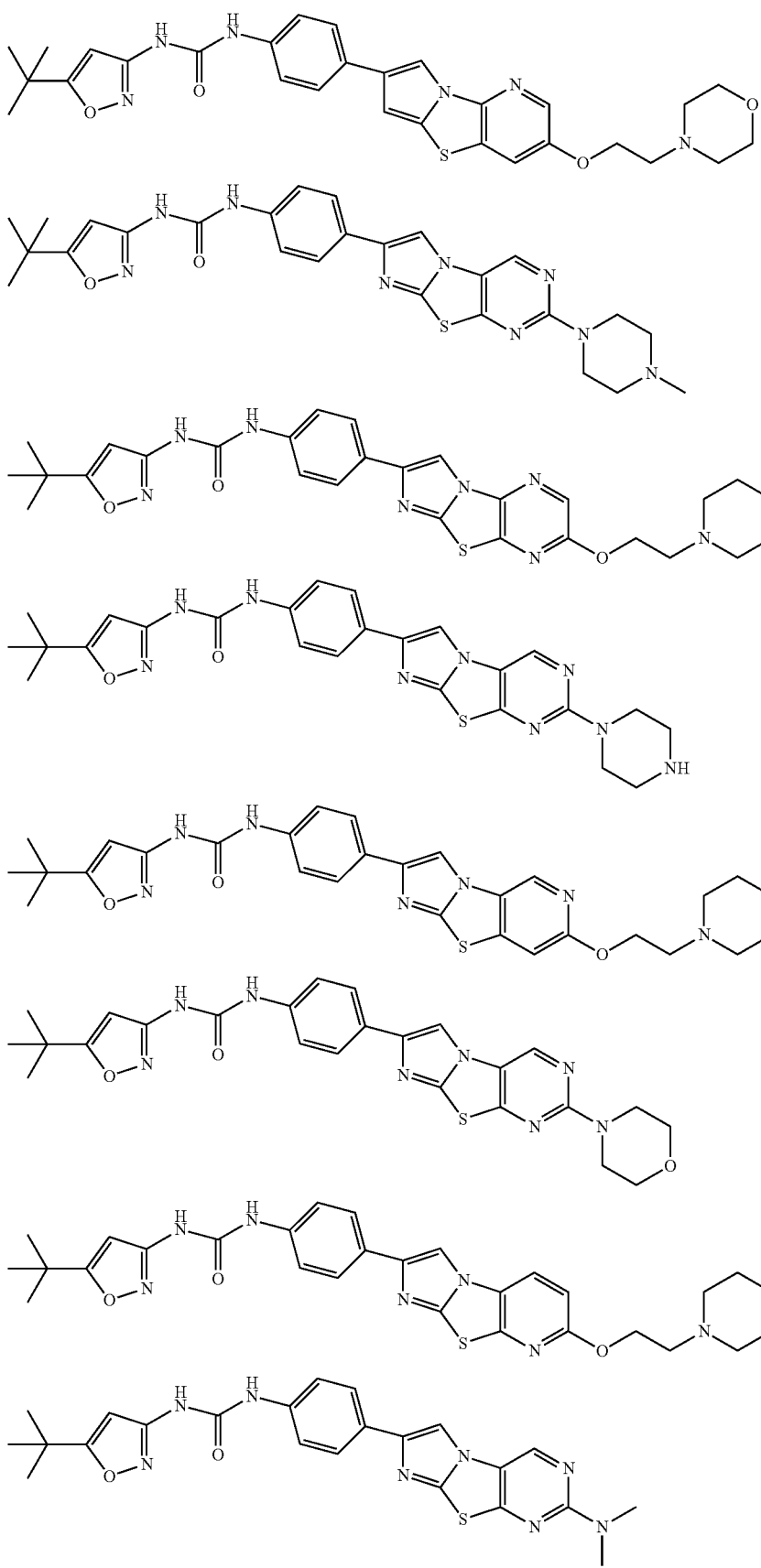

-continued
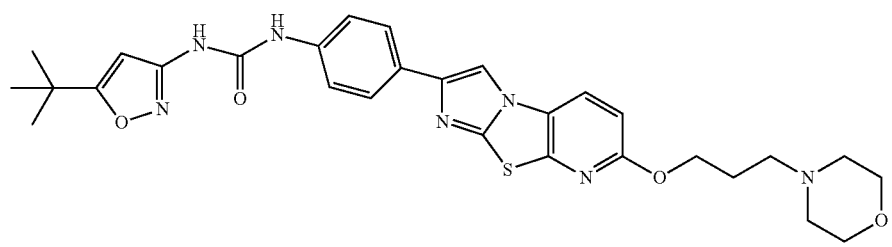
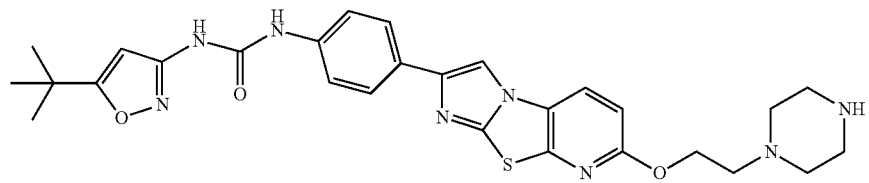
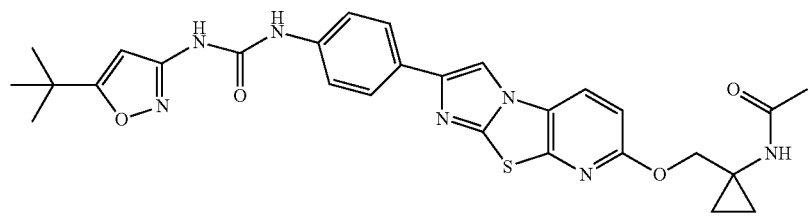
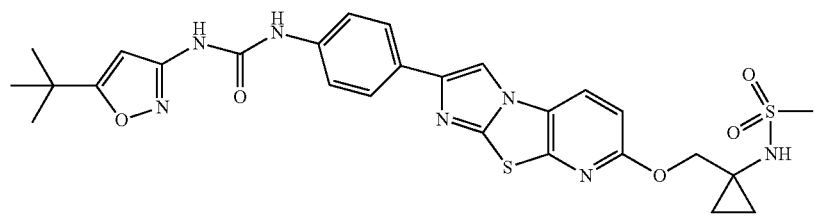
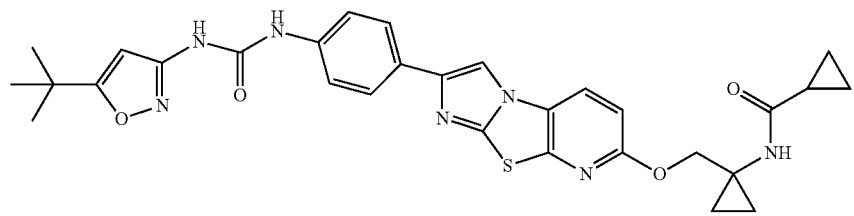
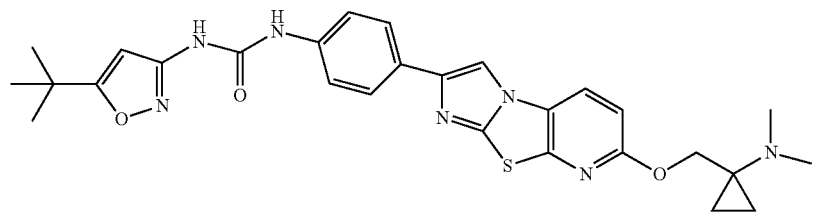
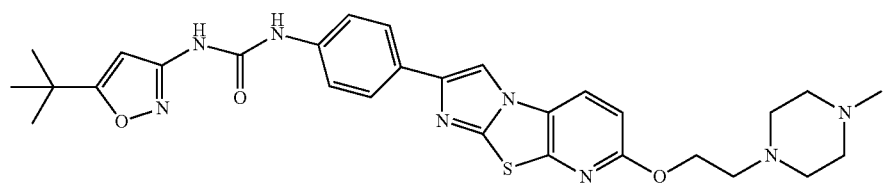
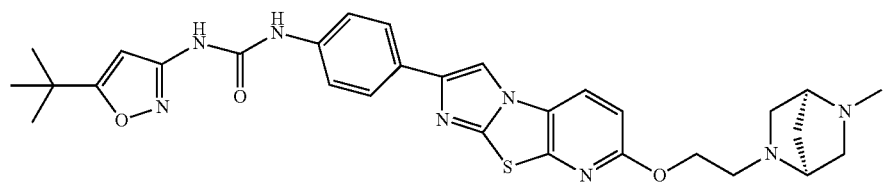

-continued
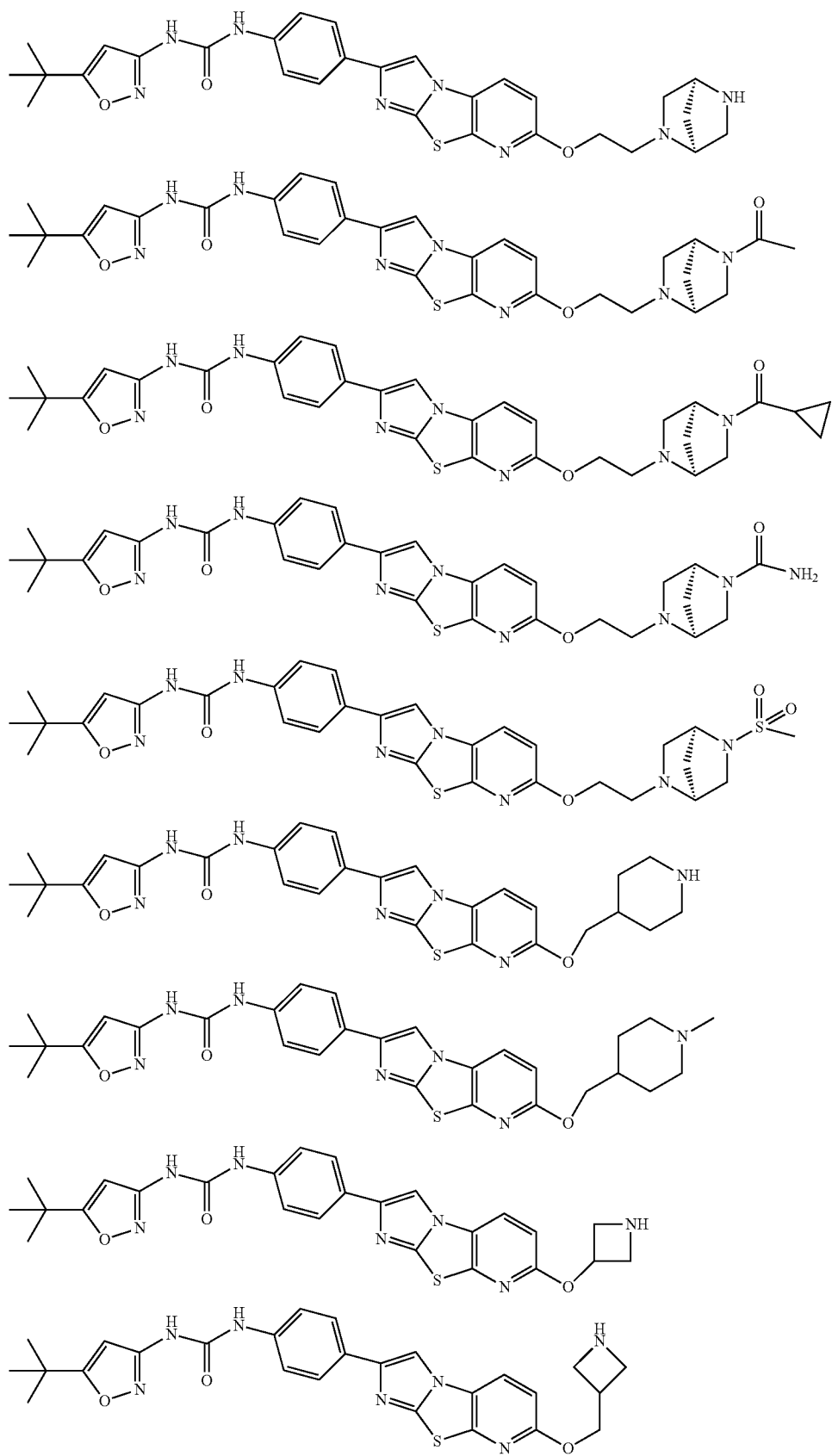

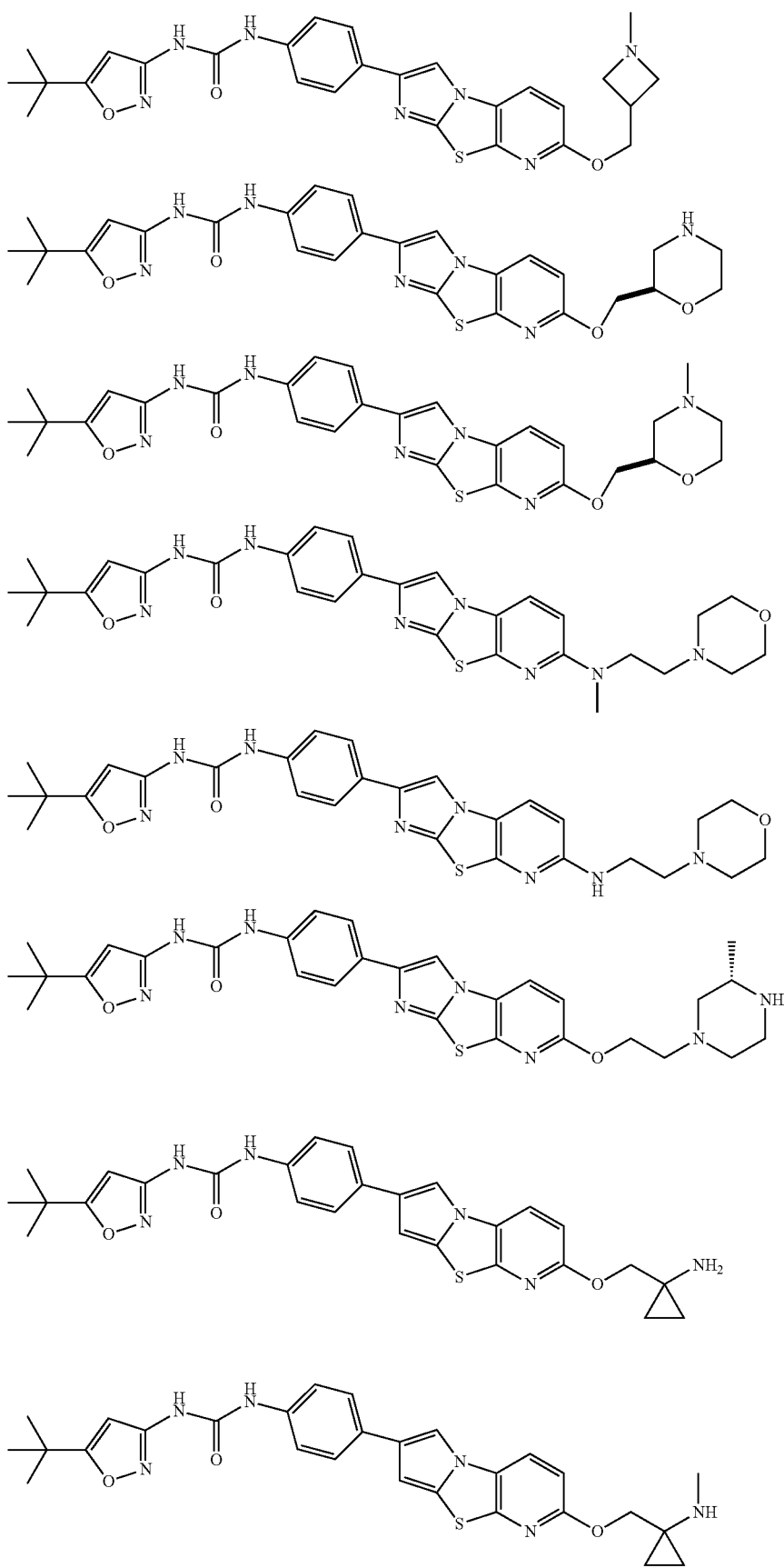

-continued
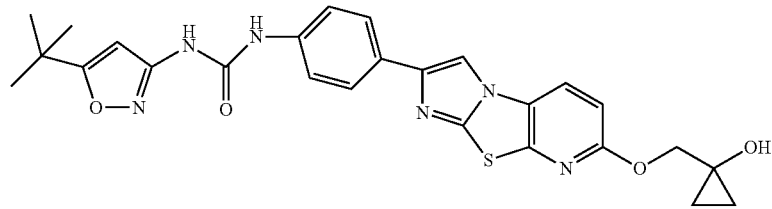
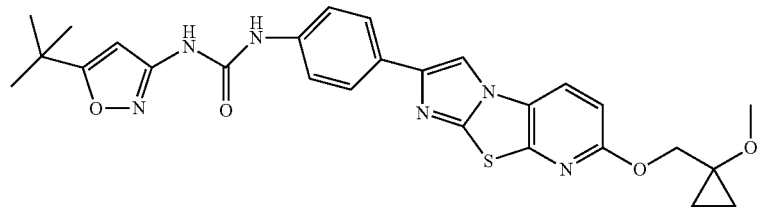
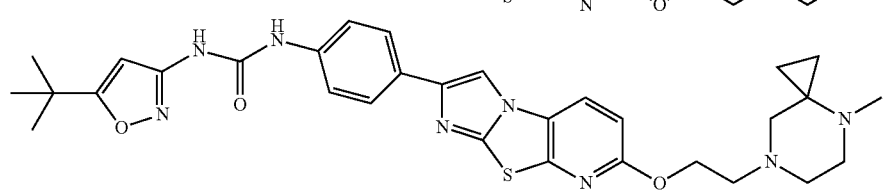
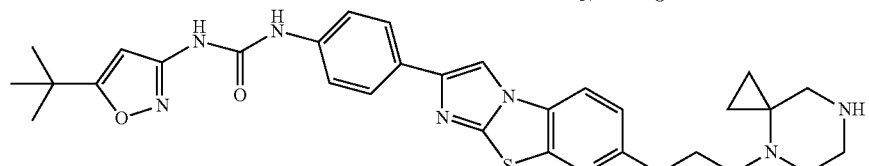
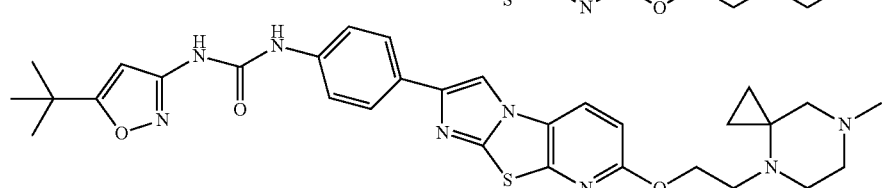
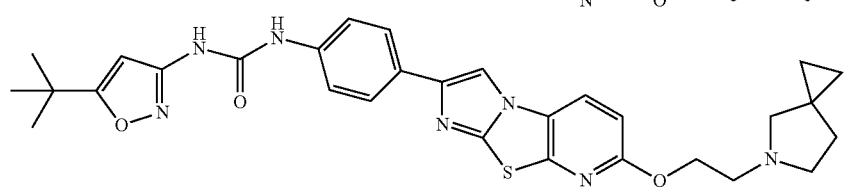
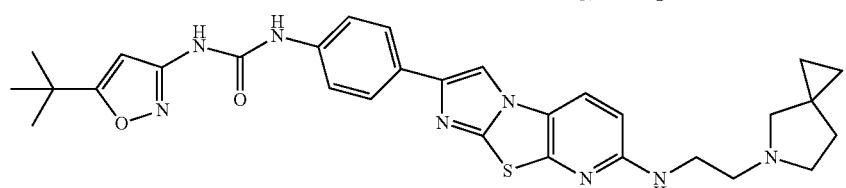
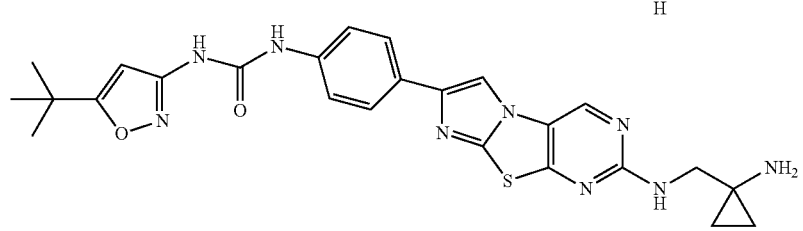

-continued
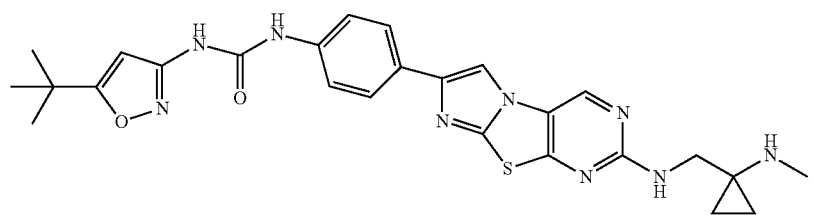
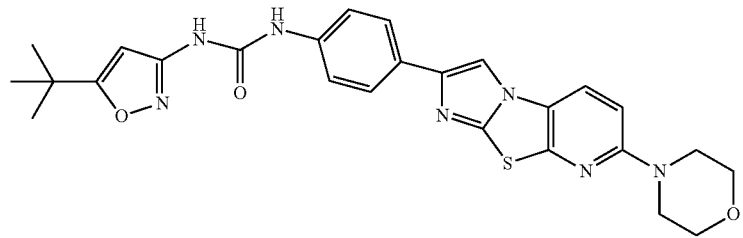
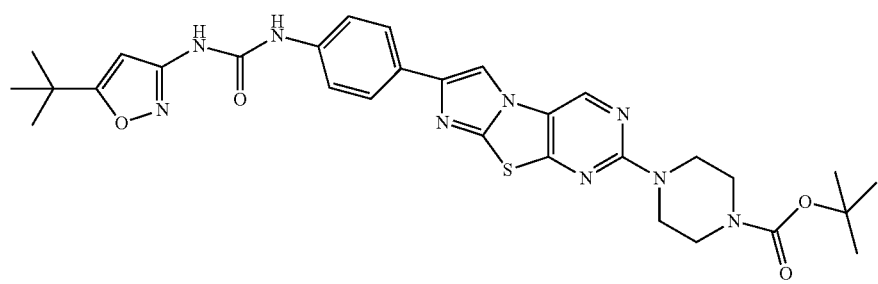
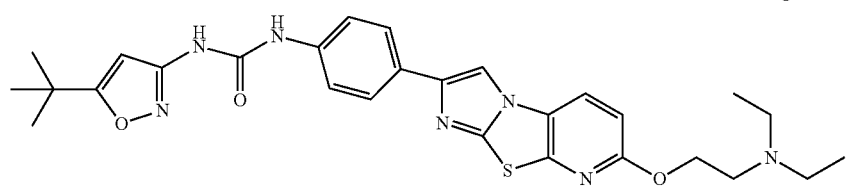
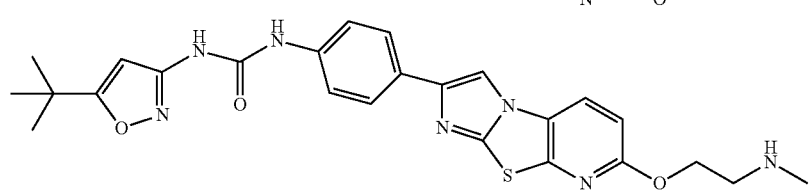
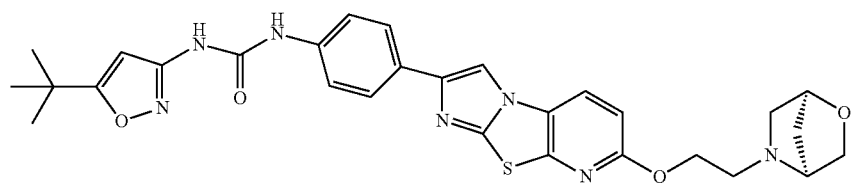
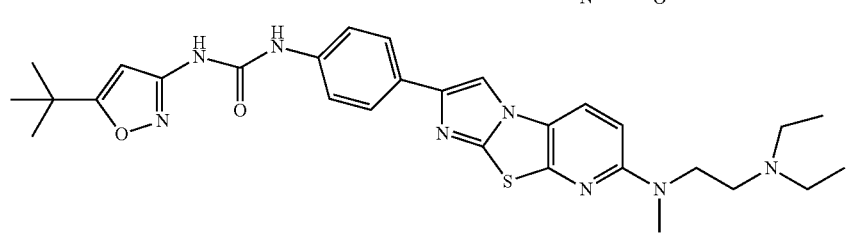
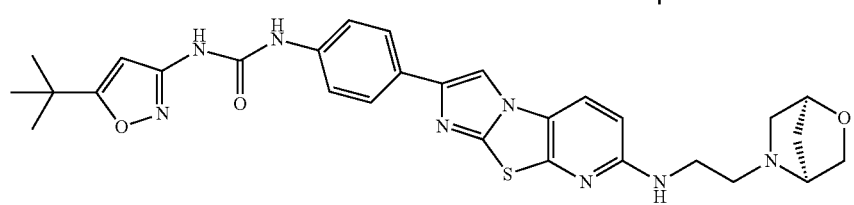

-continued
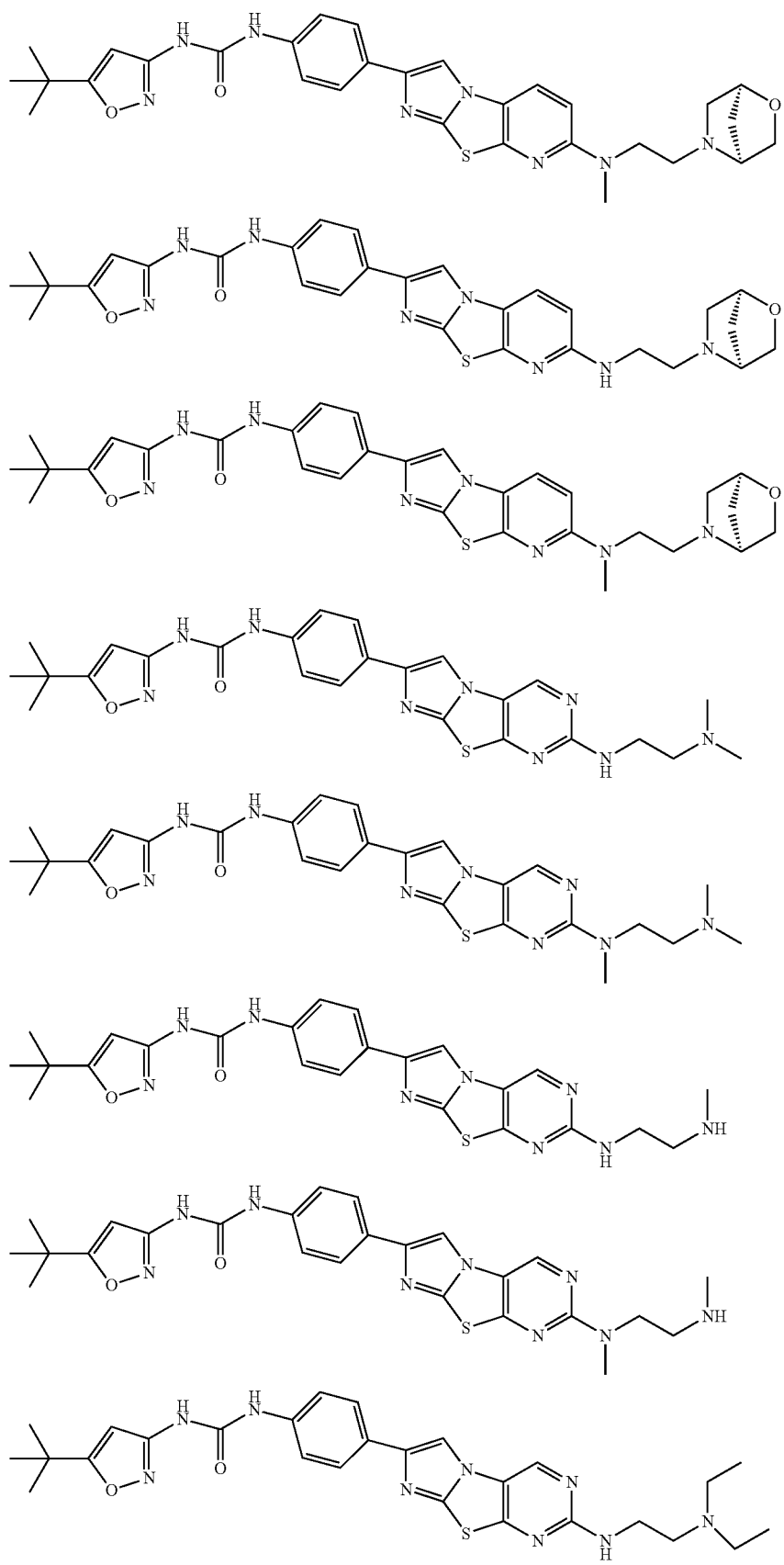

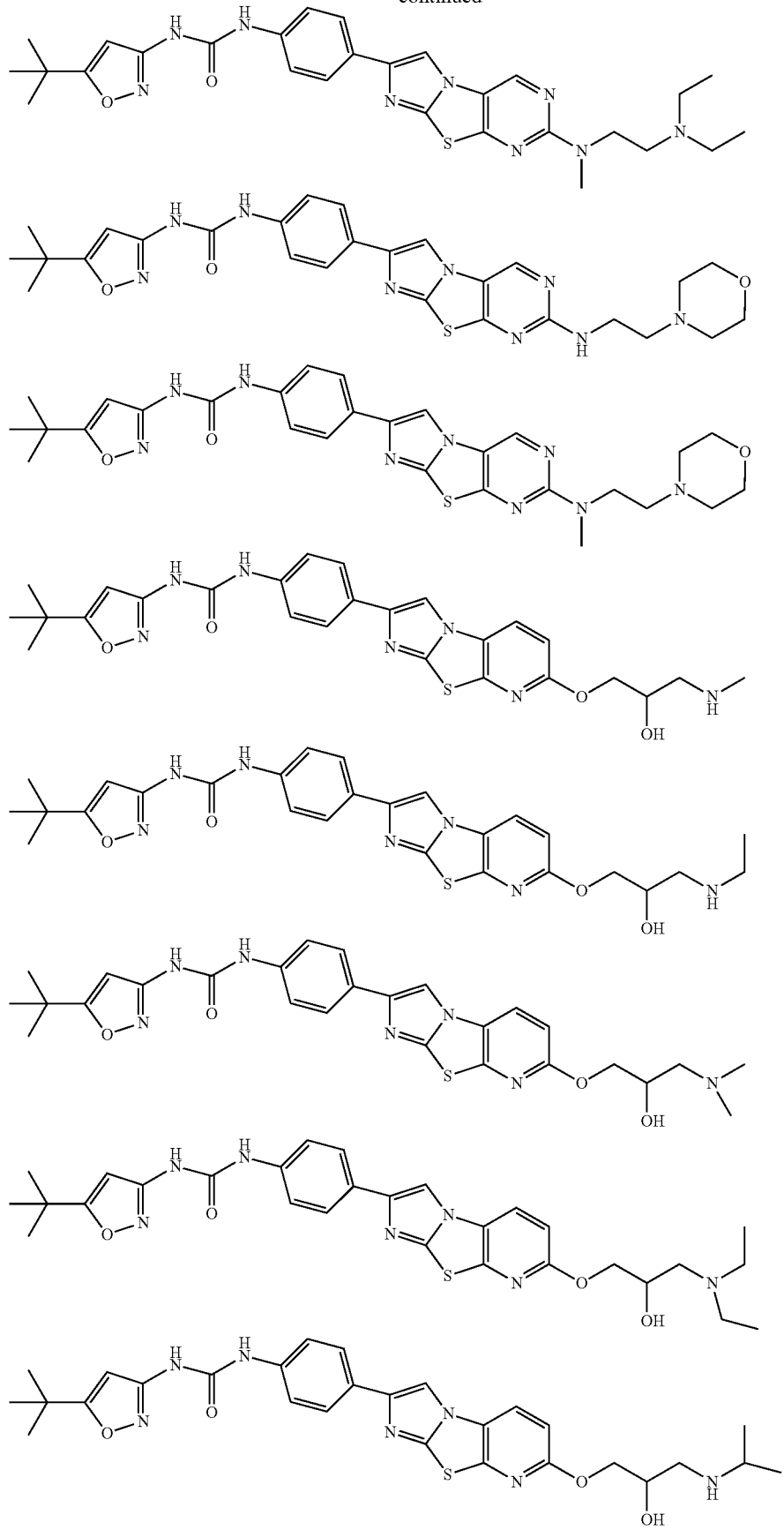

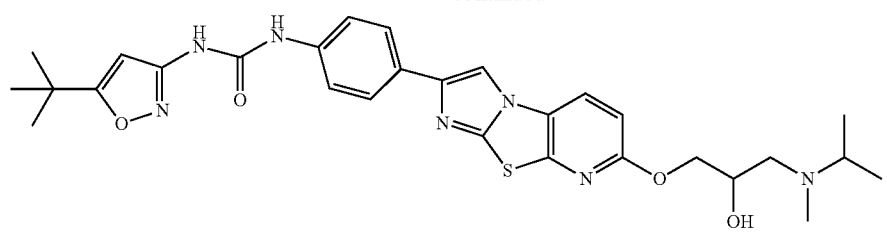
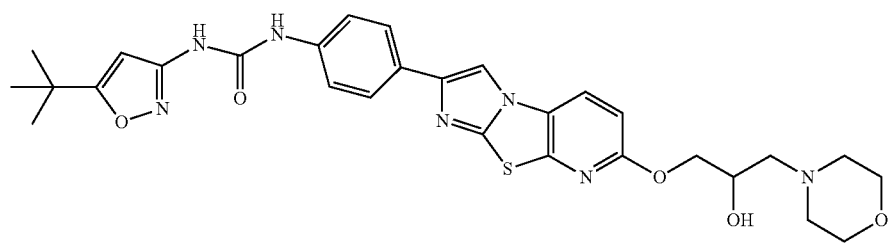
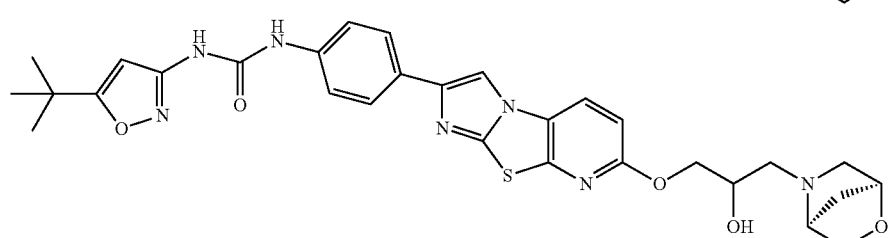
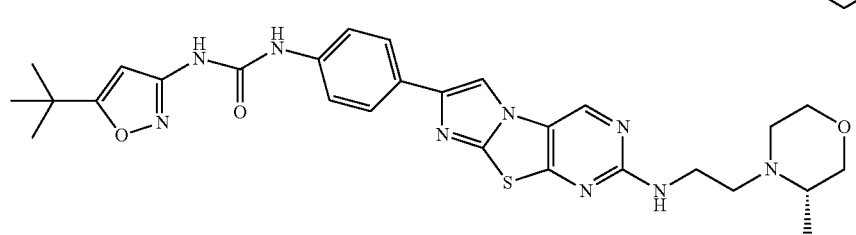
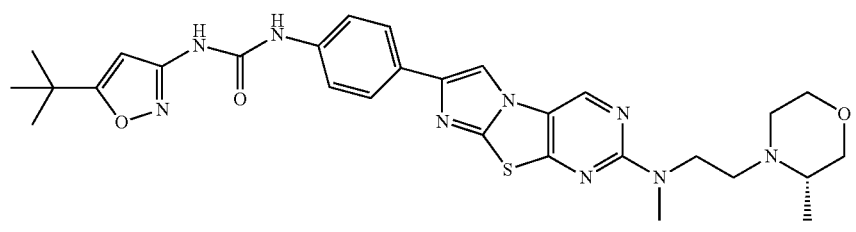
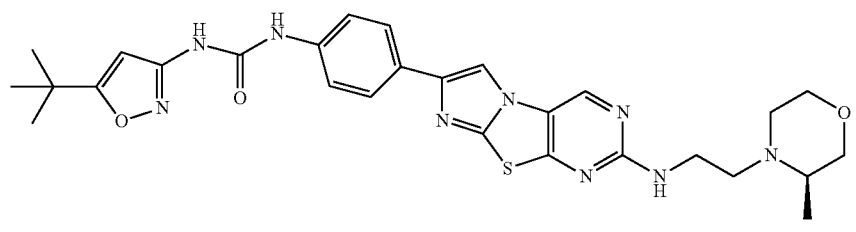
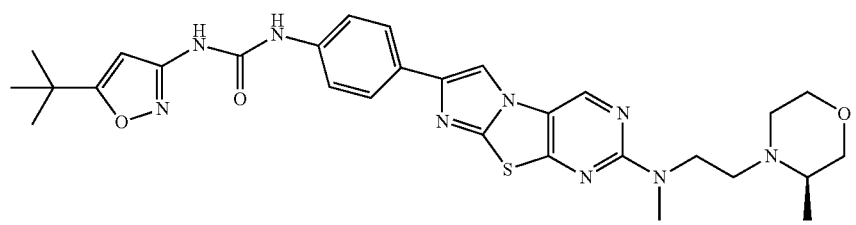

-continued
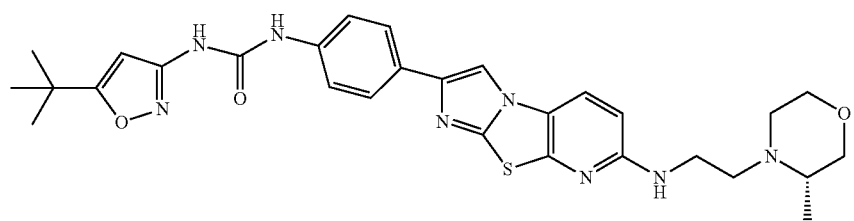
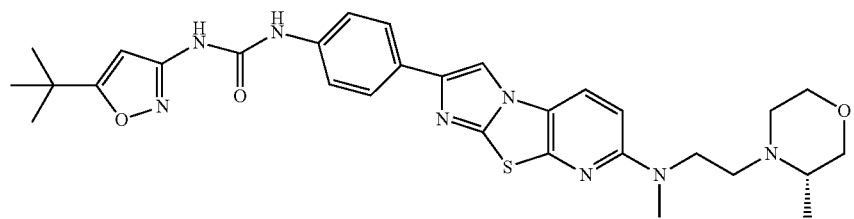
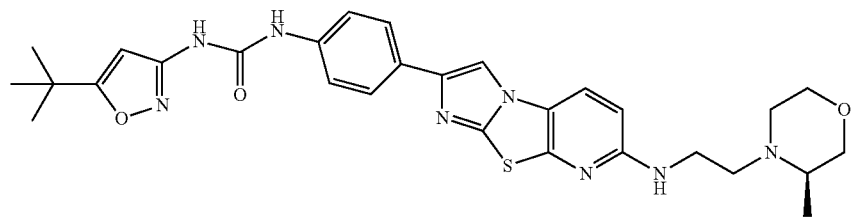
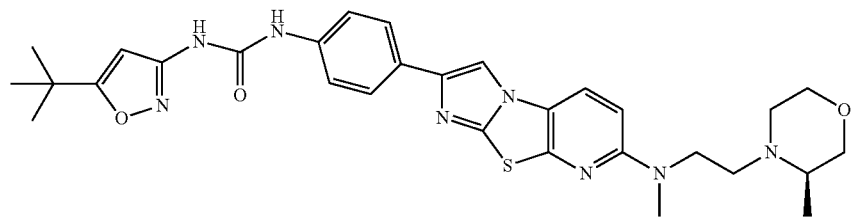
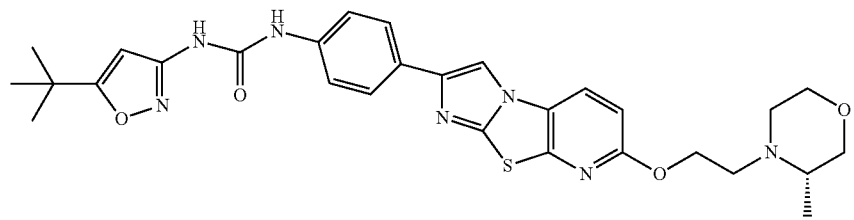
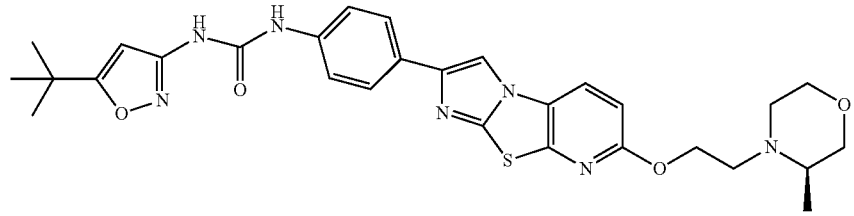
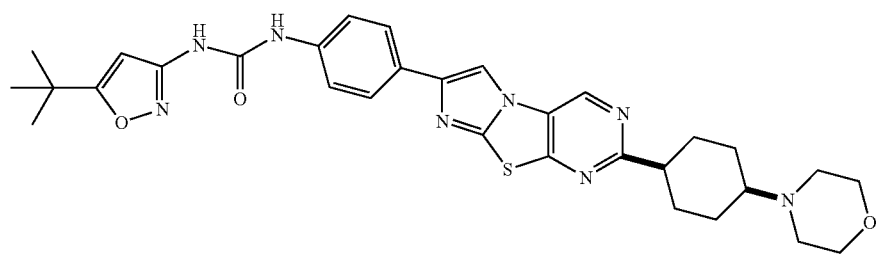

-continued
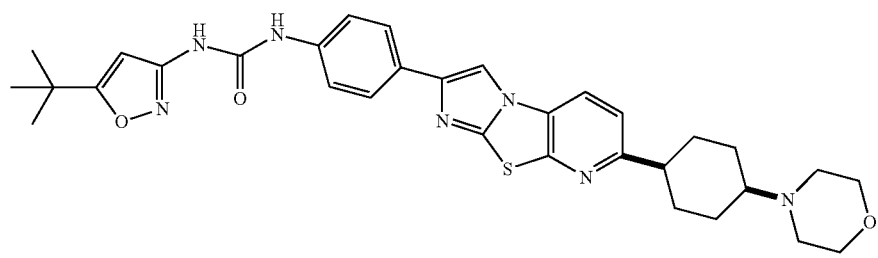
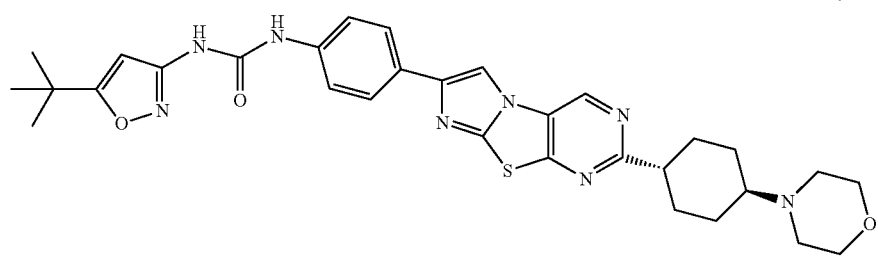
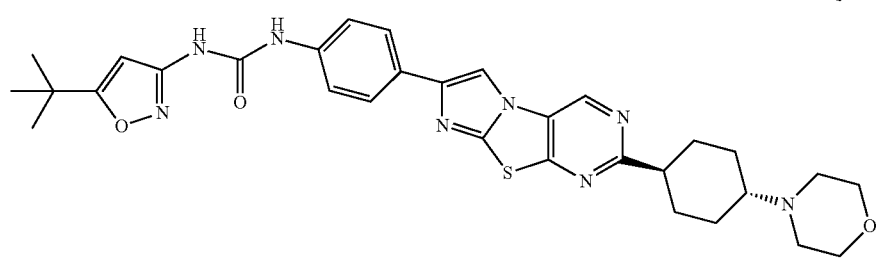
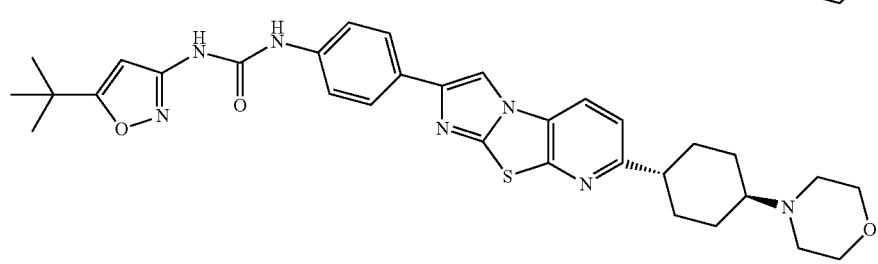
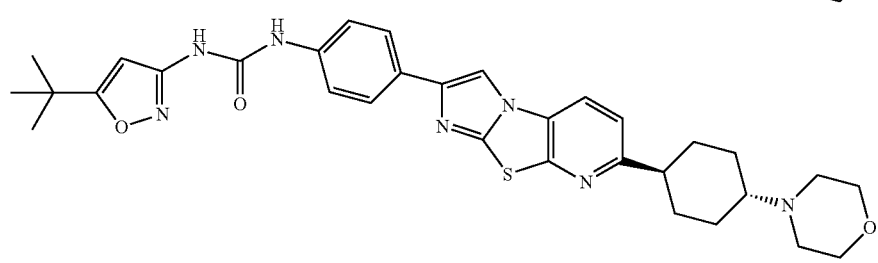
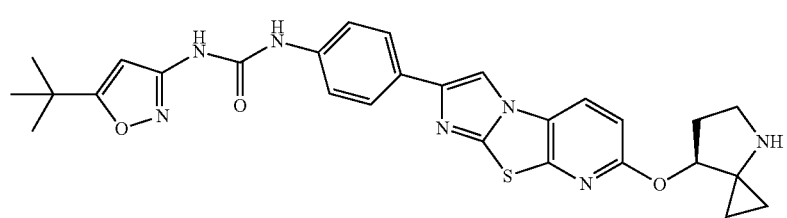
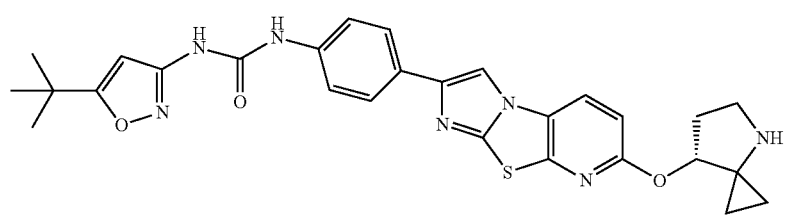

-continued
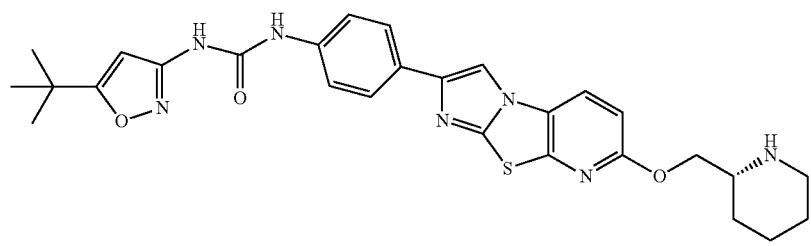
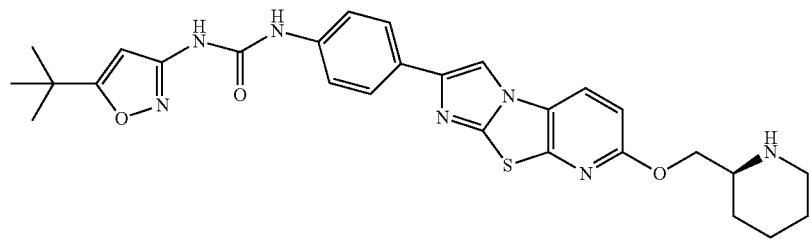
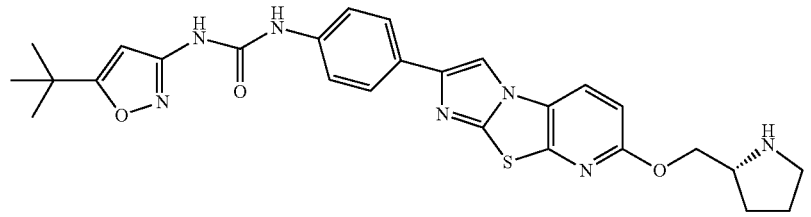
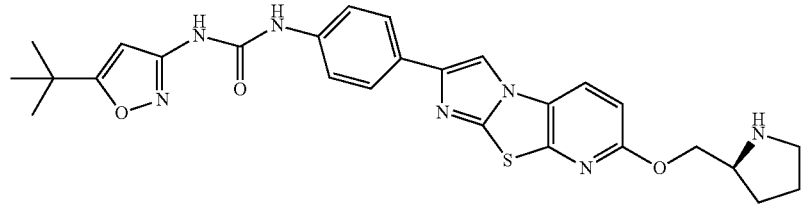
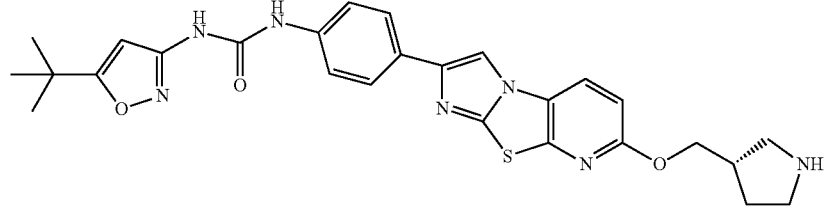
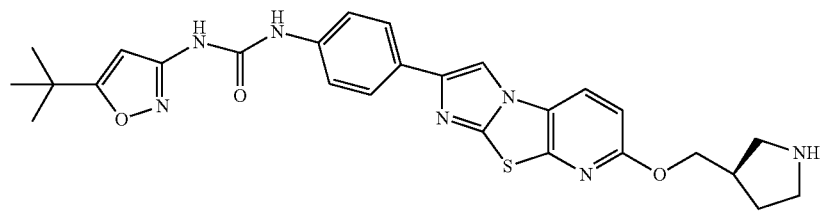
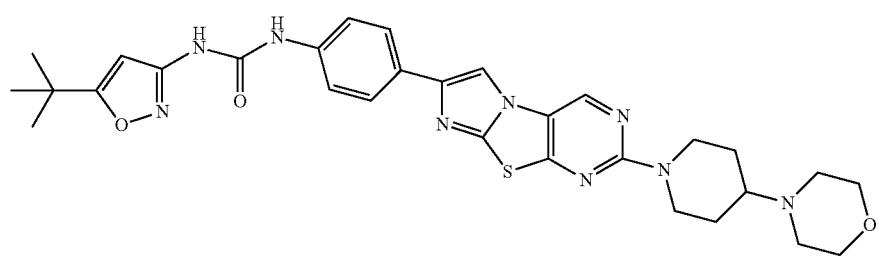

-continued

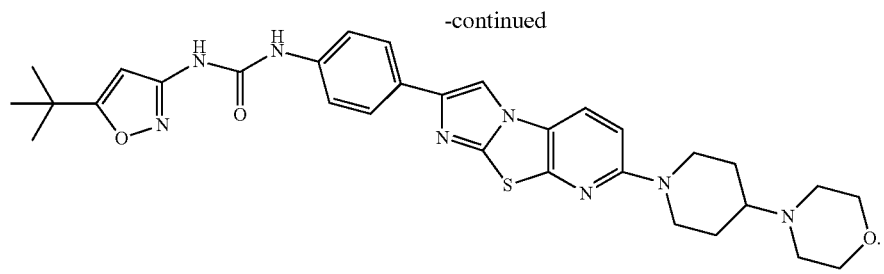

7. A pharmaceutical composition comprising the compound of formula (I) or a pharmaceutically acceptable salt thereof as defined in claim 1, as well as a pharmaceutically acceptable carrier, adjuvant, excipient, or diluent.

8. The compound of formula (I) or a pharmaceutically acceptable salt thereof as defined in claim 1 in preparation of a medicament as a Flt3 kinase inhibitor.

9. A method of treating acute myeloid leukemia or chronic myeloid leukemia comprising administering a therapeutically effective amount of the compound of formula (I) according to claim 1 or a pharmaceutically acceptable salt thereof, wherein said method is performed by inhibiting Flt3 kinase activities.

* * * * *